United States Patent
Suh et al.

(10) Patent No.: US 10,543,101 B1
(45) Date of Patent: Jan. 28, 2020

(54) INTERVERTEBRAL IMPLANTS AND RELATED SYSTEMS AND METHODS

(71) Applicant: CTL Medical Corporation, Addison, TX (US)

(72) Inventors: Sean Suh, Milltown, NJ (US); Jon Suh, Ambler, PA (US)

(73) Assignee: CTL Medical Corporation, Addison, TX (US)

( * ) Notice: Subject to any disclaimer, the term of this patent is extended or adjusted under 35 U.S.C. 154(b) by 611 days.

(21) Appl. No.: 14/956,084

(22) Filed: Dec. 1, 2015

(51) Int. Cl.
*A61F 2/44* (2006.01)

(52) U.S. Cl.
CPC ...... *A61F 2/442* (2013.01); *A61F 2002/4475* (2013.01); *A61F 2220/0008* (2013.01)

(58) Field of Classification Search
CPC ...................................... A61F 2/44–2002/4495
See application file for complete search history.

(56) References Cited

U.S. PATENT DOCUMENTS

| | | | | |
|---|---|---|---|---|
| RE28,841 E * | 6/1976 | Allgower | ........... | A61B 17/8014 606/282 |
| 5,549,612 A * | 8/1996 | Yapp | ................. | A61B 17/7059 411/200 |
| 6,206,922 B1 * | 3/2001 | Zdeblick | .............. | A61B 1/3132 623/17.11 |
| 6,558,423 B1 * | 5/2003 | Michelson | ......... | A61B 17/7059 623/17.11 |
| 6,730,127 B2 * | 5/2004 | Michelson | .............. | A61F 2/442 606/247 |
| 6,972,019 B2 * | 12/2005 | Michelson | ............ | A61F 2/4455 606/247 |
| 7,794,502 B2 * | 9/2010 | Michelson | ............ | A61F 2/4611 606/301 |
| 8,882,814 B2 * | 11/2014 | Suh | ........................ | A61B 17/80 606/280 |
| 9,271,836 B2 * | 3/2016 | Pavento | ............. | A61B 17/7059 |
| 9,326,861 B2 * | 5/2016 | Iott | ..................... | A61F 2/30744 |
| 2002/0016595 A1 * | 2/2002 | Michelson | ......... | A61B 17/8605 606/301 |
| 2005/0071008 A1 * | 3/2005 | Kirschman | ........ | A61B 17/7059 623/17.11 |
| 2006/0122603 A1 * | 6/2006 | Kolb | .................. | A61B 17/7059 606/287 |
| 2007/0123885 A1 * | 5/2007 | Kirschman | ........ | A61B 17/7059 606/279 |

(Continued)

*Primary Examiner* — Zade Coley
(74) *Attorney, Agent, or Firm* — Brainspark Associates, LLC

(57) ABSTRACT

An intervertebral device may include a body configured for insertion between adjacent vertebrae of a patient. The body may include a wall having a first surface, a second surface, and a thickness extending between the first and second surfaces. The wall may include a through aperture extending between a first opening on the first surface and a second opening on the second surface. The through aperture configured to receive a fastening element. A recess may be disposed in a side wall of the aperture and may extend into the thickness of the body in a direction substantially transverse to an axis of the aperture. Additionally, at least one offsetting element may be positioned adjacent the through aperture. The at least one offsetting element may be configured to apply a force to the fastening element.

17 Claims, 48 Drawing Sheets

(56) References Cited

U.S. PATENT DOCUMENTS

| | | | |
|---|---|---|---|
| 2009/0210062 A1* | 8/2009 | Thalgott | A61F 2/4465 623/17.16 |
| 2010/0057206 A1* | 3/2010 | Duffield | A61F 2/4455 623/17.16 |
| 2010/0280557 A1* | 11/2010 | Suh | A61B 17/7049 606/305 |
| 2010/0292737 A1* | 11/2010 | Suh | A61B 17/8033 606/286 |
| 2011/0190770 A1* | 8/2011 | Suh | A61B 17/80 606/70 |
| 2013/0238095 A1* | 9/2013 | Pavento | A61B 17/7059 623/17.16 |
| 2014/0039623 A1* | 2/2014 | Iott | A61F 2/30744 623/17.16 |
| 2014/0236241 A1* | 8/2014 | Scioscia | A61B 17/7059 606/279 |
| 2016/0000573 A1* | 1/2016 | Iott | A61F 2/30744 623/17.16 |

* cited by examiner

INTERVERTEBRAL IMPLANTS AND RELATED SYSTEMS AND METHODS

TECHNICAL FIELD

Various aspects of the present disclosure relate generally to intervertebral implants and related systems and methods. More specifically, the present disclosure relates to intervertebral devices, systems, and methods for deployment within a body of a patient.

BACKGROUND

As shown in FIG. 1, a patient's spinal column 2 includes twenty-six bones called vertebrae 4 which protect the spinal cord. While the shape and/or size of each vertebra 4 varies depending on the placement, loading, posture, and/or pathology within spinal column 2, each vertebra 4 is composed of cancellous bone, which is a spongy type of osseous tissue. The cancellous bone of each vertebra 4 is then covered by a thin coating of cortical bone, which is a hard and dense type of osseous tissue. An intervertebral disc 6 is positioned between each pair of adjacent vertebrae 4 in spinal column 2. Each disc 6 forms a fibrocartilaginous joint between adjacent vertebrae 4 so as to allow relative movement between adjacent vertebrae 4. Beyond enabling relative motion between adjacent vertebrae 4, each disc 6 acts as a shock absorber for spinal column 2.

Each disc 6 comprises a fibrous exterior surrounding an inner gel-like center which cooperate to distribute pressure evenly across each disc 6, thereby preventing the development of stress concentrations that might otherwise damage and/or impair vertebrae 4 of spinal column 2. Discs 6 are, however, subject to various injuries and/or disorders which may interfere with a disc's ability to adequately distribute pressure and protect vertebrae 4. For example, disc herniation, degeneration, and infection of discs 6 may result in insufficient disc thickness and/or support to absorb and/or distribute forces imparted to spinal column 2. Disc degeneration, for example, may result when the inner gel-like center begins to dehydrate, which may result in a degenerated disc 8 having decreased thickness. This decreased thickness may limit the ability of degenerated disc 8 to absorb shock which, if left untreated, may result in pain and/or vertebral injury.

While pain medication, physical therapy, and other non-operative conditions may alleviate some symptoms, such interventions may not be sufficient for every patient. Accordingly, various procedures have been developed to surgically improve patient quality of life via abatement of pain and/or discomfort. Such procedures may include, discectomy and fusion procedures, such as, for example, anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF). During a discectomy, all or a portion of a damaged disc, e.g., a degenerated disc 8, is removed via an incision, typically under X-ray guidance.

Following the discectomy procedure, a medical professional may determine an appropriate size of interbody device 10 (FIG. 2) via one or more distractors and/or trials of various sizes. Each trial and/or distractor may be forcibly inserted between adjacent vertebrae 4. Upon determination of an appropriate size, one or more of an ACIF, ALIF, DLIF, PLIF, and/or TLIF may be performed by placing an appropriate interbody device 10 (e.g., a cage, spacer, block) between adjacent vertebrae 4 in the space formed by the removed degenerated disc 8. Placement of such interbody devices 10 within spinal column 2 may prevent spaces between adjacent vertebrae 4 from collapsing, thereby preventing adjacent vertebrae 4 from resting immediately on top of one another and inducing fracture of vertebra 4, impingement of the spinal cord, and/or pain. Additionally, such interbody devices 10 may facilitate fusion (e.g., bone to grow together) between adjacent vertebrae 4 by stabilizing adjacent vertebrae 4 relative to one another. Accordingly, as shown in FIG. 2, such interbody devices 10 often may include one or more fixation members such as, for example, screws 12 extending through interbody device 10 and into adjacent vertebrae 4.

Often, following the removal of the distractor and/or trial, a medical professional must prepare one or more bores or holes in a vertebra 4 intended to receive screws 12. Such holes may be formed with the aid of a separate drill guide positioned proximate or abutting vertebra 4 and inserting a drill therethrough. Alternatively, such holes may be formed free hand, without the use of a drill guide. Further, since spinal column 2 is subject to dynamic forces, often changing with each slight movement of the patient, such screw(s) 12 have a tendency to back out (e.g., unscrew) and/or dislodge from interbody device 10, thereby limiting interbody device's 10 ability to stabilize adjacent vertebrae 4, and consequently, promote fusion. Additionally, if screw(s) 12 back out and/or dislodge from interbody device 10, they may inadvertently contact, damage, and/or irritate surrounding tissue. Further, interbody device 10 is commonly comprised of a radiopaque material so as to be visible in situ via x-ray and other similar imaging modalities. However, such materials may impede sagittal and/or coronal visibility, thereby preventing visual confirmation of placement and post-operative fusion.

Thus, there remains a need for improved interbody devices, associated systems, and methods relating thereto.

SUMMARY

Examples of the present disclosure relate to, among other things, intervertebral implants. Each of the embodiments disclosed herein may include one or more of the features described in connection with any of the other disclosed embodiments.

In one example, an intervertebral device may include a body configured for insertion between adjacent vertebrae of a patient. The body may include a wall having a first surface, a second surface, and a thickness extending between the first and second surfaces. The wall may include a through aperture extending between a first opening on the first surface and a second opening on the second surface. The through aperture configured to receive a fastening element. A recess may be disposed in a side wall of the aperture and may extend into the thickness of the body in a direction substantially transverse to an axis of the aperture. Additionally, at least one offsetting element may be positioned adjacent the through aperture. The at least one offsetting element may be configured to apply a force to the fastening element.

Additionally or alternatively, examples of the device may include one or more of the following features: application of a force on the fastening element by the at least one offsetting element may be configured to laterally urge the fastening element relative to the recess; upon the application of a force on the fastening element by the at least one offsetting element, interference between the at least one offsetting element, the recess, and the fastening element may be configured to urge the fastening element in a posterior direction relative to the recess; the recess may be configured to retain the fastening element within the through aperture; the recess may be configured to receive an actuation portion of the fastening element; the fastening element may be a screw, and the recess may be configured to receive a head of the screw; actuating the at least one offsetting element may cause the at least one offsetting element to engage a portion of the fastening element; the at least one offsetting element may be eccentrically shaped; the at least one offsetting element may include at least one of a planar portion and a concave portion, and wherein the at least one offsetting elements includes a convex portion; the at least one offsetting element may be movable relative to the body; the fastening element may be a first fastening element, the device may further include a second fastening element, the through aperture may be configured to receive each of the first fastening element and the second fastening element; application of a force on the second fastening element by the at least one offsetting element may be configured to laterally urge the second fastening element relative to the recess; the at least one offsetting element may be positioned between each of the first fastening element and the second fastening element, and actuation of the at least one offsetting element may be configured to laterally urge the first fastening element and the second fastening element relative to the recess, simultaneously; and the at least one offsetting element may be a first offsetting element, the device may further include a second offsetting element positioned adjacent said through aperture, application of a force on the second fastening element by the second offsetting element may be configured to laterally urge the second fastening element relative to the recess independently of the first fastening element.

In another example, an intervertebral device may include a body configured for insertion between adjacent vertebrae of a patient. The body may include a wall having a first surface, a second surface, and a thickness extending between the first and second surfaces. The wall may include a through aperture extending between a first opening on the first surface and a second opening on the second surface. The body may also include two lateral supports extending from the first wall. Each lateral support may define a first window and a second window along a lateral surface of the body. The device may further include a fastening element positioned within the through aperture and at least one offsetting element positioned adjacent said through aperture.

Additionally or alternatively, examples of the device may include one or more of the following features: at least a portion of the body may be radiopaque and each of the first and second windows may be radiolucent; a radiolucent graft containment sheath may be disposed about the body; and the body may include a tapered keel.

In another example, an intervertebral device may include a body configured for insertion between adjacent vertebrae of a patient. The body may include a wall having a first surface, a second surface, and a thickness extending between the first and second surfaces. The wall may include a through aperture extending between a first opening on the first surface and a second opening on the second surface. The body also may include two lateral supports extending from the wall. Each lateral support may define a first window and a second window along a lateral surface of the body. The body may further define at least one window along the wall of the body. Additionally, the device may include a radiolucent graft containment sheath disposed about the body.

Additionally or alternatively, examples of the device may include one or more of the following features: the body may be radiopaque and each of the first and second windows may be radiolucent; the body may include a tapered keel; the tapered keel may be offset from an anterior-most surface of the body; a graft retention member may extend along at least a portion of the body; and a plurality of protrusions may extend along the body.

It may be understood that both the foregoing general description and the following detailed description are exemplary and explanatory only and are not restrictive of the invention, as claimed.

As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" as used herein is used in the sense of "example," rather than "ideal."

BRIEF DESCRIPTION OF THE DRAWINGS

The accompanying drawings, which are incorporated in and constitute a part of this specification, illustrate exemplary arrangements of the present disclosure and together with the description, serve to explain the principles of the disclosure.

DETAILED DESCRIPTION

Screw Blocking Mechanisms

Figure 3A:
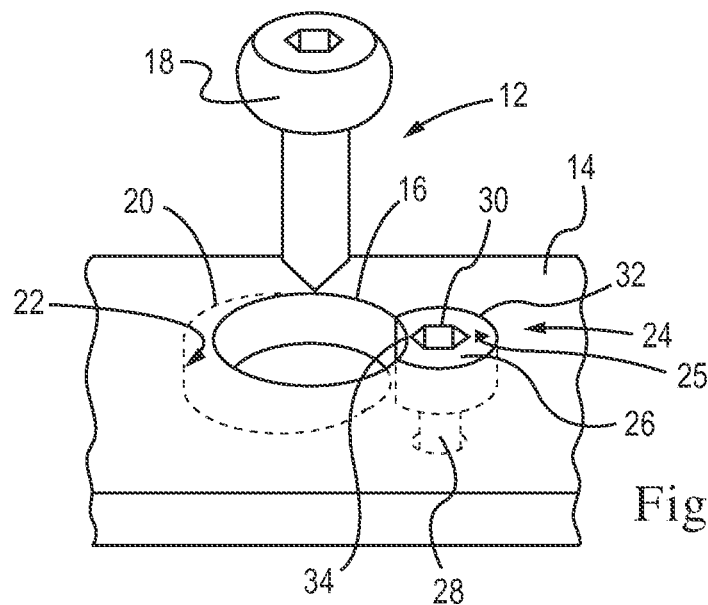
FIG. 3A illustrates an exemplary screw blocking mechanism prior to insertion of a screw.
Figure 3B:
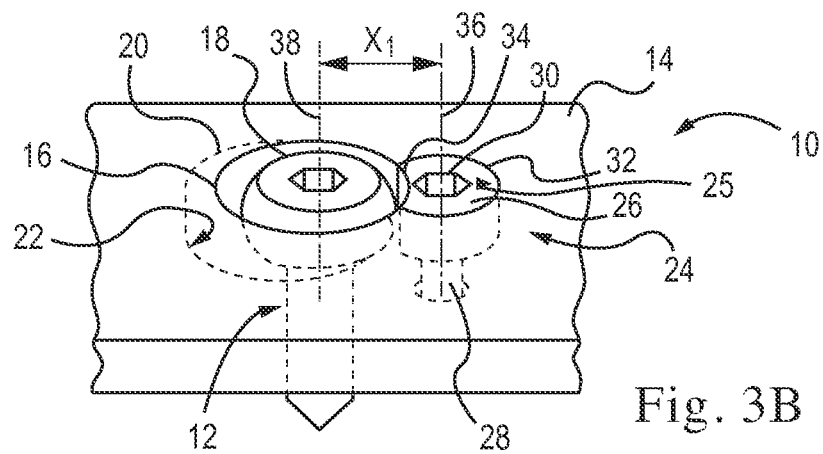
FIG. 3B illustrates the screw blocking mechanism of FIG. 3A, after insertion of a screw, in an unlocked configuration.
Figure 3C:
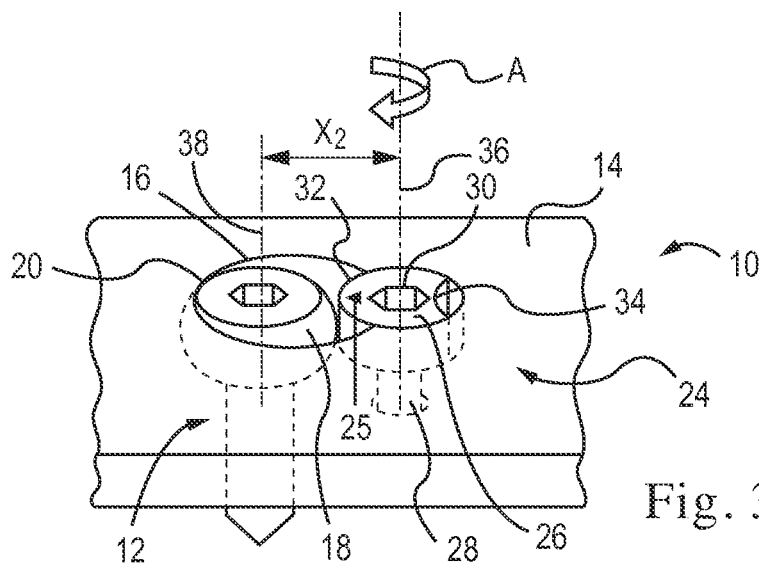
FIG. 3C illustrates the screw blocking mechanism of FIG. 3B in a locked configuration.

FIGS. 3A-3C illustrate an exemplary system for preventing fixation devices such as screws 12 from backing out (e.g., unscrewing) and/or dislodging from interbody device 10. As used herein, such systems may be considered screw blocking mechanisms. As shown in FIG. 3A, an exemplary interbody device 10 may include a wall having a first face 14, an opposite second face, and a thickness extending therebetween. Face 14 may define a screw receiving face in a substrate (e.g., a plate and/or block) of interbody device 10. For example, the substrate of interbody device 10 may be comprised of any one or more of metal, metal alloys, plastics, ceramics, and elastomers capable of receiving and retaining screw 12 therein. Face 14 may define an aperture 16 configured to receive, engage, and/or complement a head 18 (e.g., an actuation portion) of screw 12 therein. While only a single aperture 16 is depicted in FIG. 3A, face 14 may define any appropriate number of apertures 16. For example, in some arrangements, face 14 may define two, three, four, or more apertures, as will be described in further detail below. Aperture 16 may have any appropriate shape configured to receive one or more screws 12 therein. For example, as shown in FIG. 3A, aperture 16 may be generally circular. In other arrangements described below, however, aperture 16 may be generally ovular, triangular, square, cross-shaped, and or irregular. Additionally, aperture 16 may be tapered so as to receive screw 12 at an angle therethrough. Aperture 16 may be a through hole and/or a counterbore. For example, aperture 16 may extend from a first opening on face 14 through the thickness of the wall of interbody device 10 to the second face, opposite face 14.

A sidewall of aperture 16 may a define a recess 20 extending into the direction the thickness in a direction substantially transverse to an axis of aperture 16 and having a surface 22 configured to cooperate with and/or correspond in profile with head 18 of screw 12. For example, surface 22 may be generally curved, arcuate, and/or rounded so as to receive, engage, complement, and/or mate with an exterior side and/or top surface of generally curved, arcuate, and/or rounded head 18 of screw 12. As shown in FIG. 3A, recess 20 may comprise a pocket or space into which head 18 may be moved upon the application of a substantially lateral force, as will be described in further detail below. As shown in FIG. 3A, aperture 16 may define a single (e.g., only one) recess 20. In other arrangements, however, aperture 16 may define multiple recesses 20 corresponding in number to a number of screws 12 to be received within aperture 16, as will be described in further detail below. Alternatively, aperture 16 may define a different number of recesses 20 than a number of screws 12 to be received within aperture 16, as will be described in further detail below.

The substrate of interbody device 10 may further include an offsetting element 24. As shown in FIG. 3A, offsetting element 24 may be positioned adjacent aperture 16 so as to cooperate with head 18 to prevent screw 12 from backing out (e.g., unscrewing) or dislodging from interbody device 10. Further, offsetting element 24 may be movably received within the substrate of interbody device 10. For example, in some arrangements, offsetting element 24 may be rotatably received within the substrate of interbody device 10. In other arrangements, however, offsetting element 24 may be configured for lateral or translational movement with respect to the substrate of interbody device 10. For example, offsetting element 24 may include a wedge element configured to be inserted between screw head 18 and aperture 16 so as to laterally urge or otherwise bias screw head 18 toward and/or into recess 20. Alternatively, offsetting element 24 may include a spring element configured to bias screw head 18 laterally toward recess 20. Further, in some arrangements, offsetting element 24 may include a sliding element configured to laterally urge screw head 18 toward recess 20. Still further, offsetting element 24 may include one or more shape memory alloy (SMA) portions comprising a SMA material, such as, for example, NITINOL™. Such materials, upon activation (e.g., application of heat and/or exposure to body chemistry), reform to a "remembered" shape. That is, upon application of an activating force, offsetting element 24 may transition to its "remembered" configuration and laterally urge screw head 18 towards recess 20. In yet a further example, any of the above noted offsetting elements 24 may be used in combination with one another so as to produce a composite actuation force.

As shown in FIG. 3A, offsetting element 24 may include a cam head 26 coupled to a shaft 28. Shaft 28 may extend into the substrate of interbody device 10 and include any appropriate threading or similar retention mechanism (FIG. 5C) configured to movably couple offsetting element 24 to interbody device 10. Accordingly, interbody device 10 may include an internally threaded bore for cooperation with shaft 28. Cam head 26 may include an actuator receiving element such as, for example, a hex-shaped bore 30 configured to cooperate with any appropriate rotatable driver (e.g., key, screw driver, hex driver, etc.). While bore 30 is described and illustrated as a hex-shaped bore 30, it is understood that any appropriately shaped bore may be used so as to cooperate with any correspondingly shaped driver and/or driver tip. Cam head 26 may be eccentrically and/or irregularly shaped. For example, as shown, cam head 26 may include a crescent-shaped member have a convex portion 32 and a concave portion 34. Concave portion 34 may be diametrically spaced from convex portion 32. More particularly, concave portion 34 may include a radius of curvature similar to the radius of curvature of aperture 16. Cam head 26 may further include one or more tactile, visual, or other indicia 25 configured to facilitate a medical professional in determining whether offsetting element 24 is in the unlocked configuration (FIGS. 3A, 3B) or the locked or blocked configuration (FIG. 3C). In one exemplary arrangement, indicia 25 may include an arrow pointed or directed toward concave portion 34. Alternatively, concave portion 34 may be replaced with a substantially flat planar surface, or a convex configuration (not shown).

In an unlocked configuration, prior to insertion of screw 12 into interbody device 10, as shown in FIG. 3A, concave portion 34 may be positioned adjacent to aperture 16 while convex portion 32 is positioned away or spaced from aperture 16. Thus, as a result of concave portion 34 including a similar curvature as aperture 16, offsetting element 24 does not extend into aperture 16. That is, in the unlocked configuration, concave portion 34 may form a side-wall of aperture 16. In other words, concave portion 34 may complete, or otherwise continue (e.g., fills in) the circular shape of aperture 16. Upon movement or rotation of cam head 26 to a locked or blocked configuration (FIG. 3C), convex portion 32 is positioned adjacent aperture 16 while concave portion 34 is positioned away or spaced from aperture 16. Consequently, convex portion 32 extends into or otherwise protrudes into aperture 16.

FIGS. 3B and 3C illustrate an exemplary manner of preventing screw 12 from backing out (e.g., unscrewing) and/or dislodging from interbody device 10. For example, FIG. 3B illustrates interbody device 10 having offsetting element 24 in the unlocked configuration in which screw 12 has been positioned within aperture 16. As shown in FIG. 3B, aperture 16 may be configured to receive head 18 of screw 12 with sufficient clearance such that screw 12 may be loosely or exactly inserted into aperture 16. That is, a dimension, diameter, and/or shape of aperture 16 may be defined so as to correspond within a desired tolerance to a dimension, diameter, and/or shape of head 18 of screw 12. Moreover, head 18 may be completely received within aperture 16 so that head 18 is flush and/or below face 14. In the unlocked configuration, as shown in FIG. 3B, a central longitudinal axis 36 of shaft 28 may be positioned at a distance X1 from a central longitudinal axis 38 of screw 12. Accordingly, with distance X1 between shaft 28 of offsetting element 24 and screw 12, head 18 of screw 12 may be spaced from surface 22 of recess 20.

Upon rotation of offsetting element 24, for example, in direction A as shown in FIG. 3C, cam head 26 of offsetting element 24 may be rotated such that convex portion 32 may be brought in contact with the side surface of head 18 of screw 12. As such, screw 12 may be pushed, moved, biased, or otherwise urged laterally toward and/or into recess 20 and the external side and/or top surface of head 18 of screw 12 may be held close to or in contact with surface 22. Additionally, due to the shape and/or configuration (e.g., curvature) of surface 22 and/or the external side and/or top surface of head 18, actuation of offsetting element 24 may cause interference between head 18 and recess 20 such that head 18 is forced downward (e.g., in a posterior (e.g., deeper) direction of vertebra 4). Accordingly, in the locked or blocked configuration, as shown in FIG. 3C, offsetting element 24 may be configured to retain screw 12 in interbody device 10. Often, the vertebra 4 into which screw 12 is screwed, as described in further detail below, has a relatively low density such that the laterally directed force applied to screw 12 via offsetting element 24 is greater than the resistive force applied by vertebra 4 to screw 12. In some instances, however, the vertebra 4 into which screw 12 is screwed has a relatively high density such that the resistive force applied by vertebra 4 to screw 12 is greater than the laterally directed force applied to screw 12 via offsetting element 24. In such cases, upon actuation of offsetting element 24, screw 12 may remain stationary while the substrate of interbody device 10 may move laterally in microscopic motion until the external side and/or top surface of head 18 may be urged into recess 20. In such a case, actuation of screw offsetting element 24 may place head 18 of screw 12 in tension. Accordingly, upon any force being applied to screw 12 which would otherwise cause screw 12 to back out (e.g., unscrew) and/or dislodge from vertebra 4 and/or interbody device 10, screw 12 will be urged toward recess 20 and prevented from backing out by a top surface of recess 20.

Figure 4:
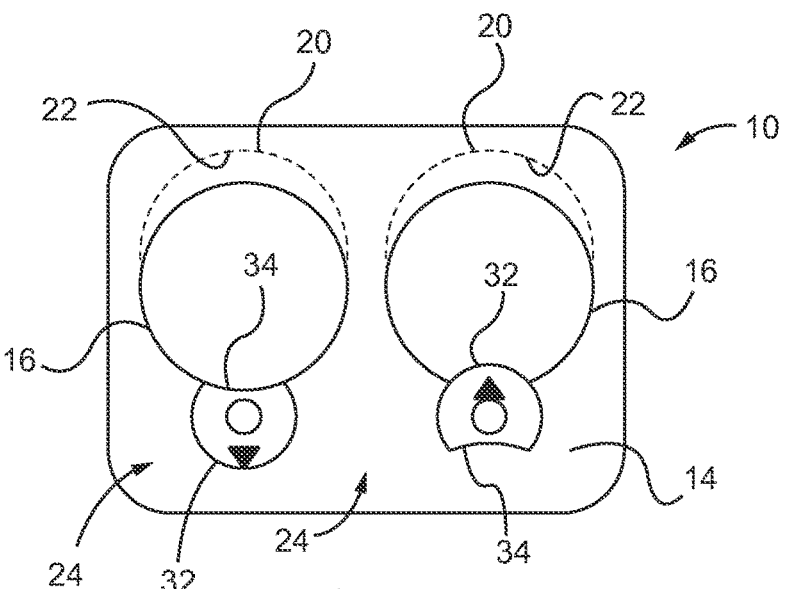
FIG. 4 illustrates a further exemplary screw blocking mechanism.

As noted above, face 14 of the substrate of interbody device 10 may define a plurality of apertures 16. For example, as shown in FIG. 4, face 14 may define two apertures 16. Each aperture 16 may be configured to receive one or more screws 12 therein. For example, each aperture 16 may be configured to receive a single screw 12. Additionally, similar to the arrangement described above, each aperture 16 may define a recess 20 having a surface 22 configured to cooperate with and/or correspond in profile to head 18 of screw 12. As shown in FIG. 4, each recess 20 may comprise a pocket or space into which head 18 may be moved upon the application of a lateral force. Each recess 20 may include substantially similar or differing geometric configurations and/or dimensions. Further, as shown in FIG. 4, the substrate of interbody device 10 may further include one or more offsetting elements 24 associated with each aperture 16. Offsetting elements 24 may be similar in construction and manner of use as described above in connection FIGS. 3A-3C. In the example of FIG. 4, each aperture 16 may include a single recess 20, configured to receive a head 18 of a single screw 12 upon actuation of an individual offsetting element 24. As such, a first screw 12 positioned within a first aperture 16 may be moved towards the locked or blocked configuration (FIG. 3C) upon the actuation of a first offsetting element 24 independently of a second screw 12 positioned within a second aperture 16. In addition, as shown in FIG. 3C, when offsetting element 24 is actuated, only a lateral portion of head 18 at be disposed in recess 20.

Figure 5A:
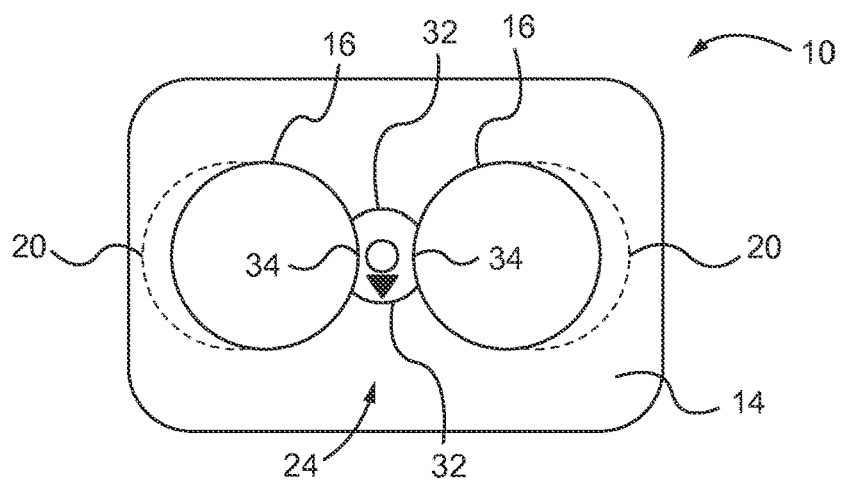
FIGS. 5A and 5B illustrate a still further exemplary screw blocking mechanism.
Figure 5B:
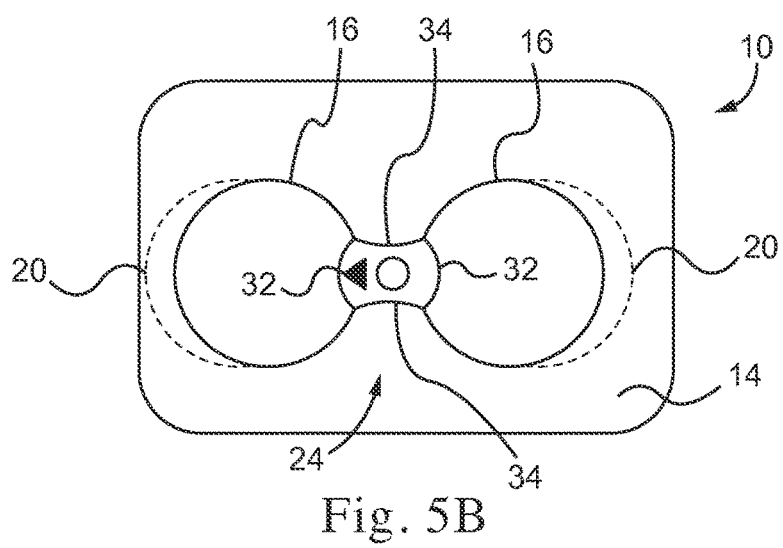

Alternatively, as shown in FIGS. 5A and 5B, multiple screws 12 may be moved towards a locked or blocked configuration simultaneously. That is, the substrate of interbody device 10 depicted in FIGS. 5A and 5B may be similar to that of FIG. 4, except that instead of separate offsetting elements 24, a single offsetting element 24 may be positioned between each aperture 16. Accordingly, in such an arrangement, offsetting element 24 may have a pair of convex portions 32 and a pair of concave portions 34 disposed therebetween, as shown. The pair of concave portions 34 may be diametrically spaced from one another. In an unlocked configuration, prior to insertion of each screw 12 into interbody device 10, as shown in FIG. 5A, a first concave portion 34 may be positioned adjacent to a first aperture 16 while a second concave portion 34 may be positioned adjacent to a second aperture 16. Further, each of the two convex portions 32 may be positioned away or spaced from the first and second apertures 16. Upon movement or rotation of cam head 26 of the offsetting element 24 to the locked or blocked configuration, as shown in FIG. 5B, convex portions 32 are positioned adjacent and protruding into apertures 16 while concave portions 34 are positioned away or spaced from apertures 16. In such a manner, a single offsetting element 24 may be used to retain two separate screws 12 positioned in two separate apertures 16, simultaneously.

It is to be understood that, while the central longitudinal axis 38 of each screw 12 of FIGS. 3B and 3C is depicted as extending generally normal (e.g., perpendicular) to face 14, screws 12 may instead extend at a non-normal (e.g., non-perpendicular) angle relative to face 14. Additionally, while face 14 of the substrate of interbody device 10 is depicted as substantially planar and/or flat in FIGS. 3A-3C, 4, 5A, and 5B, such depictions are merely exemplary. For example, as shown in the cross-sectional view of FIG. 5C, each screw 12 may be positioned at a non-normal angle relative to face 14. Additionally, as shown, face 14 may be rounded, curved, and/or otherwise non-planar.

Figure 5C:
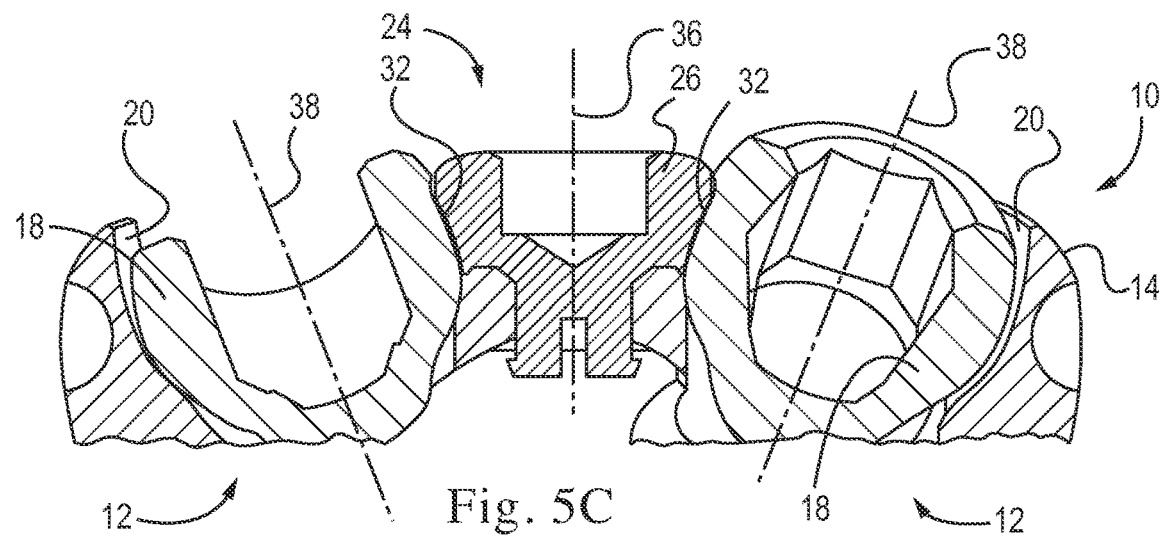
FIG. 5C illustrates a partial cross-sectional view of the exemplary screw blocking mechanism of FIGS. 5A and 5B.
Figure 5D:
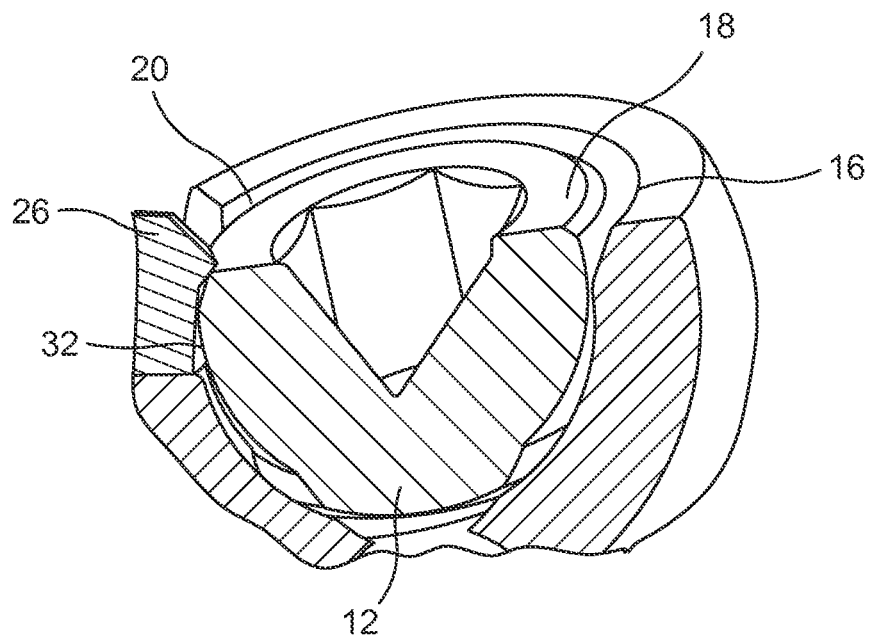
FIGS. 5D and 5E illustrate partial cross-sectional views of the exemplary screw blocking mechanism of FIGS. 5A and 5B under interference.
Figure 5E:
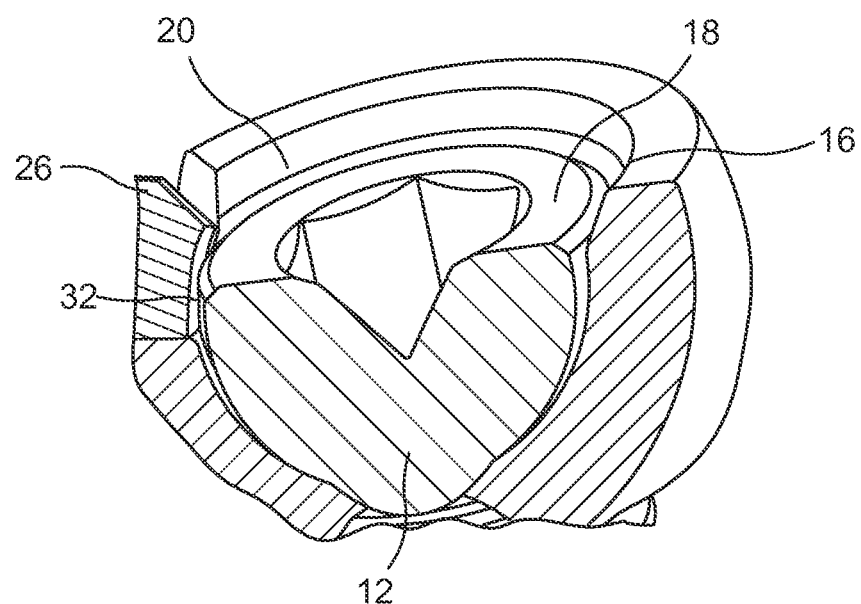

Further, as shown in FIG. 5C, upon rotation of offsetting element 24, convex portions 32 of cam head 26 may be brought in contact with the side surfaces of heads 18 of screws 12. As such, each screw 12 may be pushed, moved, or otherwise urged laterally (in opposing directions) toward recess 20 and the external side and/or top surface of head 18 of screw 12 may be received within recess 20. Additionally, due to the shape and/or configuration (e.g., curvature) of recess 20 and/or the external side and/or top surface of head 18, actuation of offsetting element 24 may cause interference between head 18, offsetting element 24, and recess 20 such that head 18 is forced downward (e.g., in a deeper or posterior direction of vertebra 4). For example, upon rotation (or other such actuation) of offsetting element 24, head 18 of screws 12 may be simultaneously urged laterally toward recess 20 and downward or deeper into vertebra 4 (e.g., in a posterior direction), as shown in FIGS. 5D and 5E. That is, as shown in FIG. 5D, upon rotation or other such actuation of offsetting element 24, convex portions 32 of cam head 26 may be brought in contact with the side surfaces of head(s) 18 of screw(s) 12 which imparts interference between head 18 and offsetting element 24 to push, move, or otherwise laterally urge head 18 toward recess 20. Lateral interference between head 18 and offsetting element 24 may be about 0.1 mm. Further, as shown in FIG. 5E, due to the configuration (e.g., shape and/or size) of offsetting element 24, lateral force applied to head 18 may impart a simultaneous downward (e.g., in a deeper or more posterior direction of vertebra 4) movement of head 18 relative to offsetting element 24. In some arrangements, head 18 may be urged about 0.5 mm downward. Accordingly, in the locked or blocked configuration, as shown in FIG. 5C, offsetting element 24 may be configured to retain screw 12 in interbody device 10.

Figure 6A:
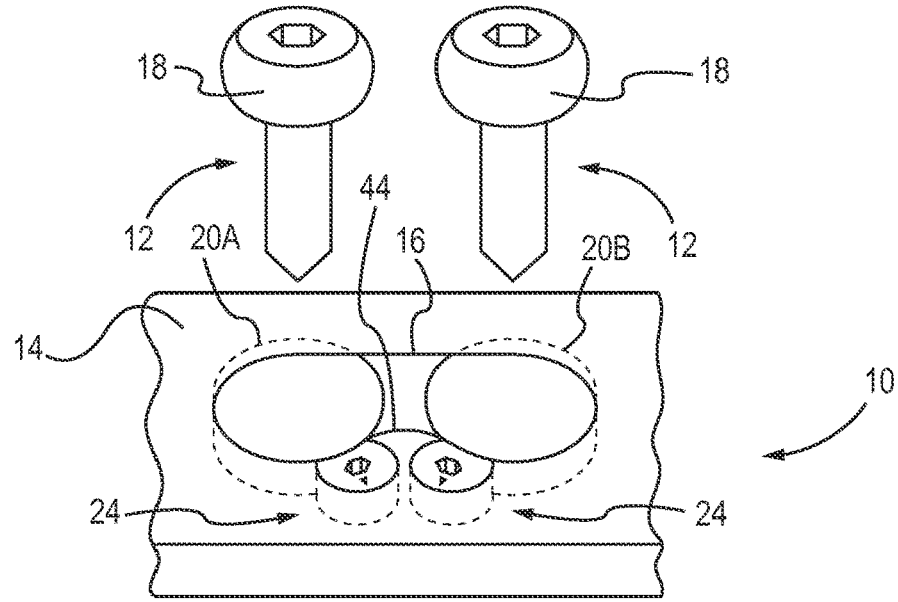
FIGS. 6A and 6B illustrate another exemplary screw blocking mechanism.
Figure 6B:
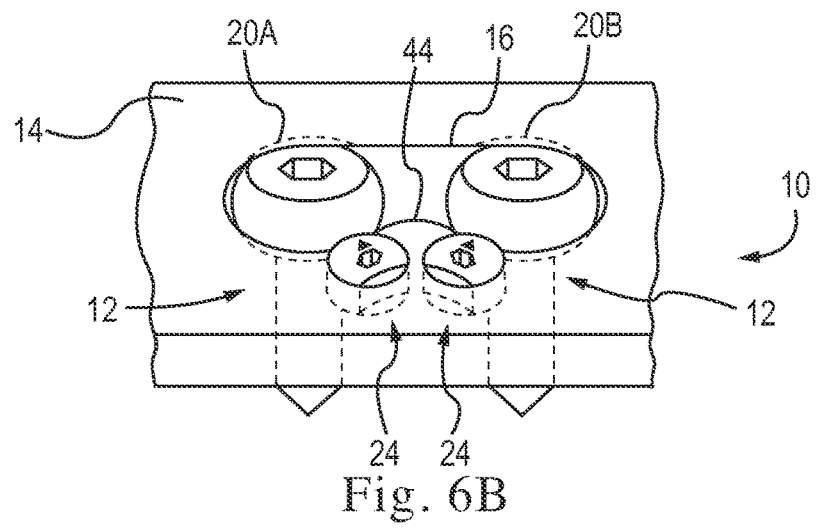

As noted above, each aperture 16 may be configured to receive one or more screws 12 therein. For example, as shown in FIGS. 6A and 6B, a single aperture 16 may be configured (e.g., sized) to receive two screws 12. That is, aperture 16 may be elongated so as to receive two screws 12. While aperture 16 depicted in FIGS. 6A and 6B comprises a generally ovular shape with a single inwardly protruding portion 44 extending radially inwardly from one side thereof, any other appropriate shape configured to receive two screws 12 therein may be used, as will be described in further detail below.

Additionally, while the arrangement of FIGS. 6A and 6B depict a single aperture 16, aperture 16 may define two individual and separate recesses 20. For example, a first recess 20A may be positioned along a first portion of aperture 16 while a second recess 20B may be positioned along a second portion of aperture 16. Each recess 20 may be configured to receive a single screw 12 of the two screws 12. Additionally, similarly to the arrangement of FIG. 4, the substrate of interbody device 10 may further include an offsetting element 24 associated with each screw 12. Each offsetting element 24 may be similar in construction and manner of use as described above in connection FIGS. 3A-3C. Due to the inclusion of a separate offsetting element 24 associated with each screw 12, each screw 12 may be moved towards the locked or blocked configuration, as shown in FIG. 6B, independently of one another.

Figure 7:
FIG. 7 illustrates an exemplary aperture of a screw blocking mechanism.

FIGS. 7, 8A, 8B, and 9-12 illustrate various modifications and arrangements of illustrative examples in accordance with this disclosure. For example, as shown in FIG. 7, aperture 16 may be generally ovular having a substantially constant width w1 so as to receive two or more screws 12 therein. As shown, the ovular shape of aperture 16 does not include or is free from any inwardly protruding portion 44.

Figure 8A:
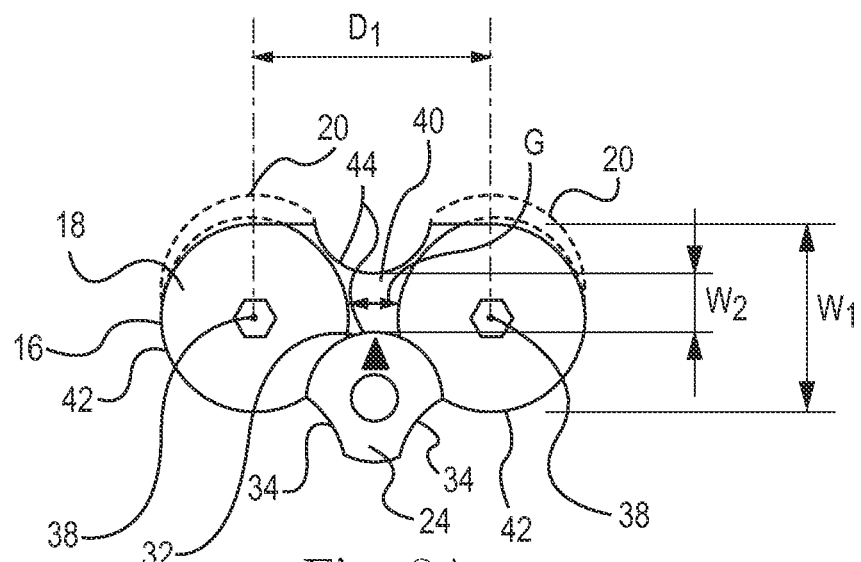
FIGS. 8A and 8B illustrate a further exemplary screw blocking mechanism.

Alternatively, as shown in FIG. 8A, aperture 16 may have a variable width. That is, aperture 16 may include two lateral portions 42 having a first width w1 and a central portion 40 have a second width w2. Width w2 may be relatively smaller than width w1. That is, central portion 40 may be a generally narrowed portion of aperture 16. Indeed, central portion 40 may define a pair of inwardly protruding surfaces 44. In such an arrangement, head 18 of each screw 12 may be spaced from one another. Indeed, as shown in FIG. 8A, central longitudinal axes 38 of each screw 12 may be spaced from one another at a distance of D1. Distance D1 may be such that a gap G is provided between adjacent side surfaces of screws 12.

Figure 8B:
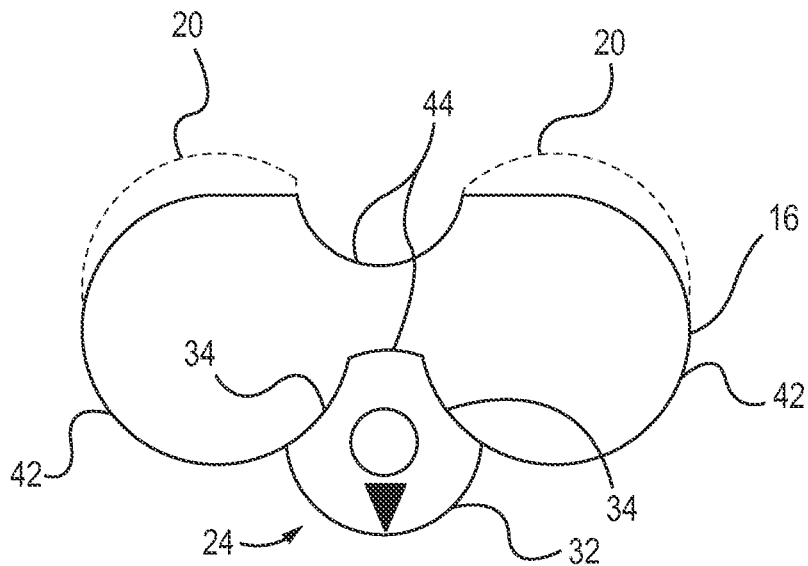
Figure 9:
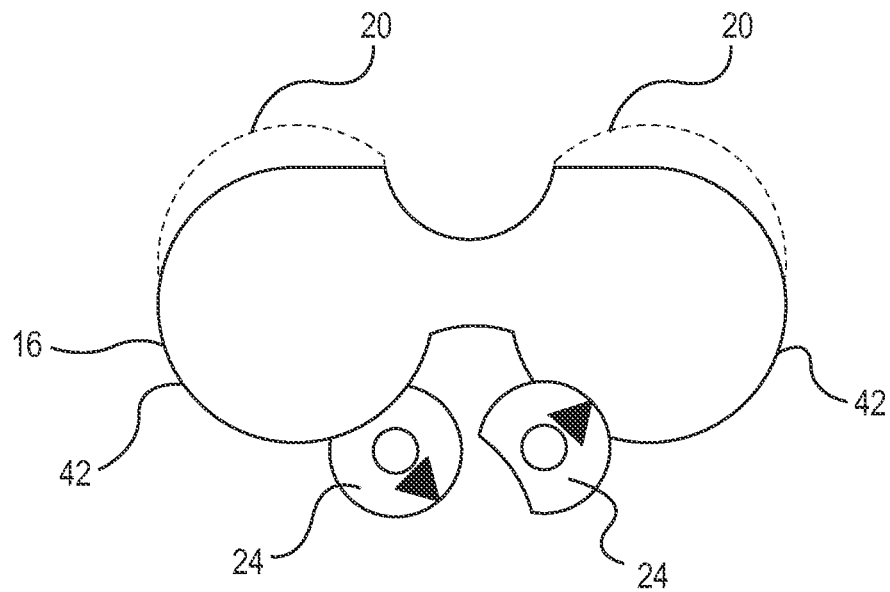
FIGS. 9-12 illustrate exemplary screw blocking mechanisms according to further arrangements.

Further, one or both of the pair of inwardly protruding surfaces 44 may be configured to cooperate with an offsetting element 24. That is, similarly to the arrangements described above, offsetting element 24 may include at least one convex portion 32 and a pair of concave portions 34. In an unlocked configuration, as shown in FIG. 8B, prior to insertion of each screw 12 into aperture 16, a first concave portion 34 may be positioned adjacent to a first lateral portion 42 of aperture 16 while a second concave portion 34 may be positioned adjacent to a second lateral portion 42 of aperture 16. Upon movement or rotation of cam head 26 of the offsetting element 24 to the locked or blocked configuration, as shown in FIG. 8A, convex portion 32 may be positioned adjacent one of the inwardly protruding portions 44 of aperture 16 while concave portions 34 are positioned away or spaced from inwardly protruding portions 44. Thus, as shown in FIG. 8A, convex portion 32 protrudes into first and second lateral portions 42. In such a manner, a single offsetting element 24 may be used to simultaneously move two separate screws 12 positioned in a single aperture 16. Alternatively, as shown in FIG. 9, a pair of offsetting elements 24 may be positioned, each so as to cooperate with one of the pair of lateral portions 42. In such a manner, each screw 12 may be moved toward the locked or blocked configuration independently of one another.

Figure 10:
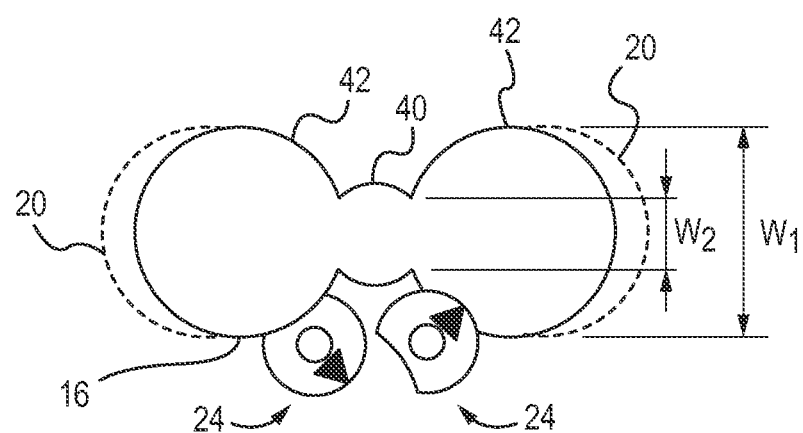
Figure 11:
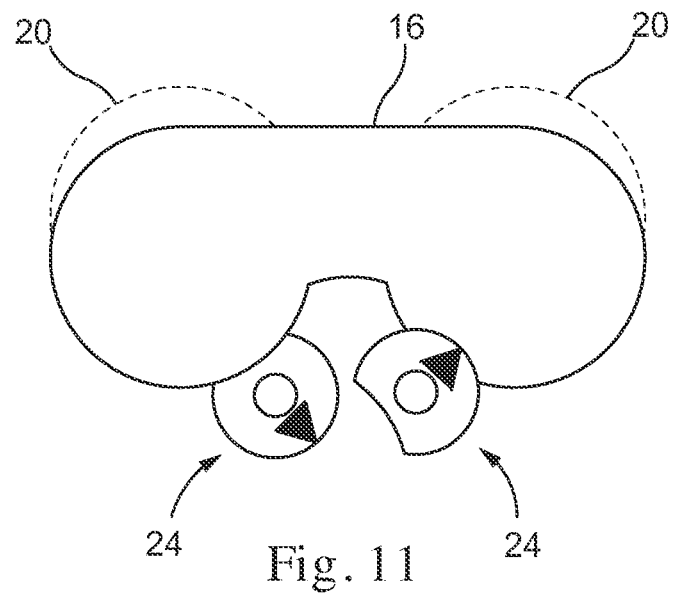

In some arrangements, as shown in FIG. 10, aperture 16 may define a bulbous shape. Similar to aperture 16 described in connection with FIGS. 8A, 8B, and 9, aperture 16 of FIG. 10 may have a variable width. That is, aperture 16 may include two lateral portions 42 having a first width w1 and a central portion 40 have a second width w2. Width w2 may be relatively smaller than width w1. That is, central portion 40 may be a generally narrowed portion of aperture 16, while the two lateral portions 42 may be configured to receive a respective screw 12 therein. As shown in FIG. 10, a separate offsetting element 24 may be positioned adjacent each lateral portion 42. In such a manner, each screw 12 may be moved toward the locked or blocked configuration independently of one another. Alternatively, a single offsetting element 24 may be positioned adjacent one of the pair of inwardly protruding surfaces 44. In such a manner, each screw 12 may be moved toward the locked or blocked configuration simultaneously by a single offsetting element 24.

Figure 12:
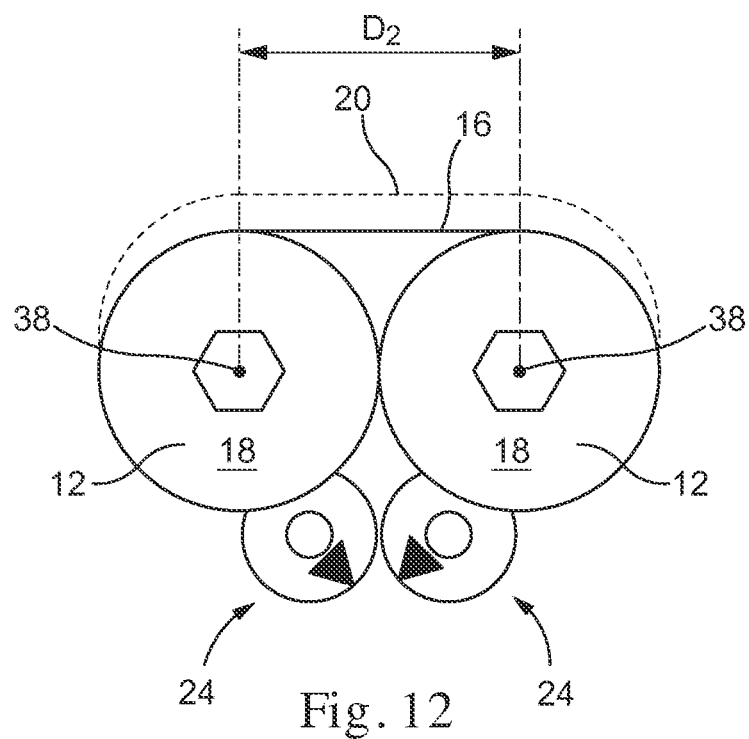

As described above, and as shown in FIG. 11, similar to FIGS. 6A and 6B, a single aperture 16 may be configured (e.g., sized) to receive two screws 12. Additionally, aperture 16 may define two individual and separate recesses 20. However, in some arrangements, as shown in FIG. 12, aperture 16 may define a single recess 20. In such an arrangement, each screw 12 within aperture 16 may be received within a portion of the same recess 20. That is, recess 20 may be elongated, extended, or otherwise sized so as to receive both screws 12 therein.

As shown in FIG. 12, for example, one or more offsetting elements 24 may be associated with each screw 12. Each offsetting element 24 may be similar in construction and manner of use as described above in connection with FIGS. 3A-3C. Due to the inclusion of a separate offsetting element 24 associated with each screw 12, each screw 12 may be moved towards the locked or blocked configuration, as shown in FIG. 12, independently of one another even though both screws 12 may be received in a common recess 20. Alternatively, each screw 12 may be moved towards the locked or blocked configuration simultaneously. That is, rather than two offsetting elements 24, a single offsetting element 24 may be associated with aperture 16. Additionally, as shown in FIG. 12, head 18 of each screw 12 may be positioned within aperture 16 such that a side surface of each screw head 18 abuts one another. That is, as shown in FIG. 12, central longitudinal axes 38 of each screw 12 may be spaced from one another at a distance of D2. Distance D2 may be such that a very small or no gap G is provided between adjacent side surfaces of screws 12.

Figure 13A:
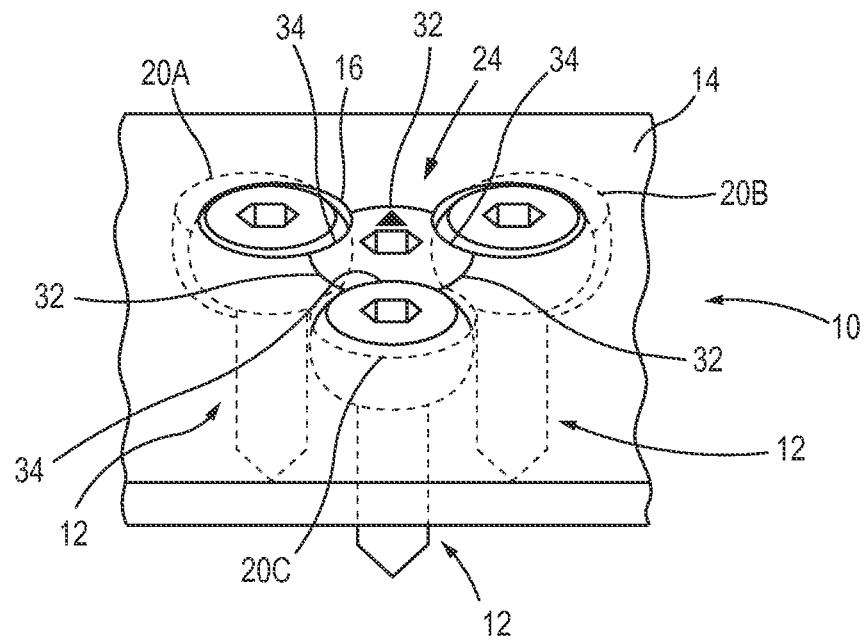
FIGS. 13A and 13B illustrate a still further exemplary screw blocking mechanism.
Figure 13B:
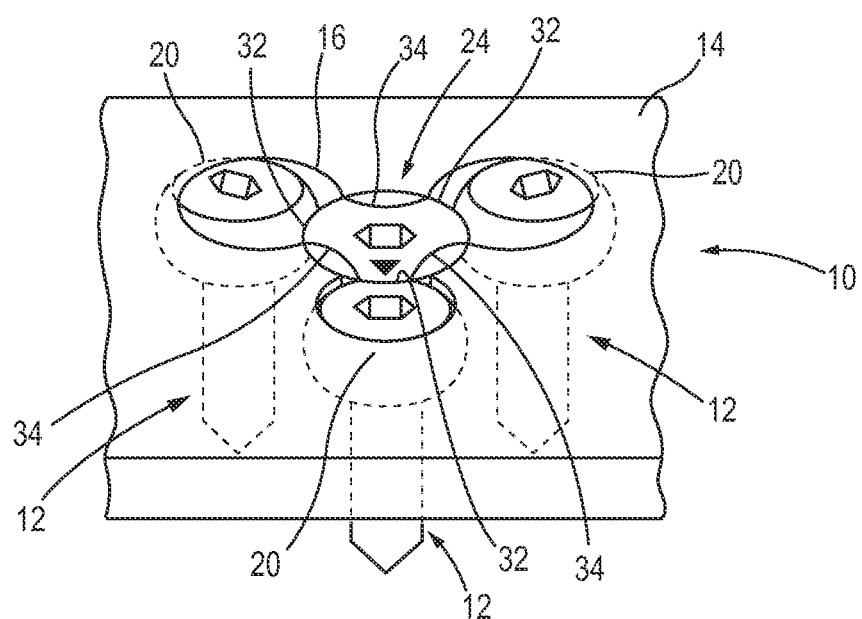

As noted above, each aperture 16 may be configured to receive one or more screws 12 therein. For example, as shown in FIGS. 13A and 13B, a single aperture 16 may be configured (e.g., sized) to receive three screws 12. That is, aperture 16 may be shaped so as to receive three screws 12. While aperture 16 depicted in FIGS. 13A and 13B includes a generally triangular shape having rounded apices, any other appropriate shape configured to receive three screws 12 therein may be used, as will be described in further detail below.

Additionally, while the arrangement of FIGS. 13A and 13B depict a single aperture 16, aperture 16 may define three individual and separate recesses 20. For example, a first recess 20A may be positioned along a first portion of aperture 16, a second recess 20B may be positioned along a second portion of aperture 16, and a third recess 20C may be positioned along a third portion of aperture 16. Each recess 20 may be configured to receive a single screw 12 of the three screws 12. Additionally, similar to the arrangement of FIGS. 5A and 5B, a single offsetting element 24 may be positioned so as to cooperate with and assist in retaining each of the three screws 12. Accordingly, in such an arrangement, offsetting element 24 may be provided at a center of aperture 16 and may include three convex portions 32 radially interspersed between three concave portions 34, as shown. In an unlocked configuration, as shown in FIG. 13A, a first concave portion 34 may be positioned adjacent to a first screw, a second concave portion 34 may be positioned adjacent a second screw 12, and a third concave portion 34 may be positioned adjacent a third screw 12. Further, each of the convex portions 32 may be positioned away or spaced from screws 12. Upon movement or rotation of cam head 26 of the offsetting element 24 to the locked or blocked configuration, as shown in FIG. 13B, convex portions 32 are positioned adjacent apertures screws 12 while concave portions 34 are positioned away or spaced from screws 12. In such a manner, a single offsetting element 24 may be used to simultaneously move and help retain three separate screws 12 positioned in aperture 16.

Figure 14A:
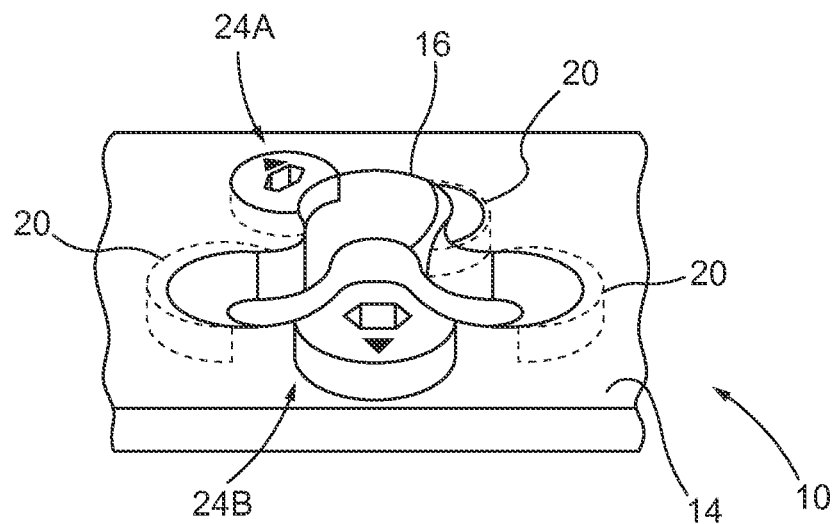
FIGS. 14A and 14B illustrate another exemplary screw blocking mechanism.
Figure 14B:
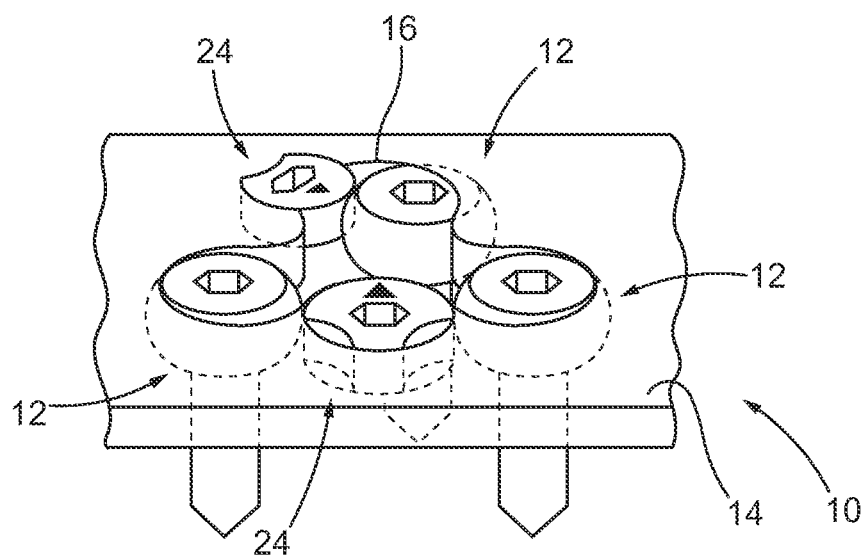

Alternatively, instead of a single offsetting element 24 being included so as to simultaneously move three separate screws 12 positioned in aperture 16, two or more offsetting elements 24 may be arranged relative to aperture 16, as shown in FIGS. 14A and 14B. In such an arrangement, one or more of the three screws 12 may be moved towards the locked or blocked configuration independently of the remaining screws 12. For example, as shown in FIG. 14A, two offsetting elements 24 may be arranged relative to aperture 16. That is, a first offsetting element 24A may be positioned adjacent a first screw 12 while a second offsetting element 24B may be positioned between the remaining two screws 12. In such a manner, the first screw 12 may be moved towards the locked or blocked configuration independently of the second and third screws 12. Further, the second and third screws 12 may move simultaneously with one another while independent of the first screw 12 towards the locked or blocked configuration. Alternatively, three separate and distinct offsetting elements 24 may be positioned relative to aperture 16 such that each offsetting element 24 may be configured to cooperate with a single screw 12 of the three screws 12. In such a manner, each screw 12 may be moved independently of the other screws 12.

Figure 15:
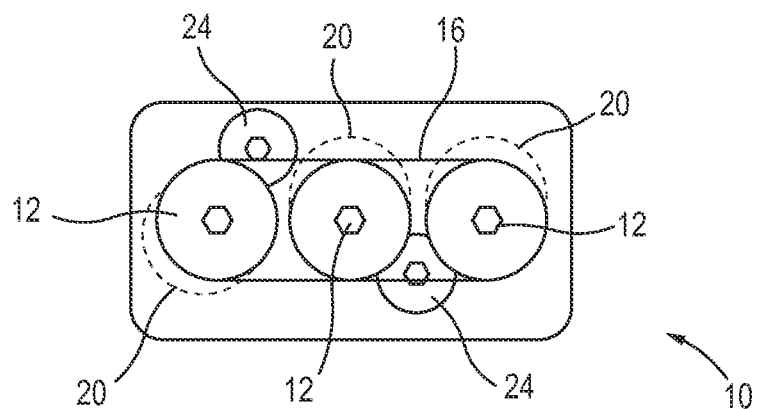
FIGS. 15 and 16 illustrate exemplary screw blocking mechanisms according to further arrangements.
Figure 16:
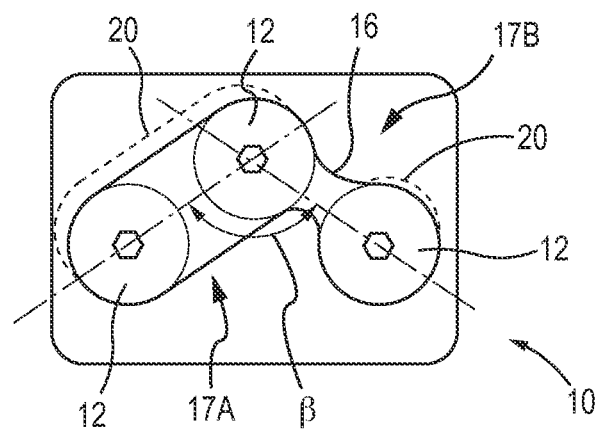

FIGS. 15 and 16 illustrate various modifications and arrangements of illustrative examples in accordance with this disclosure. For example, as shown in FIG. 15, the substrate of interbody device 10 may define a generally ovular or elongated aperture 16. As shown, aperture 16 may define three separate recesses 20, each configured to receive a single screw 12 therein. Accordingly, rather than in a generally triangular configuration as shown in FIGS. 13A, 13B, 14A, and 14B, aperture 16 may receive three screws 12 in a generally linear pattern. Further, as shown, two or more offsetting elements 24 may be arranged along aperture 16. In such an arrangement, one or more of the three screws 12 may be moved towards the locked or blocked configuration independently of the others. For example, as shown in FIG. 15, two offsetting elements 24 may be arranged along aperture 16. That is, a first offsetting element 24 may be positioned adjacent a first screw 12 while a second offsetting element 24 is positioned between the remaining two screws 12 of the three screws 12. In such a manner, the first screw 12 may be moved towards the locked or blocked configuration independently of the second and third screws 12. Further, the second and third screws 12 may move simultaneously with one another towards the locked or blocked configuration and independently of the first screw 12.

Alternatively, as shown in FIG. 16, the substrate of interbody device 10 may define a generally non-linear aperture 16. For example, in the arrangement of FIG. 16, aperture 16 may have a generally L-shaped configuration. That is, aperture 16 may include two segments 17A and 17B extending along intersecting axes. In some arrangements, an angle β between segments 17A and 17B may be about 90°. Those skilled in the art will understand that angle β may be any appropriate angle. Accordingly, angle β may be any value greater or less than 90°. As shown, aperture 16 may define two separate recess 20. A first recess 20 may be configured to receive two screws 12 therein while a second recess may be configured to receive a single screw 12 therein. Further, two or more offsetting elements 24 (not shown) may be arranged along aperture 16. In such an arrangement, one or more of the three screws 12 may be moved towards the locked or blocked configuration independently of the others, as discussed above.

Figure 17:
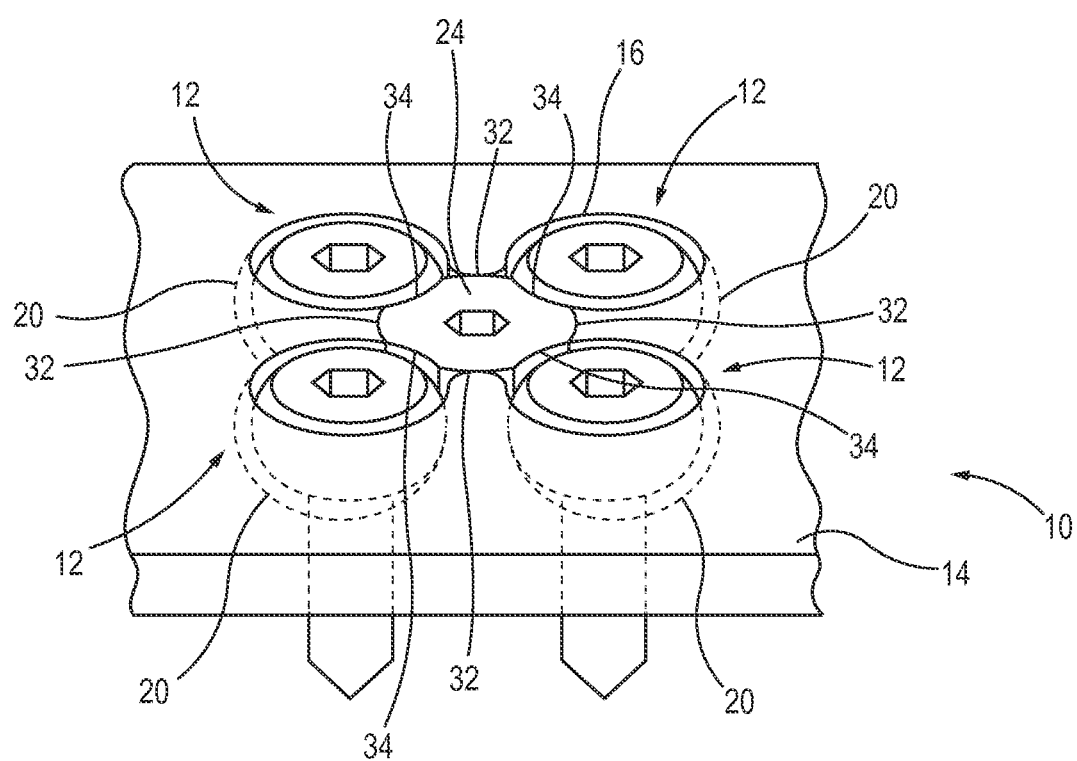
FIG. 17 illustrates yet another exemplary screw blocking mechanism.

In a further example, as shown in FIG. 17, aperture 16 may be configured to receive four screws 12 therein. That is, as shown in FIG. 17, a single aperture 16 may be configured (e.g., sized) to receive four screws 12. While aperture 16 depicted in FIG. 17 includes a generally square and/or rectangular configuration with rounded corners, any other appropriate shape configured to receive four screws 12 therein may be used, as will be described in further detail below.

Additionally, while the arrangement of FIG. 17 depicts a single aperture 16, aperture 16 may define four individual and separate recesses 20. For example, a first recess 20 may be positioned along a first portion of aperture 16, a second recess 20 may be positioned along a second portion of aperture 16, a third recess 20 may be positioned along a third portion of aperture 16, and a fourth recess 20 may be positioned along a fourth portion of aperture 16. Each recess 20 may be configured to receive a single screw 12 of the four screws 12. Additionally, similar to the arrangement of FIGS. 13A and 13B, a single offsetting element 24 may be positioned so as to cooperate with and engage each of the four screws 12. Accordingly, in such an arrangement, offsetting element 24 may be provided at a center of aperture 16 and may include four convex portions 32 interspersed with four concave portions 34 along an outermost radial surface of offsetting element 24, as shown. In an unlocked configuration, as shown in FIG. 17, a first concave portion 34 may be positioned adjacent to a first screw, a second concave portion 34 may be positioned adjacent a second screw 12, a third concave portion 34 may be positioned adjacent a third screw 12, and a fourth concave portion 34 may be positioned adjacent a fourth screw 12. Further, each of the convex portions 32 may be positioned away or spaced from screws 12. Upon movement or rotation of cam head 26 of the offsetting element 24 to the locked or blocked configuration (not shown), convex portions 32 are positioned adjacent screws 12 while concave portions 34 are positioned away or spaced from screws 12. In such a manner, a single offsetting element 24 may be used to simultaneously engage and retain four separate screws 12 positioned in aperture 16.

Alternatively, instead of a single offsetting element 24 being included so as to simultaneously move or otherwise bias four separate screws 12 positioned in aperture 16, two or more offsetting elements 24 may be arranged about aperture 16. In such an arrangement, one or more of the four screws 12 may be moved towards the locked or blocked configuration independently of the others.

Figure 18:
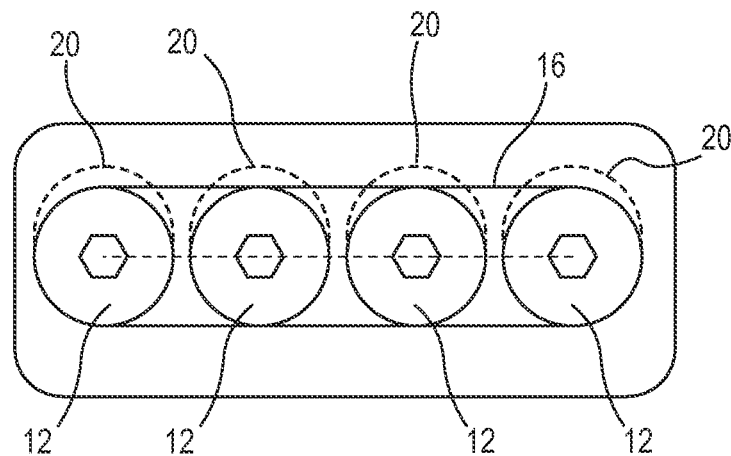
FIGS. 18-21 illustrate exemplary screw blocking mechanisms according to further arrangements for use with multiple screws in a single bore.
Figure 19:
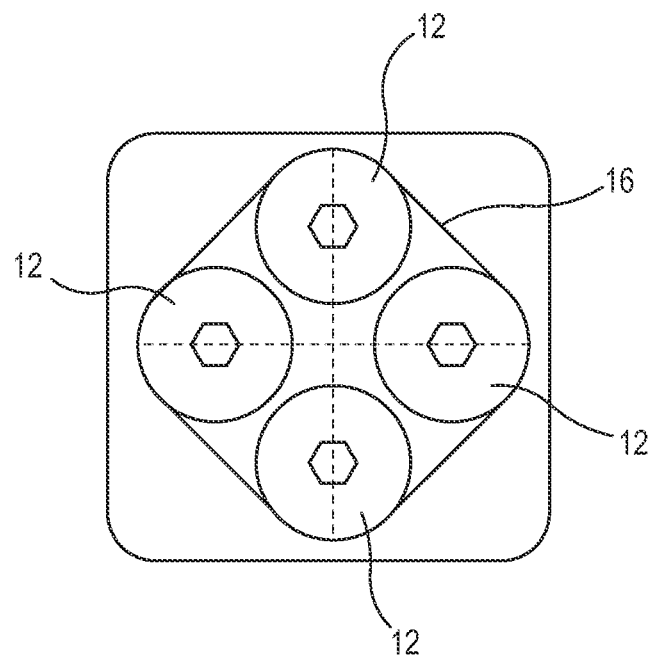
Figure 20:
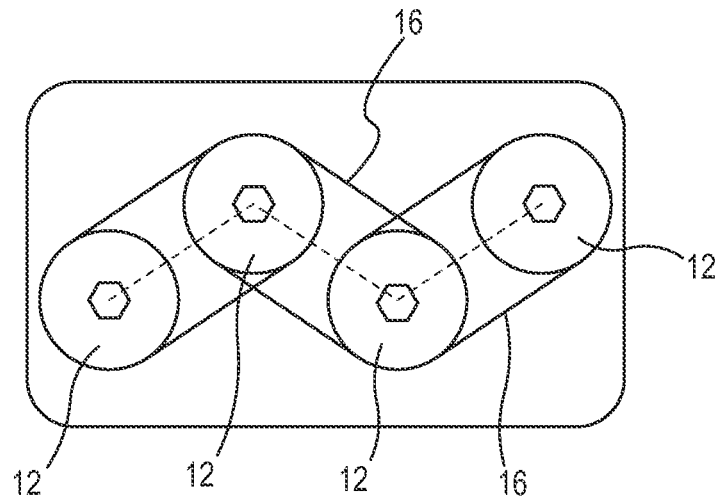
Figure 21:
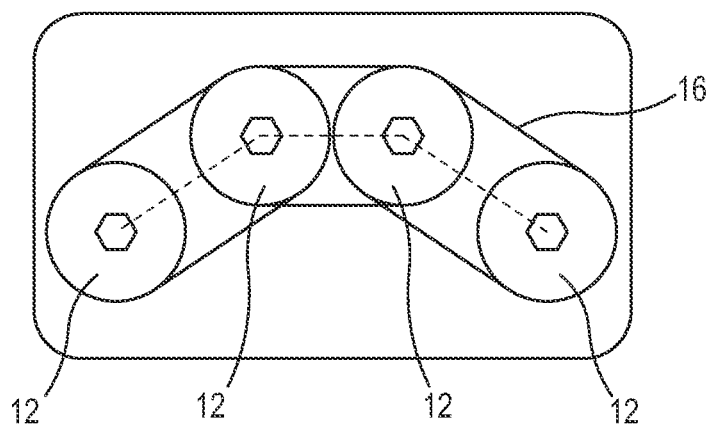

FIGS. 18-21 illustrate various modifications and arrangements of illustrative examples in accordance with this disclosure. For example, as shown in FIG. 18, the substrate of interbody device 10 may define a generally ovular or elongated aperture 16. As shown, aperture 16 defines four separate recess 20, each configured to receive and retain a single screw 12 therein. Accordingly, instead of the generally square or rectangular configuration of FIG. 17, aperture 16 may receive four screws 12 in a generally linear pattern. As shown, the substrate of interbody device 10 as depicted in FIG. 18 may include four separate and distinct recesses 20, each recess configured to receive a respective one of four screws 12. However, as noted above, any appropriate number of recesses 20, such as 1, 2, 3, or 4, may be used. Though FIG. 18 depicts each of the four recesses 20 on a single side of aperture 16, one or more of the recess 20 may be positioned along any of the other sides of aperture 16. Additionally, although not shown in FIG. 18, any appropriate number of offsetting elements 24 may be arranged along aperture 16 so as to move one or more screws 12 towards the locked or blocked configuration. Alternatively, aperture 16 may have any appropriate shape and/or rotational arrangement. For example, FIG. 19 depicts a generally square-shaped aperture 16 having rounded corners, similar to FIG. 17, but rotated approximately 45°. Accordingly, aperture 16 may be arranged such that screws 12 may be received along any desired position. Additionally, FIG. 20 illustrates a generally sinusoidally-shaped aperture 16, and FIG. 21 illustrates a generally non-collinear shaped aperture 16. Although not shown in FIGS. 19-21, any appropriate number of recesses 20 and offsetting elements 24 may be associated with each aperture 16 so as to move each of the four screws 12 towards the locked or blocked configuration.

Figure 22A:
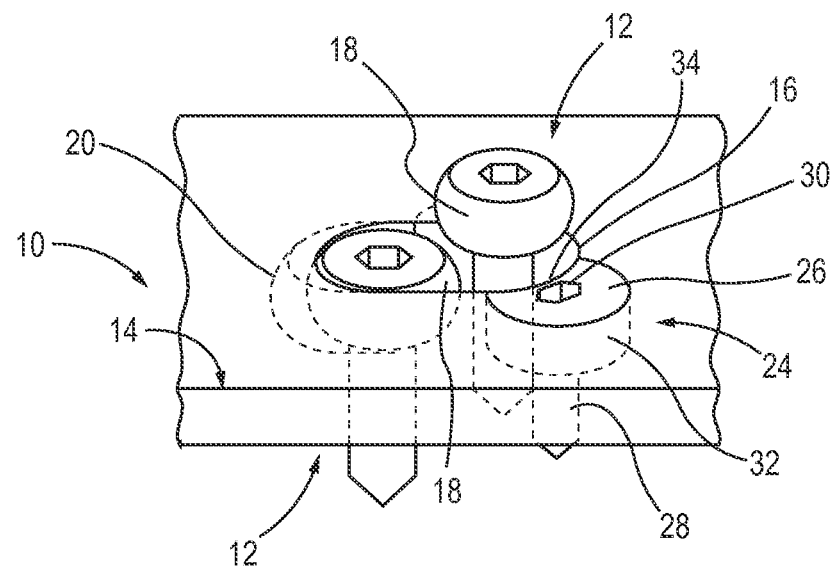
FIGS. 22A-22D illustrate another exemplary screw blocking mechanism.

A further exemplary system for preventing fixation devices such as screws 12 from backing out (e.g., unscrewing) and/or dislodging from interbody device 10 is shown in FIGS. 22A-22D. Similar to the arrangements described above, an exemplary interbody device 10 may include a first face 14 defining an aperture 16 configured to receive one or more screws 12 therein. For example, as shown in FIG. 22A, aperture 16 may be configured to receive two screws 12 therein. Aperture 16 may have any appropriate shape configured to receive screws 12 therein. For example, as shown in FIG. 22A, aperture 16 may be generally elongated with rounded corners. Similar to the arrangements described above, and as shown in FIG. 22B, aperture 16 may include one or more recesses 20 configured to cooperate with and/or correspond in profile with head 18 of screw 12, so as to retain screw 12 within aperture 16. For example, as shown, aperture 16 may include two recesses 20, each recess 20 including a pocket or space into which head 18 of one of the two screws 12 may be moved upon the application of a lateral force. One of the recesses 20 may be disposed at a first location along aperture 16, and the other recess 20 may be disposed at a second location along aperture 16.

As shown, the substrate of interbody device 10 may further include an offsetting element 24 similar to those described above. As shown in FIG. 22A, offsetting element 24 may be positioned adjacent aperture 16 so as to cooperate with head 18 to prevent screw 12 from backing out (e.g., unscrewing) or dislodging from interbody device 10. Further, offsetting element 24 may be movably received within the substrate of interbody device 10. For example, in some arrangements, offsetting element 24 may be rotatably received within the substrate of interbody device 10.

As shown in FIG. 22A, offsetting element 24 may include a cam head 26 coupled to a shaft 28. Shaft 28 may extend into the substrate of interbody device 10 and include any appropriate threading or similar retention mechanism (not shown) configured to movably couple offsetting element 24 to interbody device 10. Accordingly, interbody device 10 may include an internally threaded bore for cooperation with shaft 28. Cam head 26 may include an actuator receiving element such as, for example, a hex-shaped bore 30 configured to cooperate with any appropriate rotatable driver (e.g., key, screw driver, hex driver, etc.). While bore 30 is described and illustrated as a hex-shaped bore 30, it is understood that any appropriate shaped bore may be used so as to cooperate with any correspondingly shaped driver and/or driver tip. Cam head 26 may be eccentrically and/or irregularly shaped. For example, as shown, cam head 26 may include a crescent-shaped member have a convex portion 32 and a concave portion 34. In an unlocked configuration, as shown in FIG. 22A, concave portion 34 may be positioned adjacent to aperture 16 while convex portion 32 is positioned away or spaced from aperture 16. Upon movement or rotation of cam head 26 to a locked or blocked configuration (FIG. 22D), convex portion 32 is positioned adjacent aperture 16 while concave portion 34 is positioned away or spaced from aperture 16.

Figure 22B:
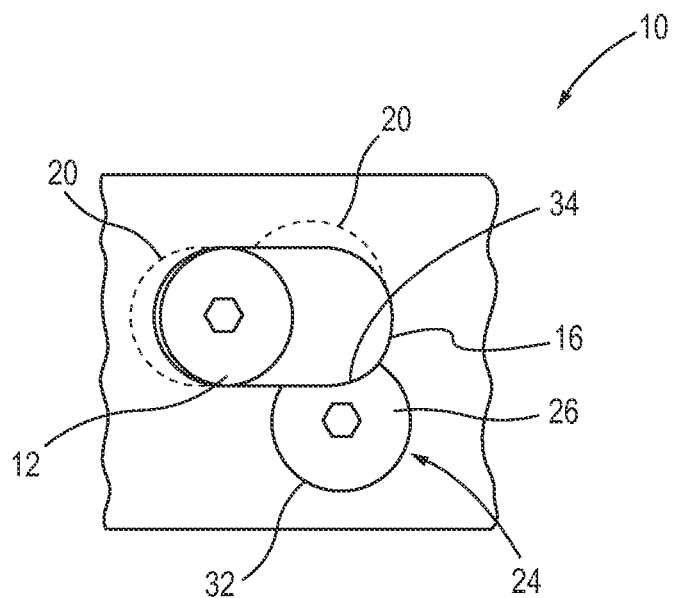
Figure 22C:
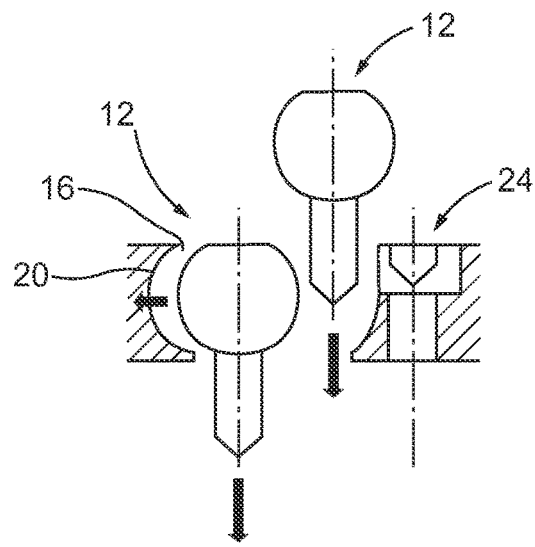
Figure 22D:
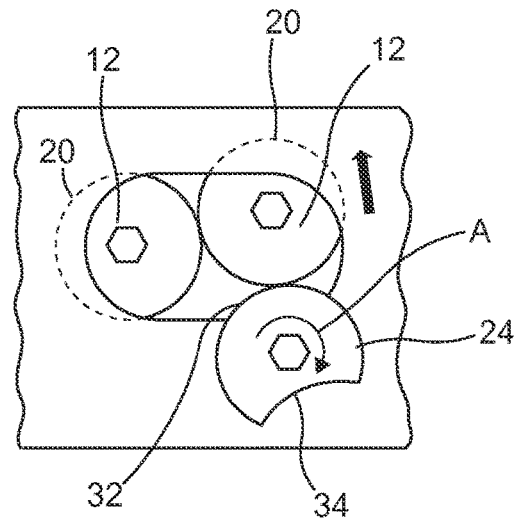

FIGS. 22B-22D illustrate an exemplary manner of preventing screws 12 from backing out (e.g., unscrewing) and/or dislodging from interbody device 10. For example, FIG. 22B illustrates interbody device 10 and offsetting element 24 in the unlocked configuration. Accordingly, a first screw 12 may be disposed into aperture 16, at a location distant or spaced from offsetting element 24, as shown in FIG. 22B. Next, as shown in FIG. 22C, second screw 12 may be inserted into aperture 16. As shown, upon the insertion of second screw 12, first screw 12 may be urged or otherwise biased laterally toward a first recess 20. That is, interference between the first screw 12 and the second screw 12 may cause first screw 12 to be displaced laterally such that head 18 of first screw 12 is received within or otherwise biased towards a first recess 20. Upon rotation of offsetting element 24, for example, in direction A as shown in FIG. 22D, cam head 26 of offsetting element 24 may be rotated such that convex portion 32 may be brought in contact with a side surface of head 18 of the second screw 12. As such, the second screw 12 may be pushed, moved, urged, or otherwise urged laterally toward the second recess 20 and the external side and/or top surface of head 18 of screw 12 may be received within recess 20. Accordingly, in the locked or blocked configuration, as shown in FIG. 22D, offsetting element 24 may be configured to retain screw 12 in interbody device 10.

It is to be understood, that any one or more of the previously disclosed features of interbody device 10 may be used together or separately. For example, the substrate of interbody device 10 may define one or more apertures 16 therein. Each aperture may be configured (e.g., sized) to fit one or more screws 12 therein. Additionally, each aperture 16 may include one or more recesses 20 therein. That is, in some arrangements, a single recess 20 may be configured to receive one or more screws 12 therein. Additionally, as noted above, any appropriate configuration of aperture(s) may be provided. For example, in some arrangements, aperture(s) 16 may have a substantially constant width. As used herein, the terms "about," "substantially," and "approximately," may indicate a range of values within +/−5% of a stated value. Alternatively, in some arrangements, aperture(s) may have a varied width. Additionally, aperture(s) 16 may be arranged in a linear, nonlinear, and/or symmetrical configurations. In some arrangements, aperture(s) 16 may be arranged in a general oval, triangle, and/or square configuration. Additionally, in examples in which multiple screws 12 are received within a single aperture 16, aperture 16 may be configured such that a gap G is provided between adjacent side surfaces of screws 12, or alternatively, such that no gap G is provided between adjacent side surfaces of screws 12. Further, as discussed above, in any disclosed arrangement, one or more offsetting elements 24 may be arranged along aperture(s) 16 at any suitable location. In some arrangements, a single offsetting element 24 may be provided to assist in retaining one, two, three, four, or more screws 12 from the unlocked configuration to the locked or blocked configuration simultaneously. Alternatively, multiple offsetting elements 24 may be provided such that one or more screws 12 may be independently moved from the unlocked configuration to the locked or blocked configuration.

Screws 12 may have any appropriate geometry and/or configuration. For example, head 18 of each screw 12 may be either a fixed-angle screw head or variable-angle screw head depending on the required conical angulation of screw 12. For example, in some arrangements, the conical angulation of screw 12 may be between about 0° and 20°. In some arrangements, the conical angulation of screw 12 may be about 15°. Additionally, screws 12 may be either self-drilling or self-tapping. Screws 12 may have any appropriate thread length and thread diameter. For example, screws 12 may have a thread length between about 8 mm and 65 mm. That is, screws 12 may have a thread length between about 8 mm and 25 mm, between about 15 mm and 45 mm, and/or about 25 mm and 65 mm. Screws 12 may have a thread diameter between about 3 mm and 6.5 mm. For example, screws 12 may have a thread diameter between about 3 mm and 4.5 mm, and/or between about 4.5 mm and 6.5 mm.

Interbody Device Structure and Features

FIGS. 23-32 schematically illustrate various configurations of exemplary interbody devices 10 (e.g., a cage, spacer, and/or block). Indeed, FIGS. 23-27 illustrate exemplary standalone interbody devices 10 and FIGS. 28-32 illustrate exemplary composite interbody devices 10. Standalone interbody devices 10 may include any structure configured to accept screws 12 directly therethrough, whereas composite interbody devices 10 may include any combination of a plate and spacer/cage, collectively configured to accept screws 12 therethrough.

Figure 23:
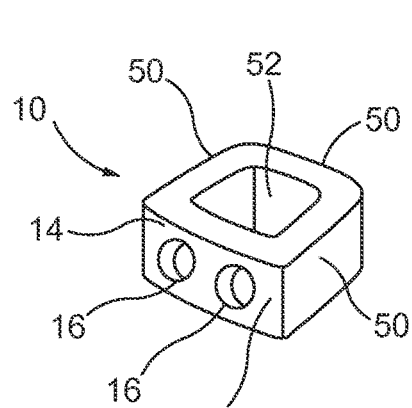
FIGS. 23-27 illustrate exemplary standalone interbody devices.

Standalone interbody devices 10 may include any appropriate configuration. For example, as shown in FIG. 23, interbody device 10 may define a closed cage. That is, interbody device 10 may include a generally rectangular and/or square shape having at least four sides 50. Accordingly, interbody device 10 may define an internal space 52 surrounded on four sides thereof by sides 50. Space 52 may be configured to receive bone graft or other suitable ingrowth promoting material. Additionally, at least one side 50 may define a screw receiving face 14 including one or more apertures 16, as discussed above.

Figure 24:
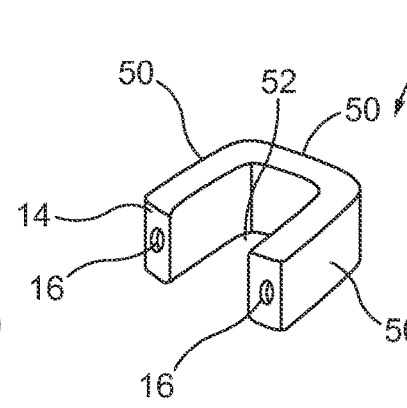
Figure 25:
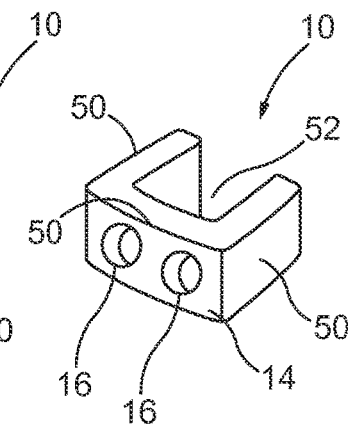
Figure 26:
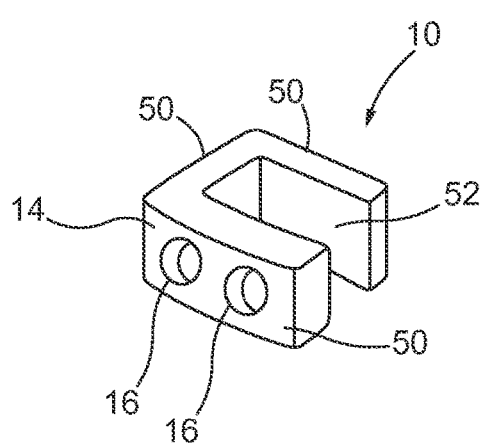
Figure 27:
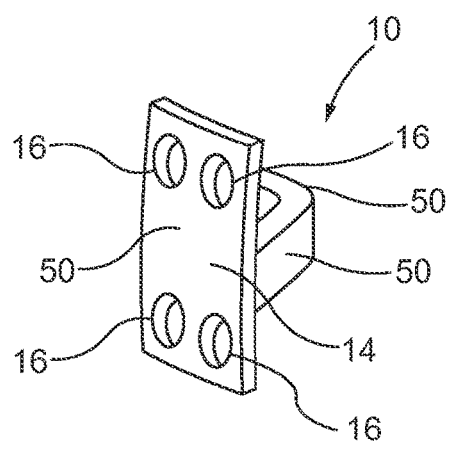

Alternatively, interbody device 10 may define an open cage having three sides 50. For example, in some arrangements, as shown in FIG. 24, interbody device 10 may have an open front and include two lateral sides 50 connected by one rear side 50. In other arrangements, as shown in FIG. 25, interbody device 10 may have an open rear and include two lateral sides 50 connected by one front side 50. Alternatively, as shown in FIG. 26, interbody device 10 may have an open lateral side, and include one lateral side 50, one rear side 50, and one front side 50. In yet a further arrangement, as shown in FIG. 27, interbody device 10 may include a closed cage having an enlarged front side 50. Such an enlarged front side 50 may facilitate placement of screws 12 at varied heights along spinal column 2.

Figure 28:
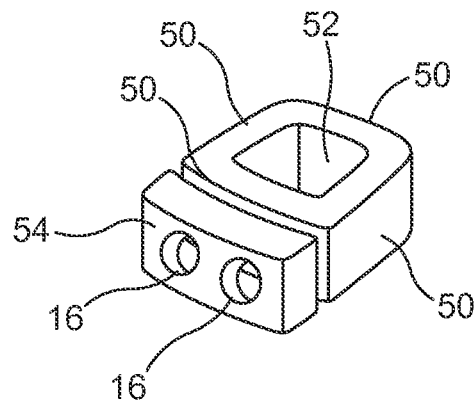
FIGS. 28-32 illustrate exemplary composite interbody devices.

Similar to standalone interbody devices 10, composite interbody devices 10 may include any appropriate configuration. For example, as shown in FIG. 28, interbody device 10 may include a closed cage. That is, interbody device 10 may include a generally rectangular and/or square cage having at least four sides 50 which may define an internal space 52. Additionally, interbody device 10 may include a panel (e.g., plate) 54 defining a screw receiving face 14 including one or more apertures 16, as discussed above. Panel 54 may be coupled to the cage of interbody device 10 via any appropriate manner such as, for example, welding, fusion, adhesives or the like.

Figure 29:
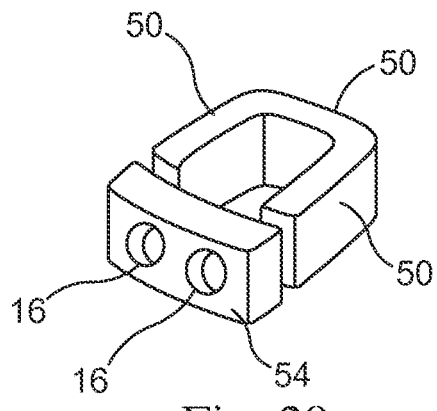
Figure 30:
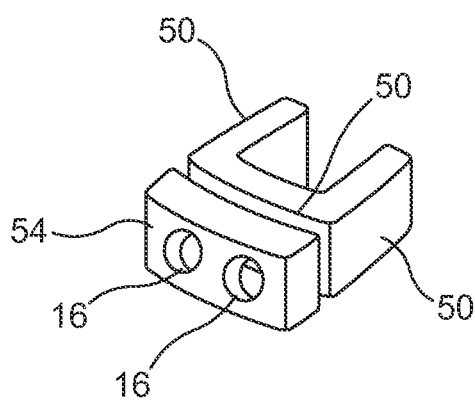
Figure 31:
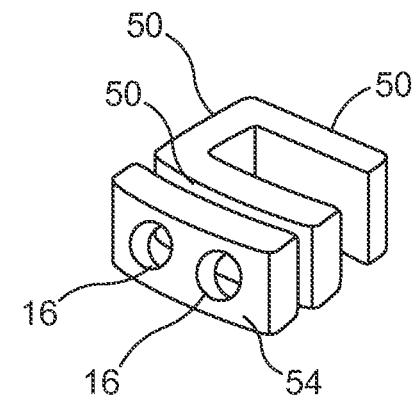
Figure 32:
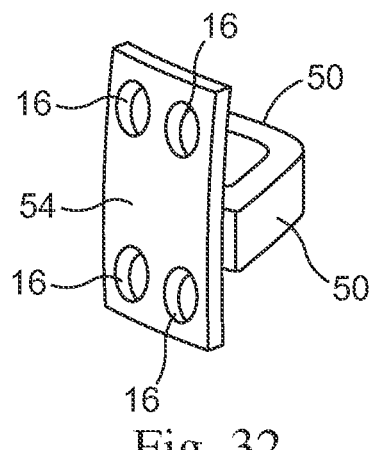

In another arrangement, as shown in FIG. 29, interbody device 10 may define an open cage having three sides. For example, in some arrangements, as shown in FIG. 29, the cage of interbody device 10 may have an open front and include two lateral and one rear side 50. Additionally, interbody device 10 may further include a panel 54 defining a screw receiving face 14 including one or more apertures 16. In other arrangements, as shown in FIG. 30, interbody device 10 may include an open cage having an open rear and two lateral and one front sides 50. Alternatively, as shown in FIG. 31, interbody device 10 may include a cage having an open lateral side, and one lateral, one rear, and one front side 50. In yet a further arrangement, as shown in FIG. 32, interbody device 10 may include an closed cage. Additionally, as shown, panel 54 may be enlarged relative to the cage. Such an enlarged panel 54 may facilitate placement of screws 12 at varied heights along spinal column 2. Exemplary interbody devices 10 may include a homogeneous stainless steel, titanium, chromium, PEEK, and/or combinations thereof. Alternatively, exemplary interbody devices 10 may include a heterogeneous composite such as PEEK embedded with radiopaque mixtures so as to provide different gradients of radio-opacity, as will be described in further detail below. For example, in some arrangements, interbody device 10 may be comprised of a substantially radiolucent material such as PEEK. To enable visual inspection of such an interbody device 10 via X-ray or other such imaging modalities, interbody device 10 may additionally include a pin, screw, or other such member comprised of a radiopaque material. For instance, in some arrangements, such a pin or screw may be comprised of tantalum. Additionally, any one of interbody devices 10 of FIGS. 23-32 may include any of the features noted above. That is, any of interbody devices 10 discussed throughout this disclosure may include any one or more of offsetting elements 24 configured to facilitate locking or blocking one or more screws 12, disposed in one or more aperture 16, from backing out (e.g., unscrewing) and/or dislodging from interbody device 10. Additionally, exemplary interbody devices 10 may be solid, or in some arrangements, may be formed through any appropriate manufacturing method so as to be generally porous while remaining structurally strong. For example, in arrangements, one or more portion of interbody device 10 may be thinned or reduced in profile.

Figure 33:
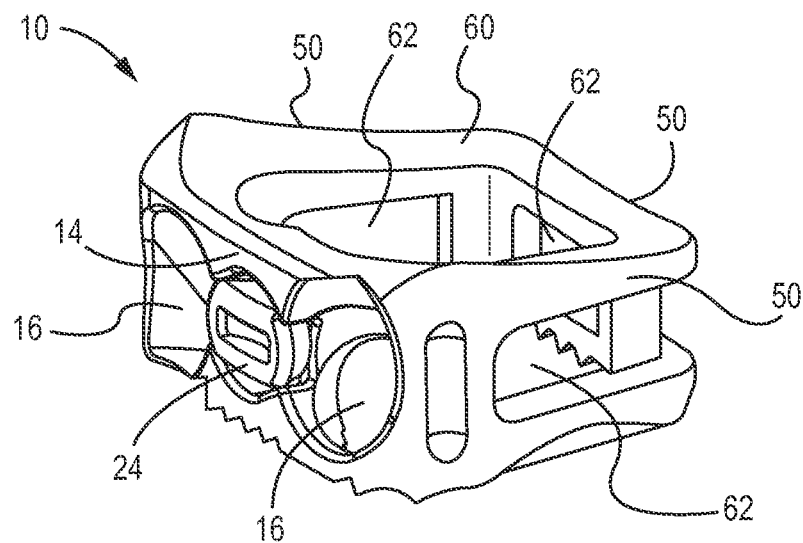
FIGS. 33 and 34 illustrate a perspective and side view of an exemplary interbody device, respectively.

For example, as shown in FIG. 33, interbody device 10 may include a face 14 defining two apertures 16 and having an offsetting element 24 (or any other screw blocking mechanism) therebetween. Offsetting element 24 may be similar in construction and manner of use as described above. Further, various arrangements of interbody devices 10 may include one or more features configured to facilitate sagittal and/or coronal visibility. For example, a body or frame 60 of interbody device 10 may comprise a radiopaque material visible via x-ray or similar forms of imaging modalities. As such, frame 60 may enable accurate positioning and/or placement of interbody device 10 within and/or along spinal column 2. Frame 60 may include any one or more features such as anti-migration and/or anchoring features, anti-rotation features, insertion tool features, reduced profile keel features, and the like, as will be described in further detail below.

Figure 34:
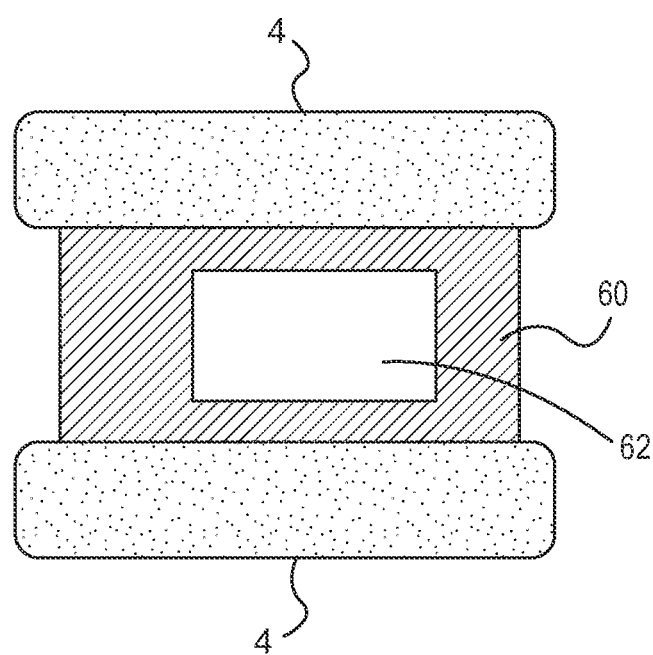

Additionally, frame 60 may define one or more openings and/or windows 62. Such windows 62 may remain empty and/or may be filled with radiolucent material such as tissue grafts as will be described in further detail below. Window(s) 62 may enable a medical professional to view and/or determine the level of post-operative fusion between interbody device 10 and patient bone and/or tissue. Frame 60 may define any appropriate arrangement, number, and configuration of window(s) 62. That is, as shown in FIG. 33, for example, interbody device 10 may comprise a standalone device having a closed cage, similar to the arrangement of FIG. 23. As shown in FIG. 33, frame 60 may include a single window 62 on each lateral side 50 and rear side 50. Each window 62 may be generally square or rectangular. In some arrangements, a radiolucent structure, such as a graft containment sheath, may be disposed along one or more portions of frame 60, as will be described in further detail below. Indeed, such graft containment sheaths may substantially fill or encompass window 62 of one or more sides 50 of frame 60. Accordingly, in the sagittal view of interbody device 10 placed between two adjacent vertebrae 4 under X-ray vision, as shown in FIG. 34, window 62 remains radiolucent such that fusion within and/or through window 62 may be observed.

Figure 35:
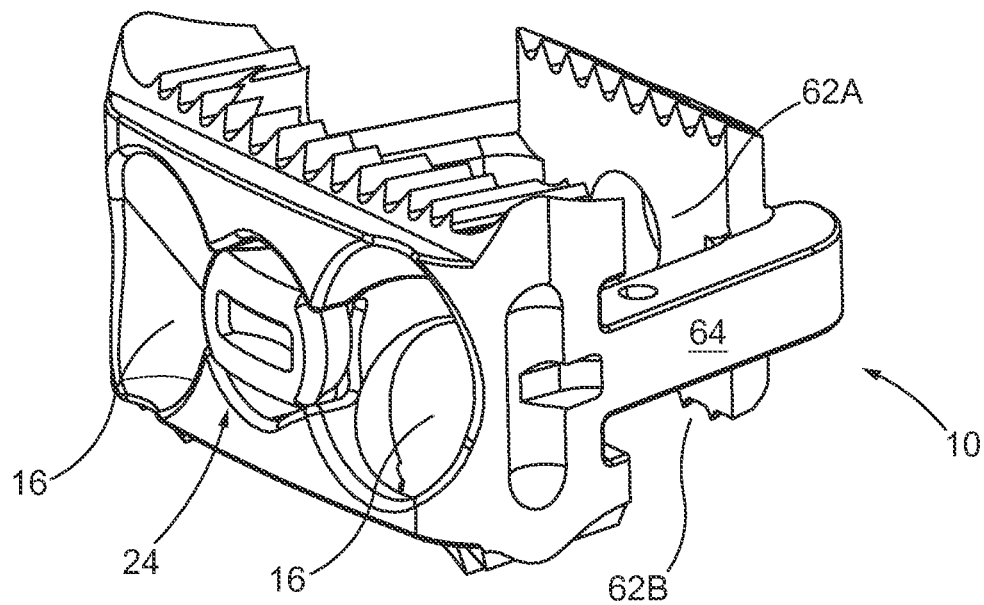
FIGS. 35 and 36 illustrate a perspective and side view of another exemplary interbody device, respectively.
Figure 36:
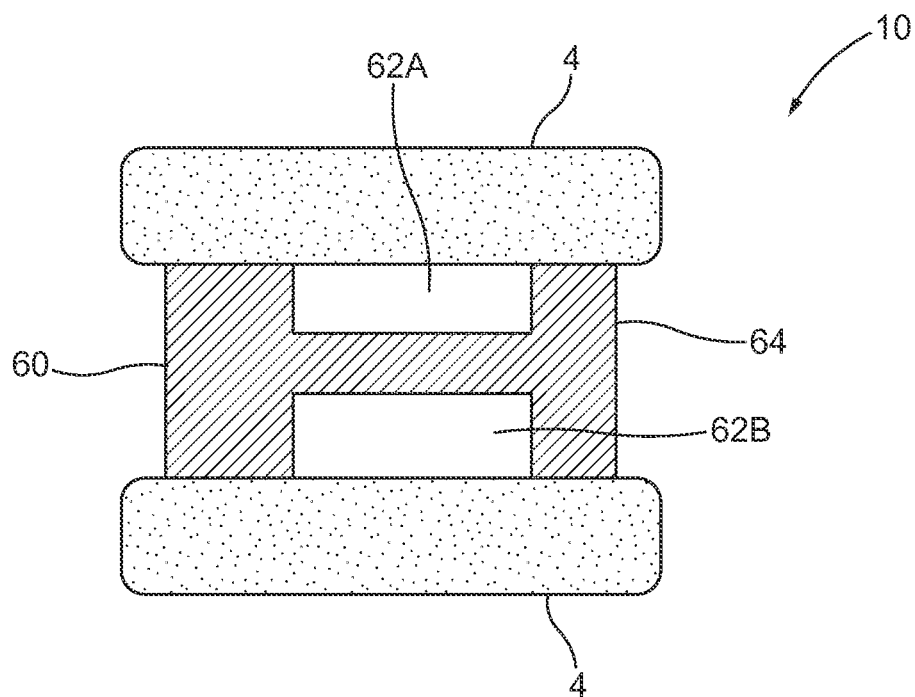

In other arrangements, frame 60 of interbody device 10 may define one or more split windows 62. As shown in FIG. 35, for example, interbody device 10 may comprise a standalone device having a closed cage, similar to the arrangement of FIG. 23. Rather than solid panel lateral sides 50, frame 60 may include lateral supports 64 defining a first (e.g., upper) window portion 62A and a second (e.g., lower) window portion 62B. Accordingly, in the sagittal view of interbody device 10 placed between two adjacent vertebrae 4 under X-ray vision, as shown in FIG. 36, first window portion 62A and second window portion 62B remain radiolucent such that fusion within and/or through first window portion 62A and second window portion 62B may be observed.

Figure 37:
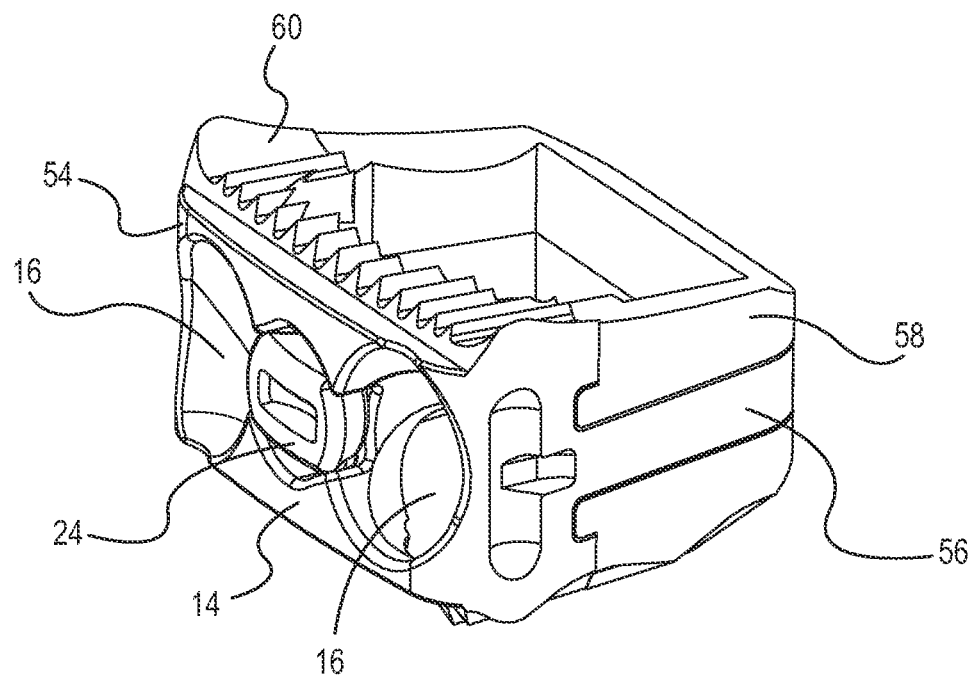
FIGS. 37 and 38 illustrate a perspective and side view of a still further exemplary interbody device, respectively.
Figure 38:
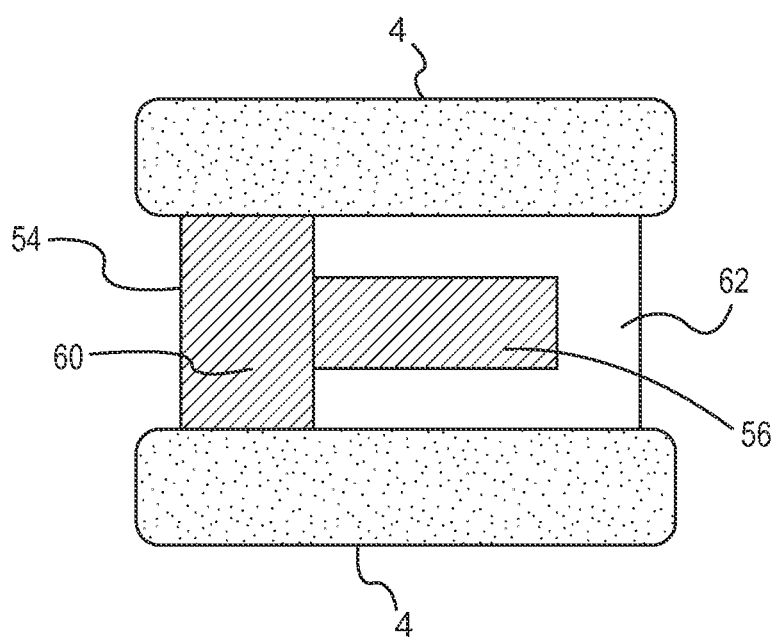

Alternatively, as shown in FIG. 37, a composite interbody device 10 may include a panel 54 defining a screw receiving face 14 including one or more apertures 16, as discussed above. Panel 54 may define a pair of opposed lateral arms 56 extending therefrom. Panel 54 may be coupled to a radiolucent cage portion 58. Cage portion 58 may include any appropriate radiolucent structure configured to maintain a desired spacing between adjacent vertebrae 4. Accordingly, cage portion 58 may be any non-metallic structure extending from panel 54 and may, in some arrangements, include a graft containment sheath, as will be described in further detail below. In the sagittal view of interbody device 10 placed between two adjacent vertebrae 4 under X-ray vision, as shown in FIG. 38, a generally inverted c-shaped window 62 may remain radiolucent such that fusion within and/or through window 62 may be observed.

Figure 39:
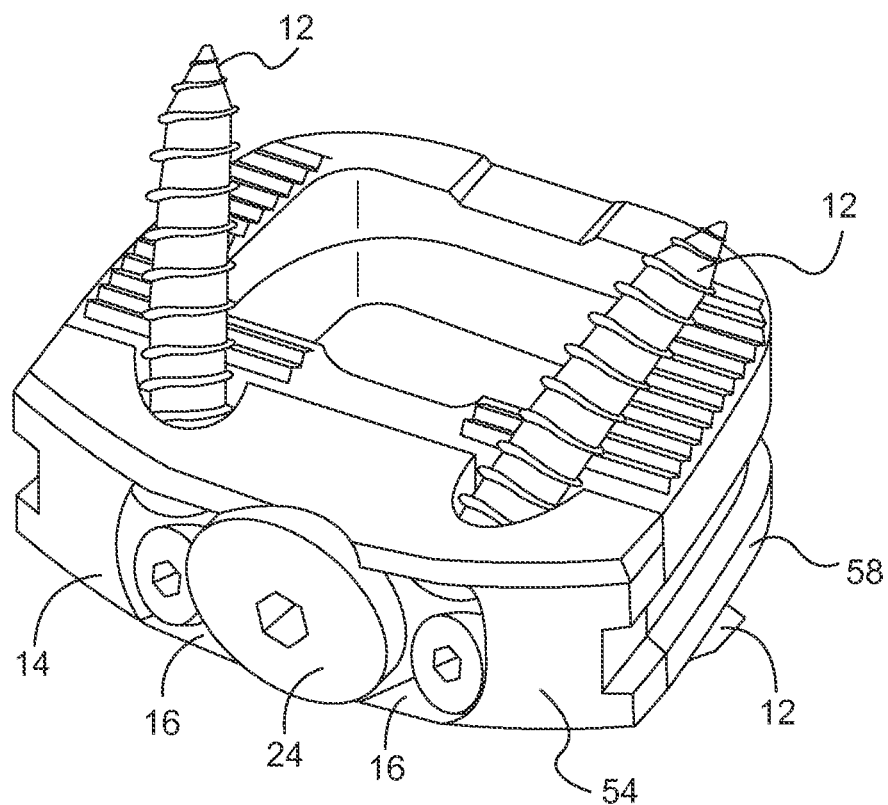
FIGS. 39-41 illustrate a perspective and side views of another exemplary interbody device, respectively.
Figure 41:
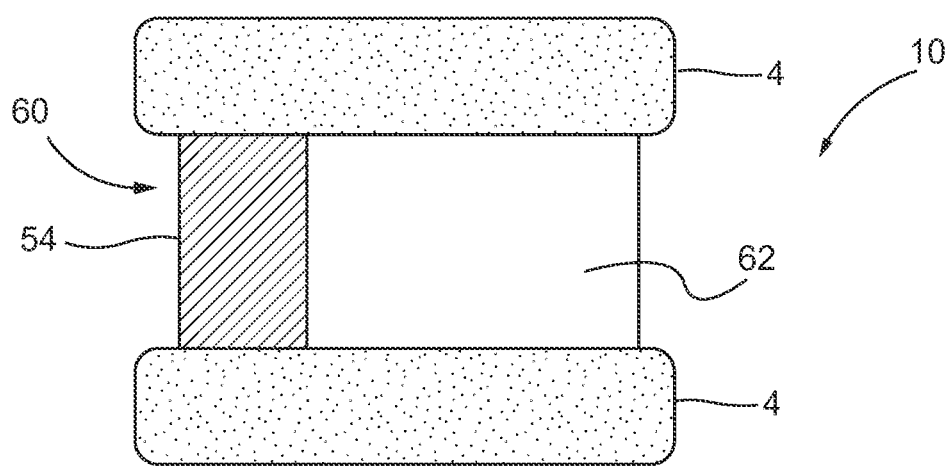
Figure 40:
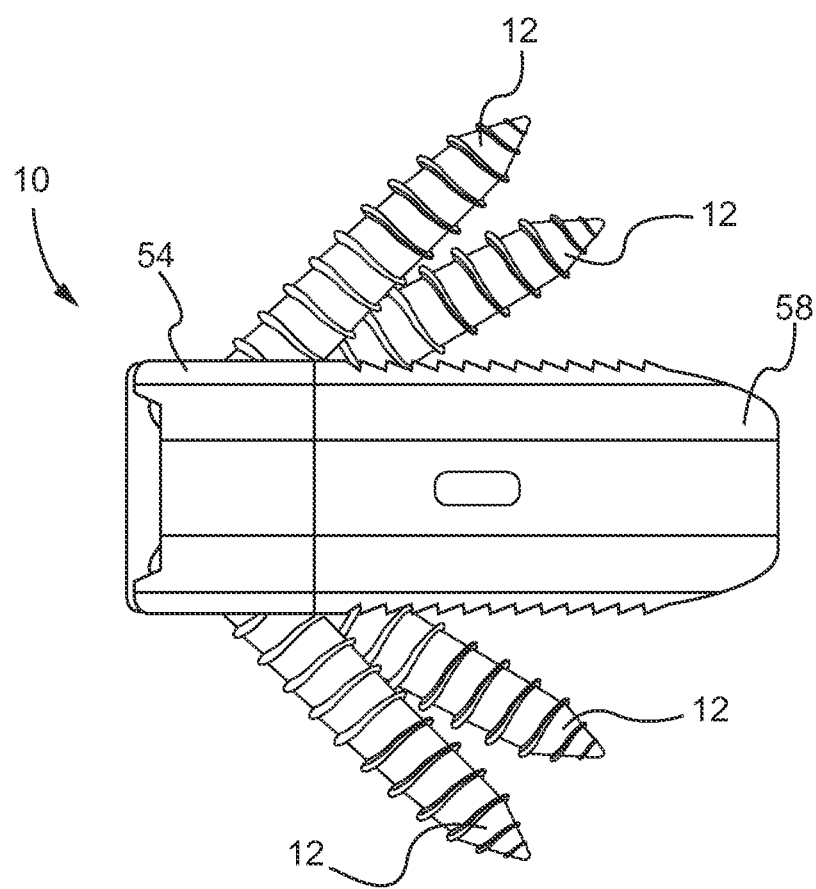

Alternatively, as shown in FIGS. 39-41, a composite interbody device 10 may include a panel 54 defining a screw 12 receiving face 14 including one or more apertures 16 configured to receive a screw 12 (or similar fastener) therein, as discussed above. Panel 54 may be coupled to a radiolucent cage portion 58. Cage portion 58 may include any appropriate radiolucent structure configured to maintain a desired spacing between adjacent vertebrae 4. Accordingly, cage portion 58 may be any non-metallic structure extending from panel 54 and may in some arrangements include a graft containment sheath, as will be described in further detail below. Cage portion 58 may include any appropriate structure, geometry, and/or feature(s) configured to couple with panel 54. In the sagittal view of interbody device 10 placed between two adjacent vertebrae 4 under X-ray vision, as shown in FIG. 41, a generally square and/or rectangle shaped window 62 may remain radiolucent such that fusion within and/or through window 62 may be observed.

Figure 42:
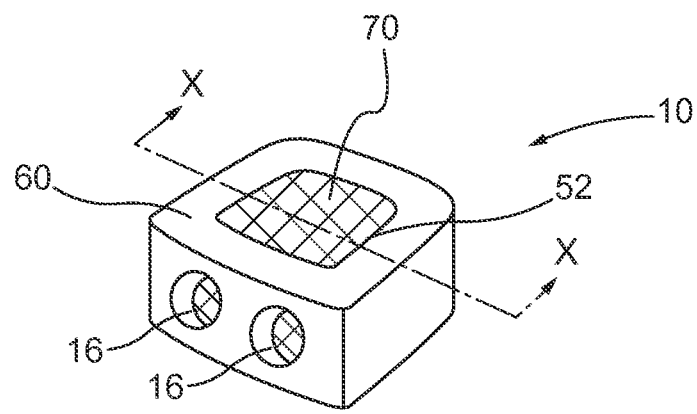
FIG. 42 illustrates an interbody device including packed bone graft material.
Figure 43:
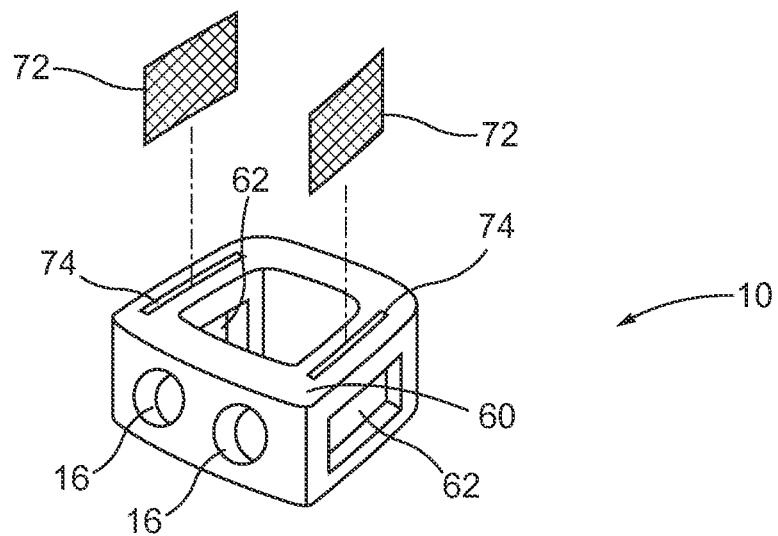
FIG. 43 illustrates an interbody device including at least one retention member.

As discussed above, any of the above noted windows 62, first window portion 62A, and/or second window portion 62B may be filled with radiolucent material such as tissue grafts. That is, as shown in FIG. 42, a representative interbody device 10 may be packed with bone graft. For example, internal space 52 of frame 60 may be filled with packed bone graft material 70. Bone graft material 70 may facilitate bone and tissue ingrowth in and through interbody device 10. Accordingly, bone graft 70 may promote fusion, i.e., the joining of two or more vertebrae 4. However, during placement of interbody device 10 within spinal column 2 and/or manipulation thereafter, bone graft material 70 may become dislodged and/or fall out of interbody device 10 via the windows 62. Additionally, inclusion of one or more windows 62 may further enable bone graft material 70 to dislodge from and/or fall out of interbody device 10. Accordingly, as shown in FIG. 43, interbody device 10 may include one or more retention members 72 configured to retain bone graft material 70 within interbody device 10. In some arrangements, retention members 72 may be radiolucent. Radiolucent retention member(s) 72 may function to prevent bone graft material 70 from passing through, e.g., a window 62 without impeding visibility through window 62. For example, retention members 72 may include any one or more of a panel, screen, skin, and/or scaffold. In some arrangements, retention members 72 may be integrally and monolithically formed of a one-piece construction with interbody device 10. Alternatively, however, interbody device 10 may define one or more reception spaces 74 configured (e.g., sized and shaped) to receive one or more retention members 72 therein. As shown in FIG. 43, reception space(s) 74 may include a narrow slot, groove, slit, aperture, and/or opening within frame 60 of interbody device 10. As shown, reception spaces 74 may receive and hold one or more retention members 72 therein.

Figure 44:
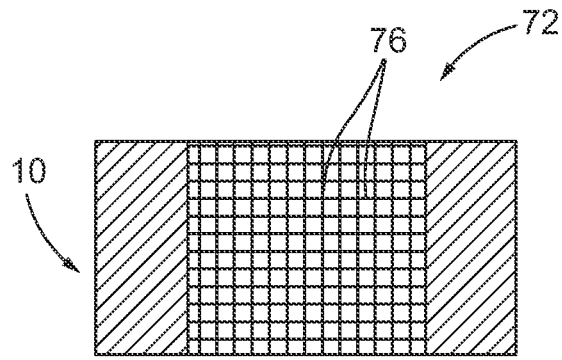
FIGS. 44-49 illustrate exemplary retention member arrangements.
Figure 45:
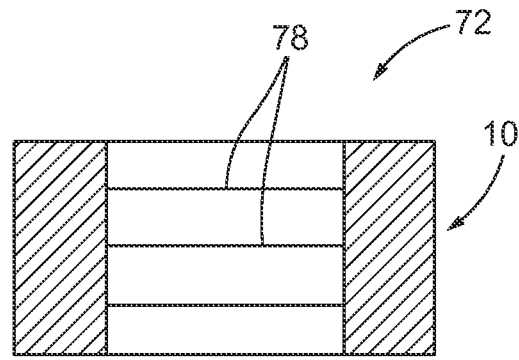
Figure 46:
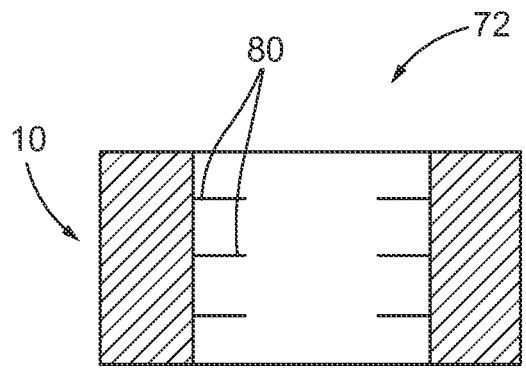
Figure 47:
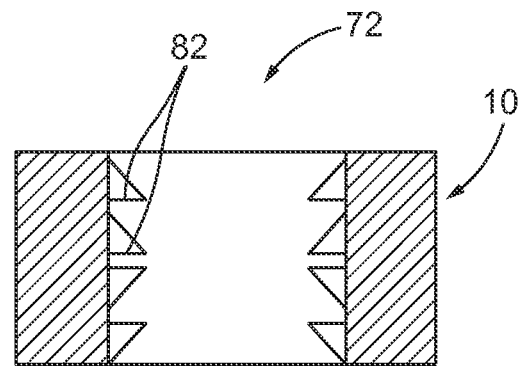

Additionally or alternatively, retention members 72 may include any of interbody device 10 geometry, serrations, teeth, keels, mesh, beams, and similar structures configured to retrain bone graft material 70 within interbody device 10. Indeed, FIGS. 44-49 illustrate cross-sectional views of exemplary interbody devices 10 taken along line X-X of FIG. 42, and further including various configurations of retention members 72. For example, as shown in FIG. 44, an exemplary retention member 72 may include a mesh screen 76 extending within a center opening of interbody device 10. Alternatively, as shown in FIG. 45, retention member 72 may include one or more bars, wires, and/or beams 78 extending substantially across a center opening of interbody device 10. Similarly, as shown in FIG. 46, retention member 72 may include one or more beam protrusions 80 extending partially across a center opening of interbody device 10. In yet a further arrangement, as shown in FIG. 47, retention member 72 may include one or more serrations 82 extending in a center opening of interbody device 10. Serrations 82 may have any suitable configuration. In some arrangements, serrations 82 may include substantially similar configurations. In other arrangements, however, each serration of serrations 82 may have unique configurations. For example, as shown in FIG. 47, a first set of serrations 82 may be oriented in a first direction while a second set of serrations 82 may be oriented in a second direction, different than the first direction. Any of mesh 76, beams 78, beam protrusions 80, and/or serrations 82 may be positioned along any one or more of a bottom face, top face, any plane extending between a top and bottom face, lateral side, rear face, and/or front face of interbody device 10.

Figure 48:
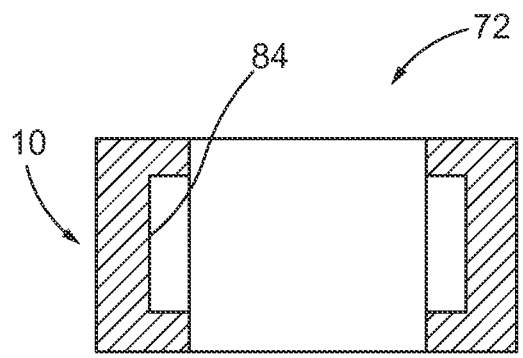
Figure 49:
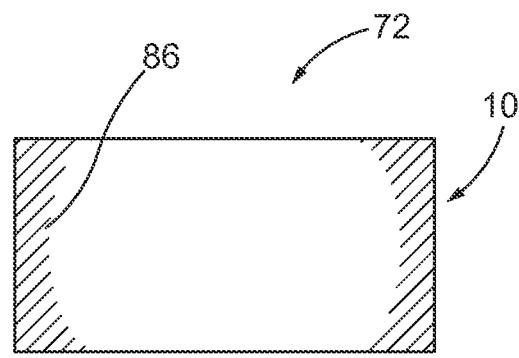

Further, as noted above, an internal geometry of interbody device 10 may be configured such that bone graft material 70 packed within interbody device 10 may be retained therein. That is, interior surface(s) of interbody device 10 may define one or more non-uniform or uneven surfaces which, upon receipt of packed bone graft material 70, may act to hold bone graft material 70 therein. For example, as shown in FIG. 48, inner walls of interbody device 10 may define a wall recess 84. Alternatively, as shown in FIG. 49, inner walls of interbody device 10 may define a wall concavity 86. Wall recess 84 and/or wall concavity 86 may be configured to receive and retain bone graft material 70 therein.

Figure 50:
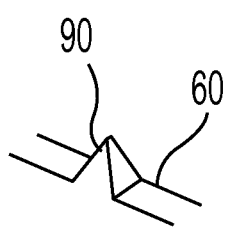
FIGS. 50 and 51 illustrate exemplary protrusion features of an interbody device.
Figure 51:
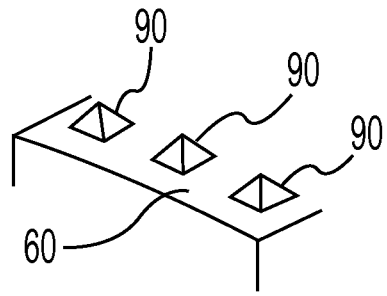

As noted above, interbody device 10 may include one or more features such as anti-migration and/or anchoring features, anti-rotation features, insertion tool features, reduced profile keel features, and the like. For example, interbody device 10 may include one or more features configured to maintain interbody device 10 within a desired position within spinal column 2. Such features may include one or more of notches, bumps, tangs, grips, and/or protrusions 90 extending from an outer surface of frame 60 of interbody device 10. Protrusions 90 may include any appropriate configuration, such as, for example, triangular (FIG. 50), pyramidal (FIG. 51), conical, and/or irregular shapes. Further, it is understood that any combination of geometric shapes and/or arrangement of protrusions 90 may be disposed along any surface of interbody device 10.

Figure 52:
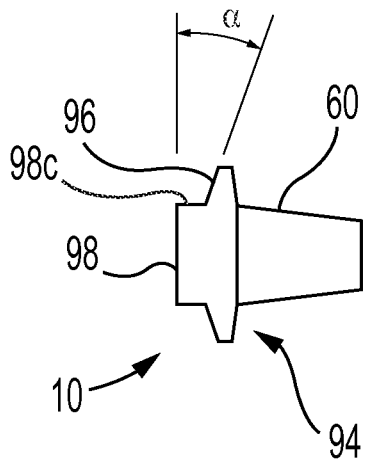
FIGS. 52-54 illustrate exemplary keel features of an interbody device.
Figure 53:
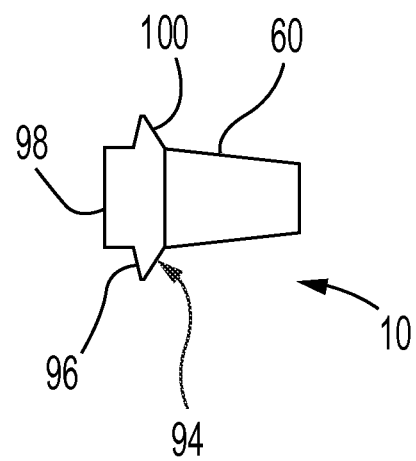

Further, as shown in FIGS. 52 and 53, exemplary interbody devices 10 may include one or more recessed keels. For example, frame 60 of interbody device 10 (or panel 54 of a composite interbody device 10), may include a tapered and/or angled keel feature 94 as shown in FIG. 52. That is, keel feature 94 may include an extension having an anterior surface 96 angled relative to an anterior-most surface 98 of interbody device 10. For example, as shown, surface 96 may extend at an angle α relative to surface 98. In some arrangements, angle α may be between about 0° and about 45°. As shown, keel feature 94 may be offset or spaced from anterior-most surface 98 of interbody device 10. In other words, keel feature 94 may be spaced away from an anterior-most surface 98 by a substantially planar wall portion 98c which extends perpendicularly to anterior-most surface 98. The angled arrangement of keel feature 94 may prevent interbody device 10 from inadvertently dislodging from spinal column 2 after placement between two adjacent vertebra 4. For example, keel feature 94 may enable movement in a first direction along the Z axis (FIG. 2) while preventing and/or deterring movement in a second direction along the Z axis. That is, keel feature 94 may facilitate relatively easier insertion of interbody device 10 between adjacent vertebrae while preventing or inhibiting removal of interbody device 10. Additionally, due to the angled configuration of keel feature 94, keel feature 94 may be recessed from surface 98 so as to minimize potential exposure and/or irritation of surrounding tissue and/or bone by interbody device 10. Accordingly, keel feature 94 may facilitate a zero-profile (or minimal-profile) arrangement of interbody device 10.

Figure 54:
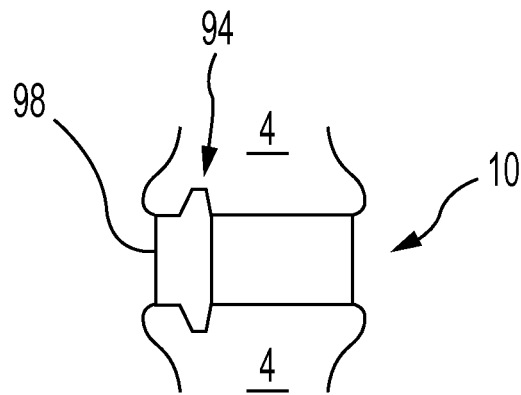

In a further arrangement, as shown in FIG. 53, for example, surface 96 may extend in a direction generally parallel to surface 98 while a posterior-facing surface 100 of keel feature 94 may be angled relative to surface 98. In this arrangement, keel feature 94 may enable movement in the second direction along the Z axis (FIG. 2) while preventing and/or deterring movement in the first direction along the Z axis. FIG. 54 illustrates an exemplary interbody device 10, having a recessed keel feature 94, positioned within spinal column 2 and engaging the endplates of adjacent vertebrae 4. Specifically, upon placement of interbody device 10 between adjacent vertebrae 4, keel feature(s) 94 may be embedded within vertebrae 4 and as such, prevent movement in at least one direction along the Z axis. Additionally, since keel feature 94 is recessed, keel feature 94 may be prevented from contacting, damaging, and/or irritating surrounding tissue.

Figure 55:
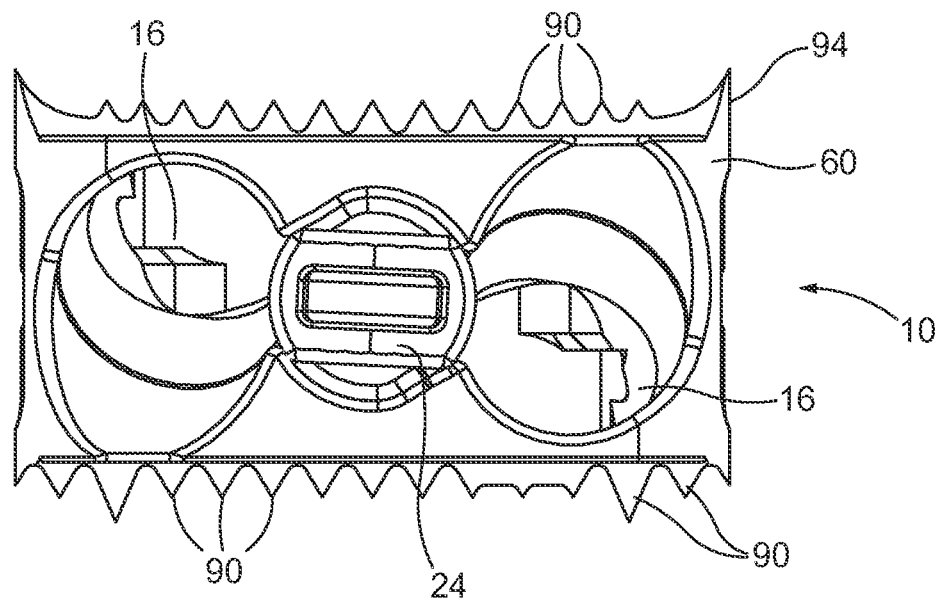
FIGS. 55 and 56 illustrate an exemplary interbody device.
Figure 56:
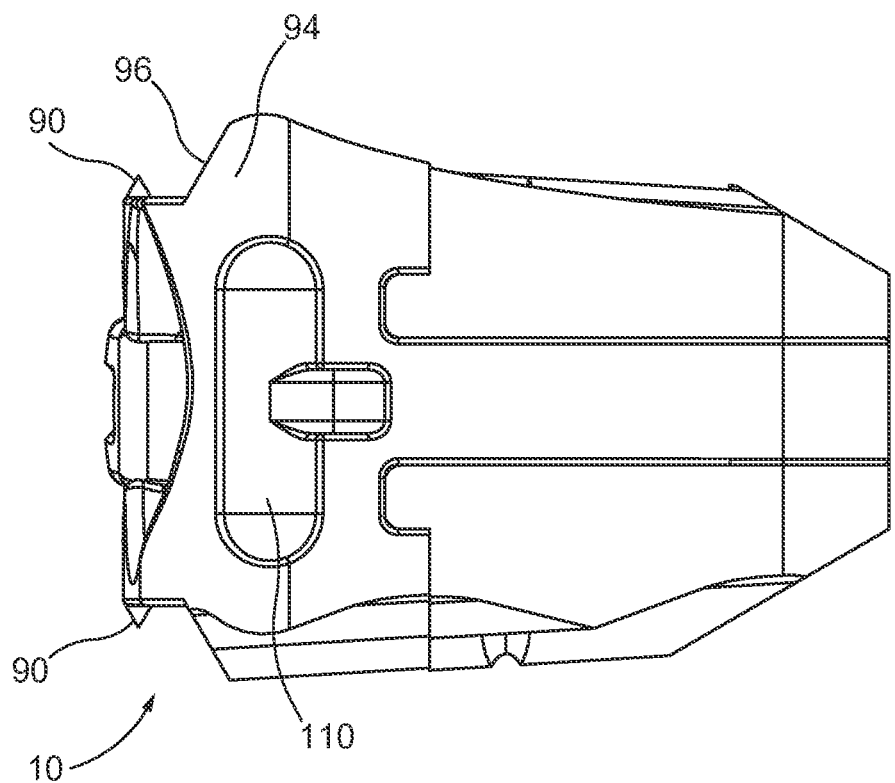

FIGS. 55 and 56 illustrate a front and side view of an exemplary interbody device 10, including features described above. For example, as shown in FIG. 55, interbody device 10 may include a frame 60, and in the case of a composite interbody device 10 (as shown in FIGS. 28-32), interbody device 10 may further include a panel 54 coupled to frame 60. Frame 60 may include any of the screw blocking mechanisms discussed above. For example, frame 60 and/or panel 54 may include one or more apertures 16 and an offsetting element 24 therebetween. Offsetting element 24 may be similar in construction and manner of use as described above. Additionally, interbody device 10 may include any one or more protrusions 90 configured to maintain interbody device 10 within a desired position within adjacent vertebrae 4. Such protrusions may be positioned along any appropriate portion of interbody device 10, such as, for example, an upper and lower surface of interbody device 10. Interbody device 10 may additionally include a recessed keel feature 94 as discussed above. Additionally, as shown in FIG. 56, interbody device 10 may include one or more instrumentation grooves, pockets, holes, and/or notches 110. Notches 110 may have any appropriate shape and/or arrangement to facilitate manipulation of interbody device 10 via a tool or other instrument during insertion, positioning, or manipulation of interbody device by a medical professional. That is, notches 110 may facilitate quick grasping of interbody device 10 via an appropriate tool (e.g., forceps or the like).

Figure 57:
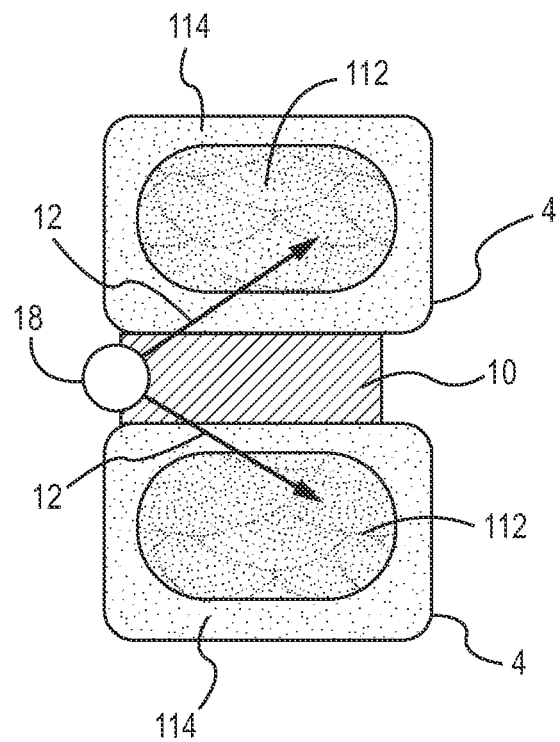
FIGS. 57-60 illustrate various views of a further exemplary interbody device.

FIGS. 57-60 illustrate exemplary features of a disclosed interbody device 10, including various features discussed above. Indeed, FIG. 57 schematically illustrates interbody device 10 positioned between two adjacent vertebrae 4. As noted above, each vertebra 4 includes spongy cancellous bone 112 which is then covered by a thin coating of cortical bone 114. As shown in FIG. 57, when one or more screws 12 are inserted directly through interbody device 10 into vertebra 4, a portion of screw 12 may extend through interbody device 10, through cortical bone 114, and terminate within cancellous bone 112, which may facilitate osteogenesis.

Figure 58:
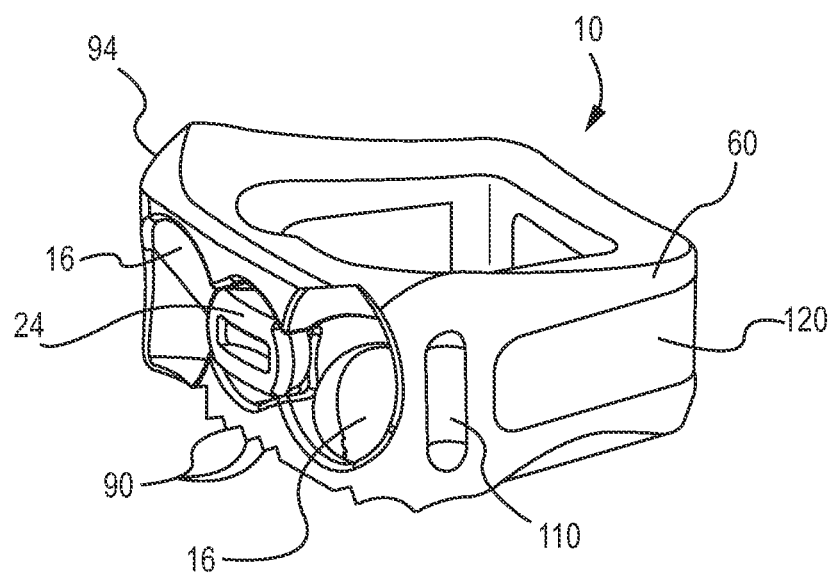
Figure 59:
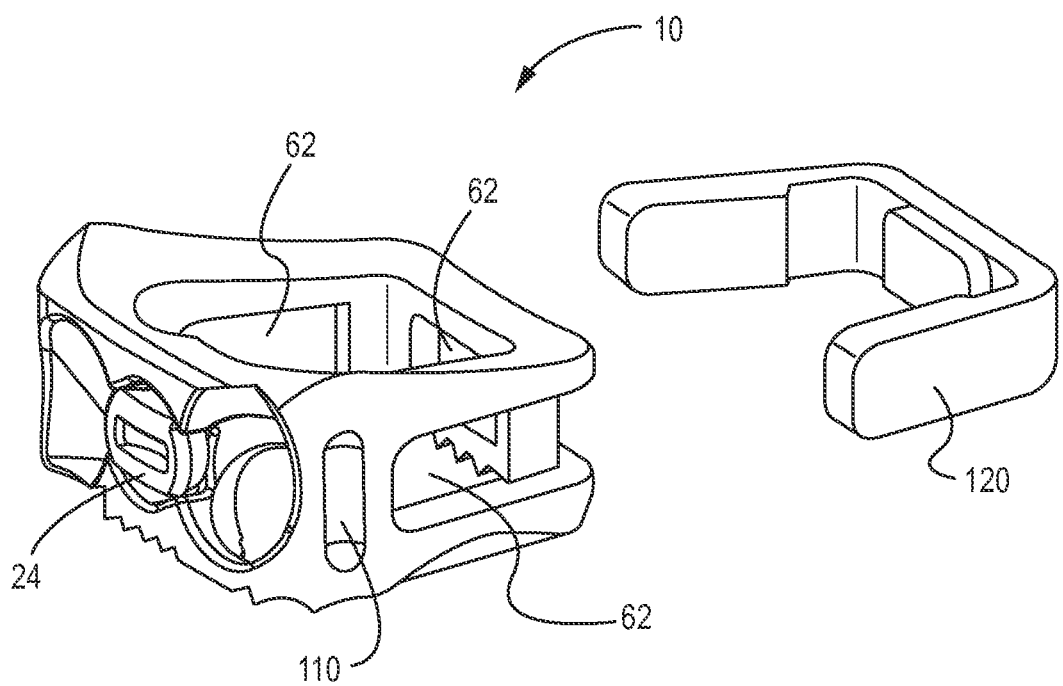
Figure 60:
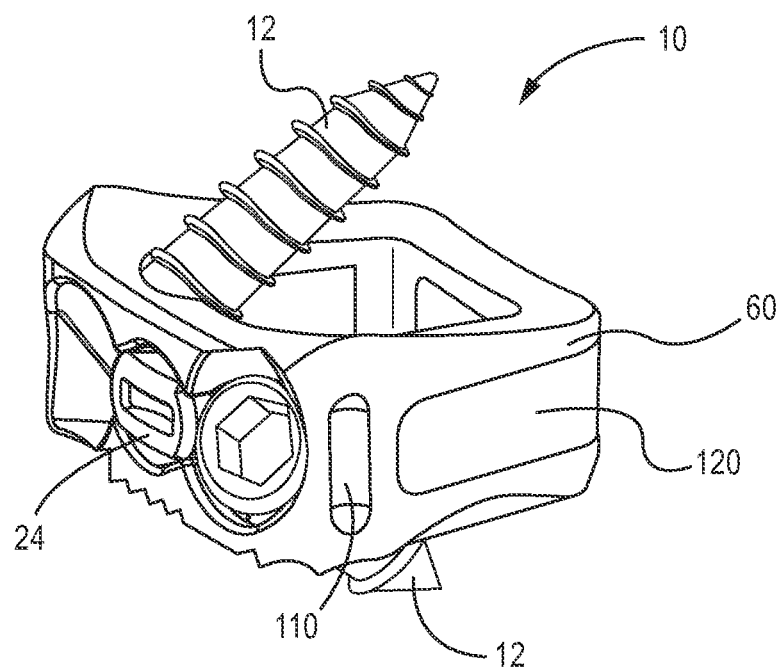

FIG. 58 is a perspective view of interbody device 10. As shown, interbody device 10 may include a frame 60 including any of the screw blocking mechanisms discussed above. For example, frame 60 may include one or more apertures 16 and an offsetting element 24 therebetween. Offsetting element 24 may be similar in construction and manner of use as described above. Additionally, interbody device 10 may include any one or more protrusions 90 configured to maintain interbody device 10 within a desired position within spinal column 2. Additionally, interbody device 10 may include a recessed keel feature 94 and one or more notches 110 as discussed above. Still further, interbody device 10 may include a graft containment sheath 120. Graft containment sheath 120 may be disposed along one or more portions of frame 60. For example, graft containment sheath 120 may be wrapped around frame 60 and may substantially cover or encompass windows 62 (FIG. 59) of frame 60. That is, graft containment sheath 120 may be configured so as to cooperate with frame 60 of interbody device 10 such that bone graft material 70 may be retained within interbody device 10 so as to facilitate fusion. As shown in FIG. 60, once interbody device 10, including graft containment sheath 120, is positioned within spinal column 2, screws 12 may be extended through apertures 16 and into vertebra 4 (e.g., through end plates of each vertebrae 4) so as to secure adjacent vertebrae 4 relative to one another.

Figure 61:
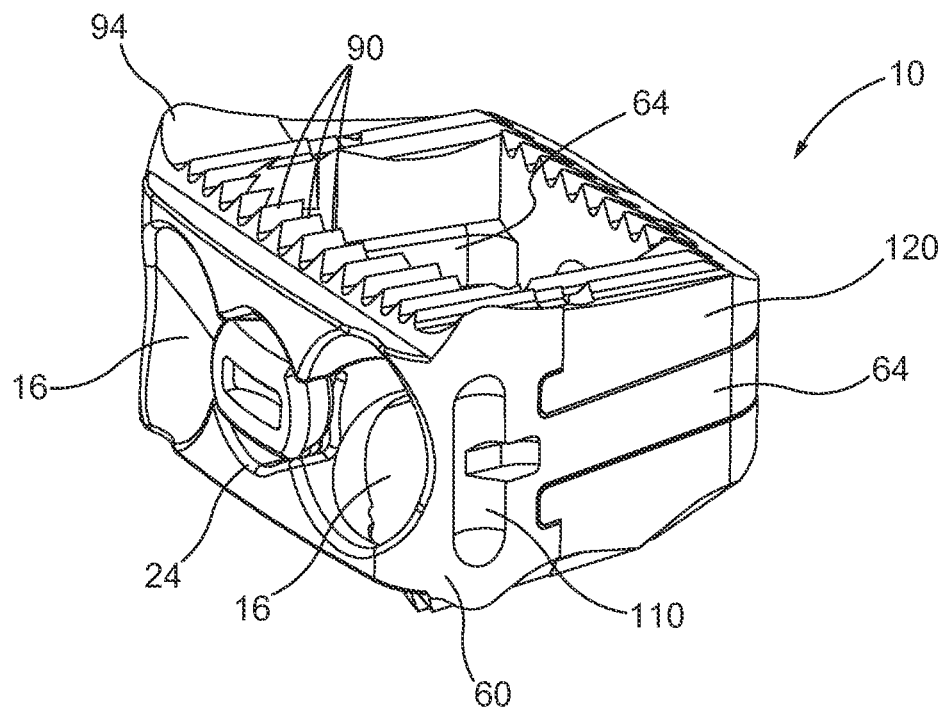
FIGS. 61-63 illustrate various views of yet another exemplary interbody device.
Figure 62:
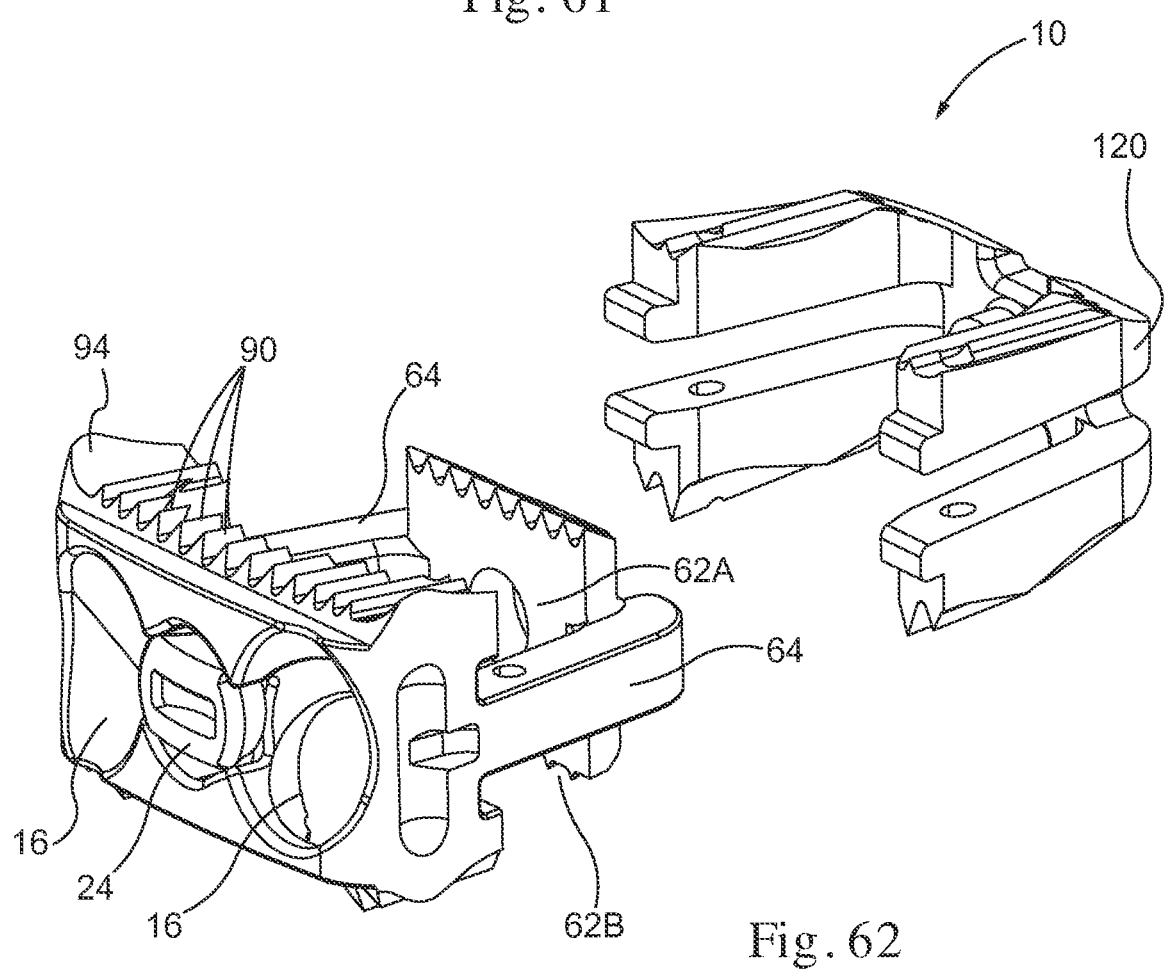
Figure 63:
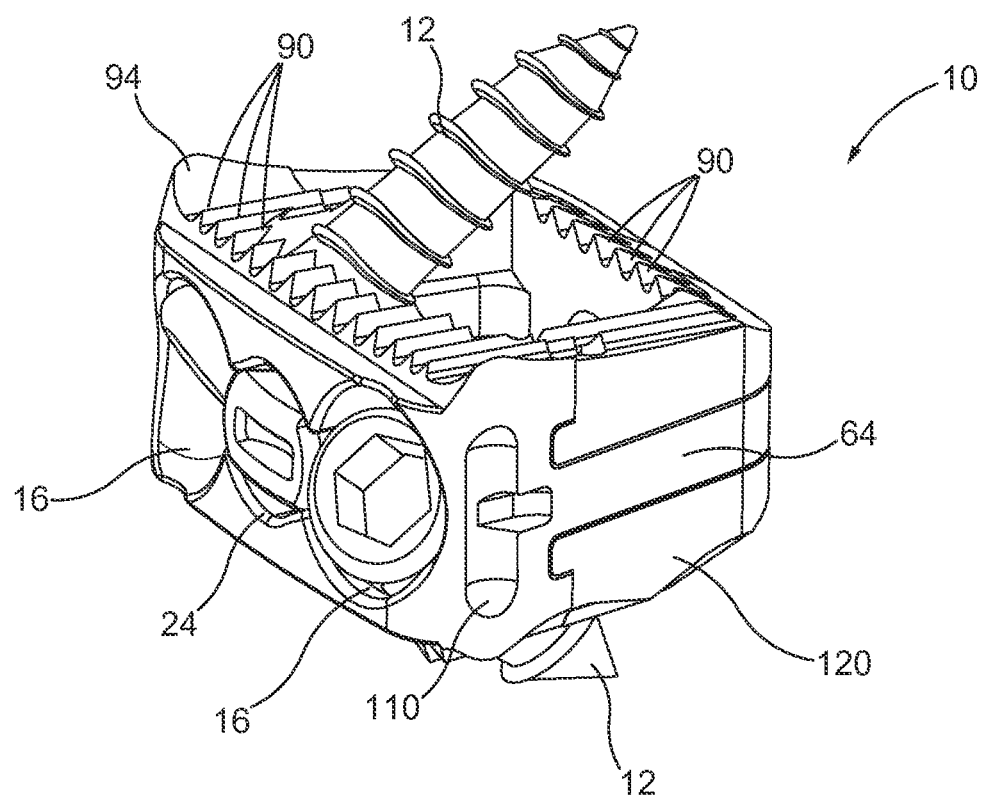

FIGS. 61-63 illustrate exemplary features of a further disclosed interbody device 10, including various features discussed above. FIG. 61 is a perspective view of interbody device 10. As shown, interbody device 10 may include a frame 60 including any of the screw blocking mechanisms discussed above. For example, frame 60 may include one or more apertures 16 and an offsetting element 24 therebetween. Offsetting element 24 may be similar in construction and manner of use as described above. As shown in FIG. 62, frame 60 may include lateral supports 64 defining first (e.g., upper) window portion 62A and a second (e.g., lower) window portion 62B. Additionally, interbody device 10 may include one or more protrusions 90 configured to maintain interbody device 10 within a desired position within spinal column 2. Additionally, interbody device 10 may include a recessed keel feature 94 and one or more notches 110 as discussed above. Still further, interbody device 10 may include a graft containment sheath 120. Graft containment sheath 120 may be disposed along one or more portions of frame 60. For example, graft containment sheath 120 may be wrapped around frame 60 and may substantially cover or encompass first and second window portions 62A and 62B of frame 60. That is, graft containment sheath 120 may be configured so as to cooperate with frame 60 of interbody device 10 such that bone graft material 70 may be retained within interbody device 10 so as to facilitate fusion. As shown in FIG. 63, once interbody device 10, including graft containment sheath 120, is positioned within spinal column 2, screws 12 may be extended through apertures 16 and into vertebra 4 (e.g., through end plates of each vertebra 4) so as to secure adjacent vertebrae relative to one another. In some arrangements, graft containment sheath 120 may be made of a radiolucent material such as, e.g., PEEK.

Figure 64:
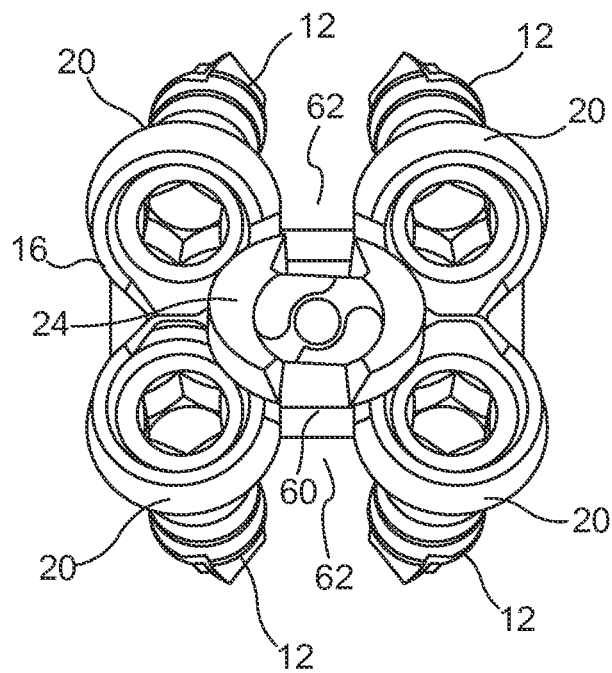
FIGS. 64-67 illustrate various view of a further exemplary interbody device.

FIGS. 64 and 65A-C illustrate a further arrangement of interbody device 10 including exemplary features described above. For example, as shown in FIG. 64, interbody device 10 may include an aperture 16 configured to receive four screws 12 therein. As described above in connection with FIG. 17, aperture 16 may include a first recess 20 positioned along a first portion of aperture 16, a second recess 20 positioned along a second portion of aperture 16, a third recess 20 positioned along a third portion of aperture 16, and a fourth recess 20 positioned along a fourth portion of aperture 16. Each recess 20 may be configured to retain a single screw 12 of the four screws 12. Additionally, as shown in FIG. 64, a screw blocking mechanism (such as, e.g., an offsetting element 24) may be positioned so as to cooperate with each of the four screws 12. Accordingly, in such an arrangement, offsetting element 24 may be provided at a center of aperture 16.

Additionally, interbody device 10 may include a graft containment sheath 120. Graft containment sheath 120 may be disposed along one or more portions of frame 60. For example, graft containment sheath 120 may be wrapped around frame 60 such that bone graft material 70 may be retained within desired portions of interbody device 10 so as to facilitate fusion.

Figure 65C:
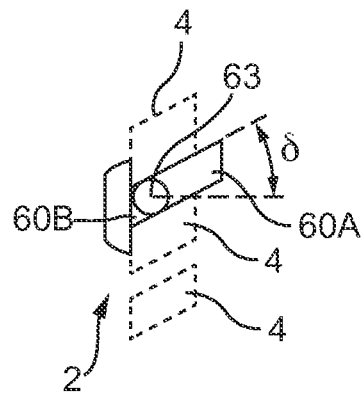
Figure 65A:
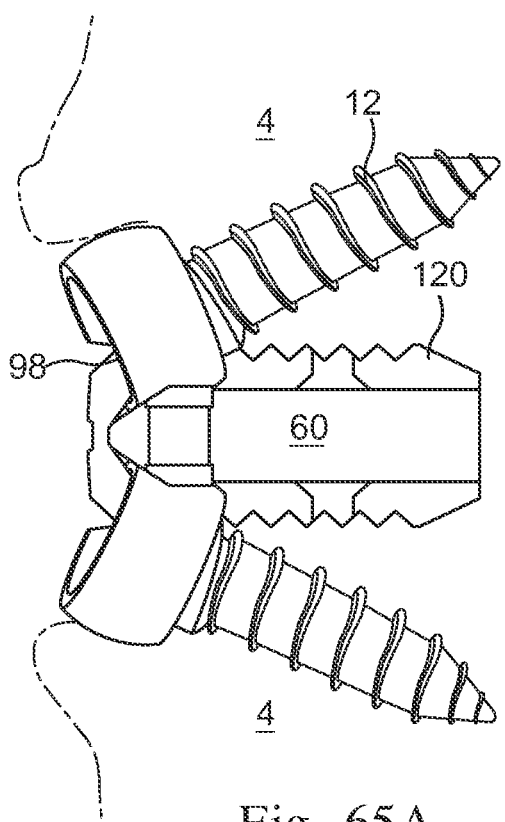
Figure 65B:
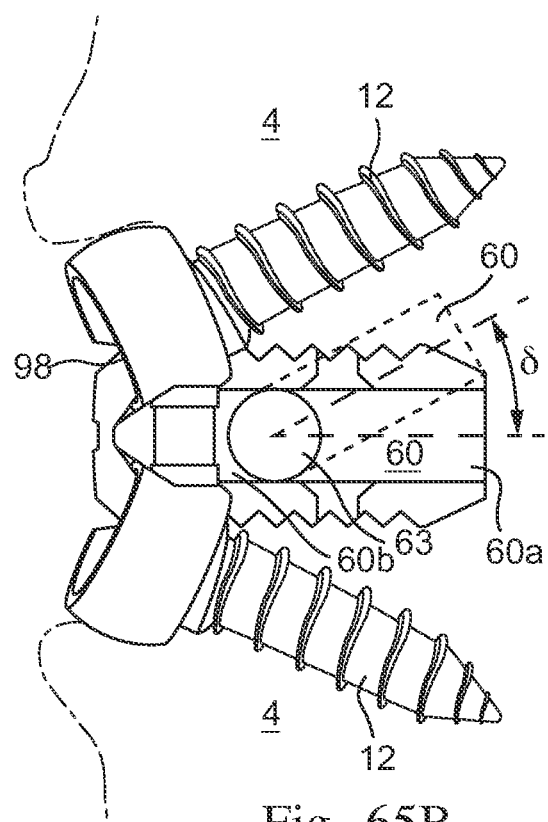

As shown in FIG. 64, frame 60 may provide one or more windows 62 along a coronal plane of interbody device 10, as will be described in further detail below Further, as shown in FIG. 65A, frame 60 may be bent, angled, or otherwise arranged so as to correspond in profile to spinal column 2. That is, at least the anterior-most surface 98 of frame 60 may be angled so as to be recessed relative to one or more vertebrae 4 (shown in phantom lines) of spinal column 2. Additionally or alternatively, as shown in FIGS. 65B and 65C, frame 60 may include a hinge 63 such that frame 60 may be selectively angled to accommodate various anatomies of spinal column 2. For example, a longitudinal axis of at least a first (e.g., posterior) portion 60A of frame 60 may be oriented at an angle σ relative to a longitudinal axis of at least a second (e.g., anterior) portion 60B of frame 60, as shown in phantom in FIG. 65B. Angle σ may be any appropriate angle. For example, angle σ may be between about 0° and about 90°. In some arrangements, angle σ may be about 45°. In such a manner, frame 60 may be arranged in any appropriate orientation so as to correspond to spinal column 2. For example, frame 60 may be arranged in any appropriate orientation either externally of the body of the patient, or after insertion within spinal column 2. In either arrangement, a medical professional may insert a tool (e.g., a wedge) to articulate second portion 60B relative to first portion 60A of frame 60. In some arrangements, hinge 63 may include a selectively actuatable lock (not shown), such that, once activated or locked, frame 60 may maintain a desired angle. Additionally, once de-activated or unlocked, frame 60 may again be readjusted along any appropriate angle.

Figure 66:
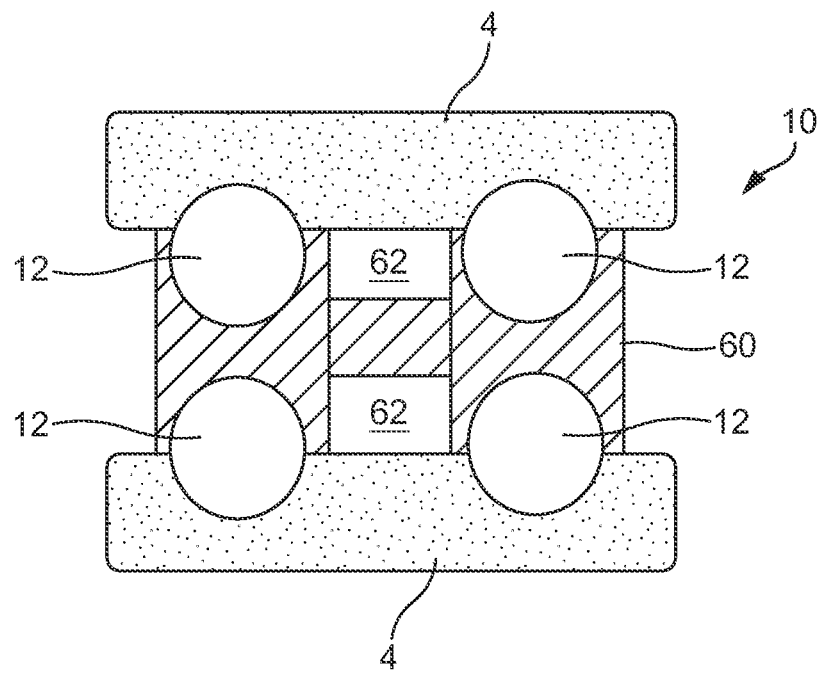
Figure 67:
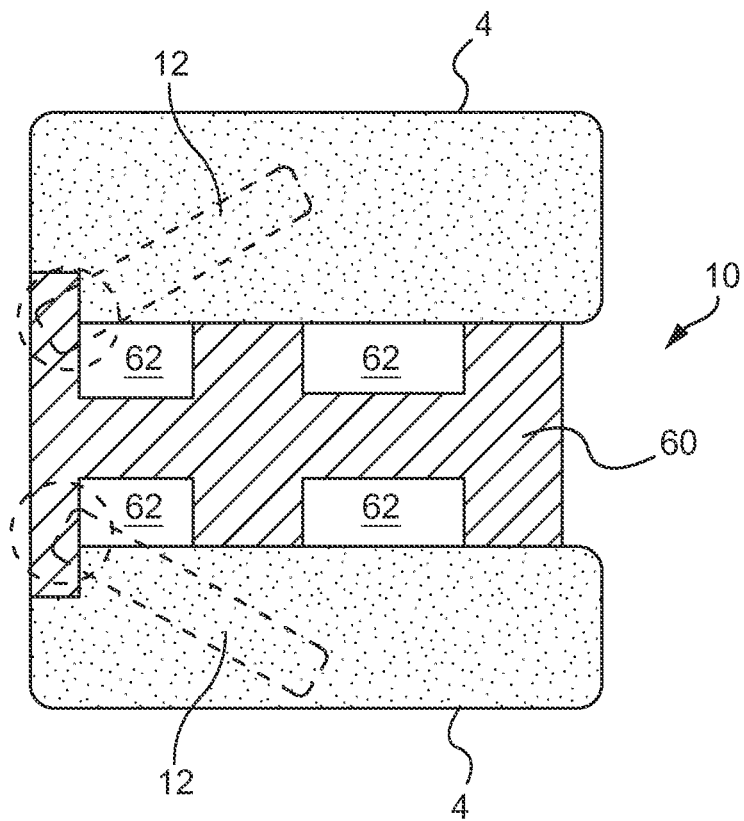
Figure 68:
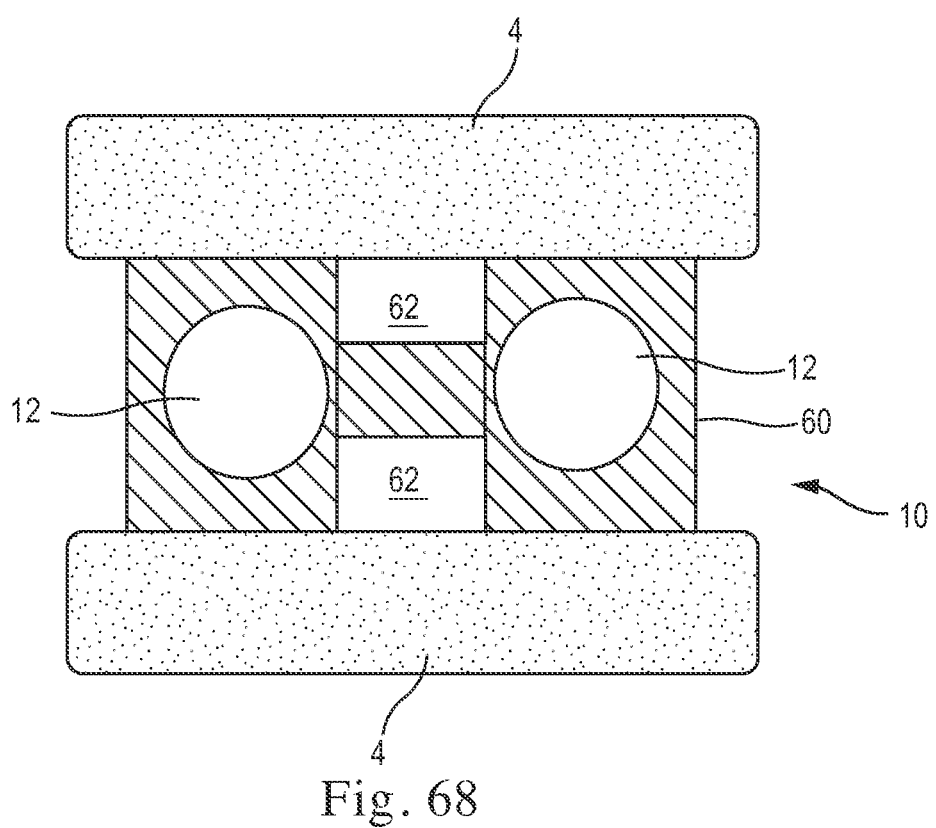
FIG. 68 illustrates another exemplary interbody device.

As noted above, frame 60 may provide one or more windows 62 along a coronal plane of interbody device 10. Accordingly, in the coronal view of interbody device 10 placed between two adjacent vertebrae 4 under X-ray vision, as shown in FIG. 66, windows 62 remains radiolucent such that fusion within and/or through windows 62 may be observed. Additionally, as shown in FIG. 67, frame 60 may define one or more windows 62 along the sagittal plane of interbody device 10. Accordingly, in the sagittal view of interbody device 10 placed between two adjacent vertebrae 4 under X-ray vision, as shown in FIG. 67, windows 62 remain radiolucent such that fusion within and/or through windows 62 may be observed. It is understood that coronal plane windows 62 may be included in any of the interbody device 10 structures noted above, and windows 62 may have any suitable configuration. For example, in an arrangement in which interbody device 10 is configured to receive two screws 12, frame 60 may define one or more coronal plane windows 62 therein. Accordingly, in the coronal view of interbody device 10 placed between two adjacent vertebrae 4 under X-ray vision, as shown in FIG. 68, windows 62 remain radiolucent such that fusion within and/or through windows 62 may be observed.

Figure 69A:
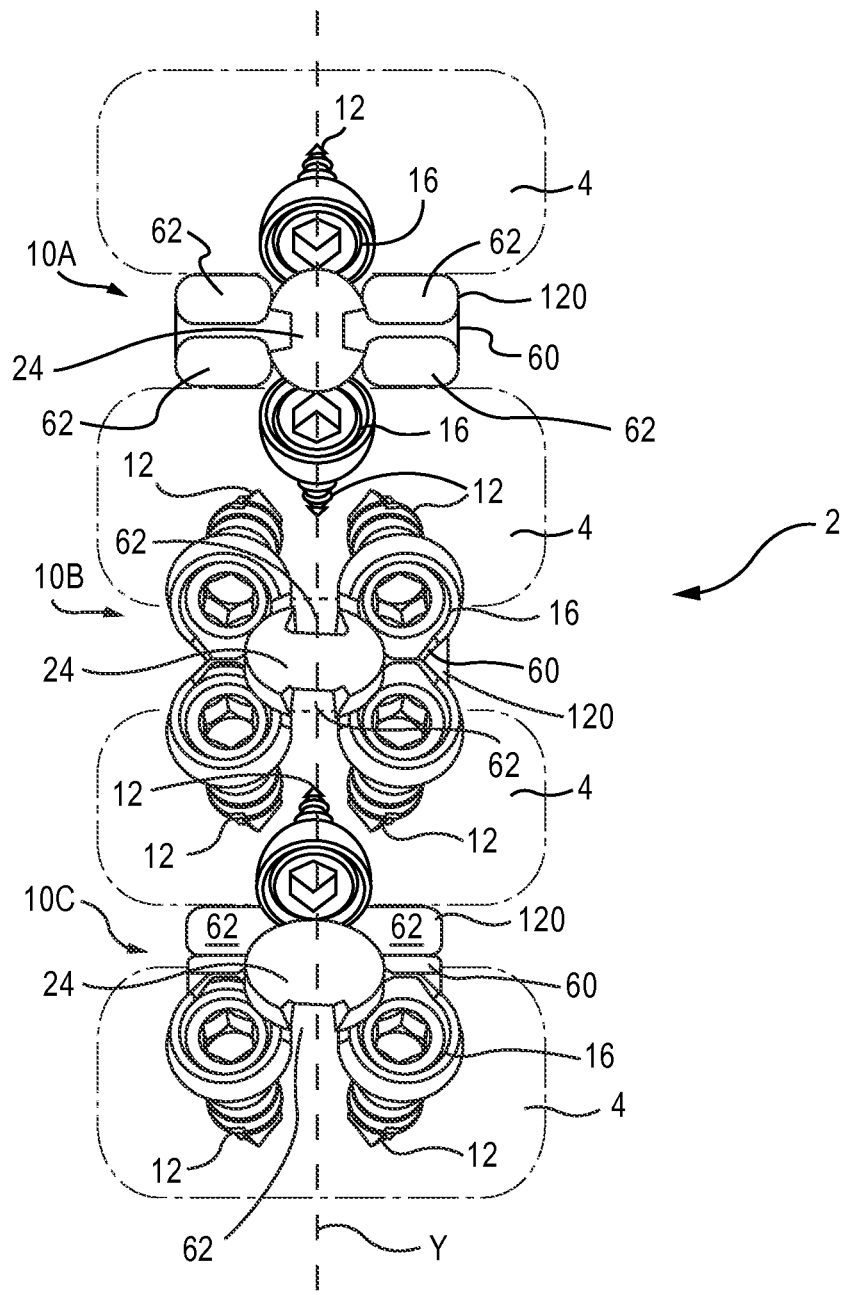
FIG. 69A illustrates a stacked exemplary interbody device.

FIG. 69A illustrates spinal column 2 having a plurality of interbody devices 10 disposed between vertebrae 4 (shown in phantom lines). As shown, each the plurality interbody devices 10 may be arranged along a central longitudinal axis (e.g., axis Y of FIG. 2) within a common plane. That is, one or more of screws 12 extending through one or more interbody devices 10 may be positioned along the central longitudinal axis Y in a common plane (e.g., screws 12 through a first interbody device 10A of FIG. 69A positioned so as to be aligned along axis Y). Additionally or alternatively, one or more screws 12 extending through one or more interbody device 10 may be positioned on a common plane and spaced (either equidistantly or non-equidistantly) from central longitudinal axis Y (e.g., screws 12 through second interbody device 10B of FIG. 69A). Additionally or alternatively, one or more screws 12 extending through one or more interbody devices 10 may be positioned such that some are positioned along the central longitudinal axis Y while others are spaced (either equidistantly or non-equidistantly) from central longitudinal axis Y along a common plane (e.g., screws 12 through second interbody device 10C of FIG. 69A).

Figure 69B:
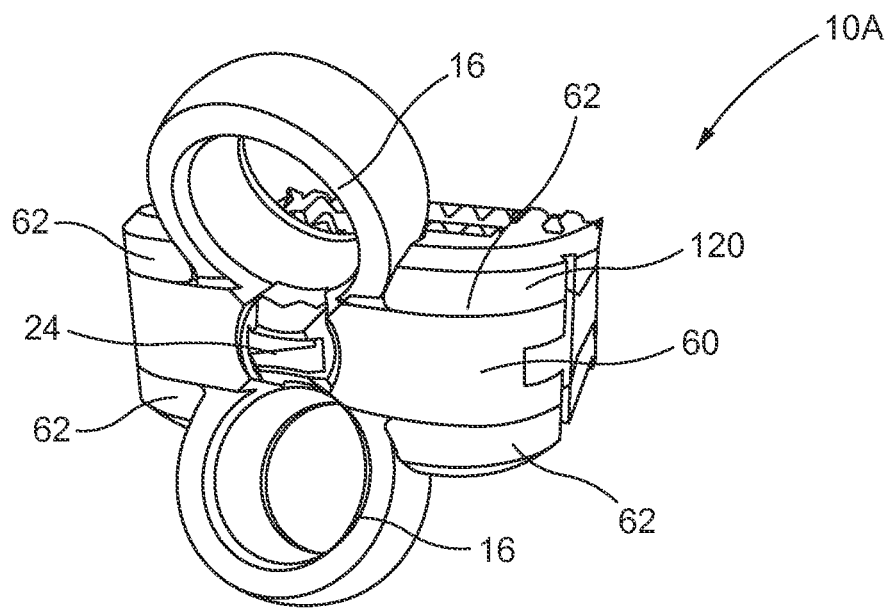
FIGS. 69B-D illustrate perspective views of exemplary interbody devices of the stacked interbody device of FIG. 69A.

For example, a first interbody device 10A may be disposed between adjacent vertebrae 4. A perspective view of first interbody device 10A, without screws 12, is shown in FIG. 69B. As shown in FIG. 69A, first interbody device 10A may be configured to receive two screws 12. As such, first interbody device 10A may include a frame 60 including any of the screw blocking mechanisms discussed above. For example, frame 60 may include one or more apertures 16 and an offsetting element 24 therebetween. Offsetting element 24 may be similar in construction and manner of use as described above. Frame 60 may define one or more windows 62 along a coronal plane of first interbody device 10A. Accordingly, in the coronal view of first interbody device 10A placed between two adjacent vertebrae 4 under X-ray vision, as shown in FIG. 69A, windows 62 remain radiolucent such that fusion within and/or through window 62 may be observed. Optionally, first interbody device 10A may include a graft containment sheath 120. Graft containment sheath 120 may be disposed along one or more portions of frame 60. For example, graft containment sheath 120 may be wrapped around frame 60 and may substantially fill or encompass windows 62 of frame 60. That is, graft containment sheath 120 may be configured so as to cooperate with frame 60 of first interbody device 10A such that bone graft material 70 may be retained within desired portions of first interbody device 10A so as to facilitate fusion.

Figure 69C:
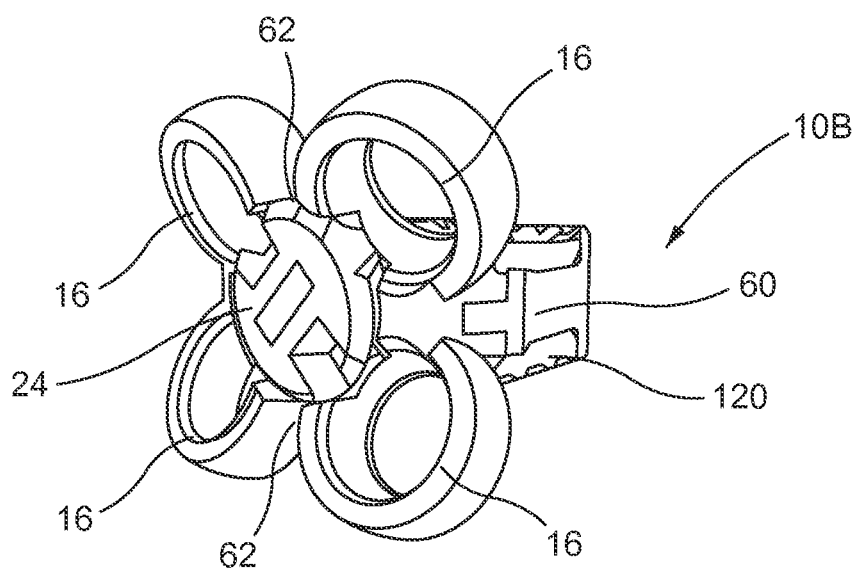

Further, as shown in FIG. 69A, a second interbody device 10B may be disposed between adjacent vertebrae 4. A perspective view of second interbody device 10B, without screws 12, is shown in FIG. 69C. As shown in FIG. 69A, second interbody device 10B may be configured to receive four screws 12. As such, second interbody device 10B may include a frame 60 including any of the screw blocking mechanisms discussed above. For example, frame 60 may include one or more apertures 16 and an offsetting element 24 therebetween. Offsetting element 24 may be similar in construction and manner of use as described above. Frame 60 may define one or more windows 62 along a coronal plane of second interbody device 10B. Accordingly, in the coronal view of second interbody device 10B placed between two adjacent vertebrae 4 under X-ray vision, as shown in FIG. 69A, windows 62 remain radiolucent such that fusion within and/or through window 62 may be observed. Optionally, second interbody device 10B may include a graft containment sheath 120. Graft containment sheath 120 may be disposed along one or more portions of frame 60. For example, graft containment sheath 120 may be wrapped around frame 60 and may substantially fill or encompass windows 62 of frame 60. That is, graft containment sheath 120 may be configured so as to cooperate with frame 60 of second interbody device 10B such that bone graft material 70 may be disposed along desired portions of second interbody device 10B so as to facilitate fusion.

Figure 69D:
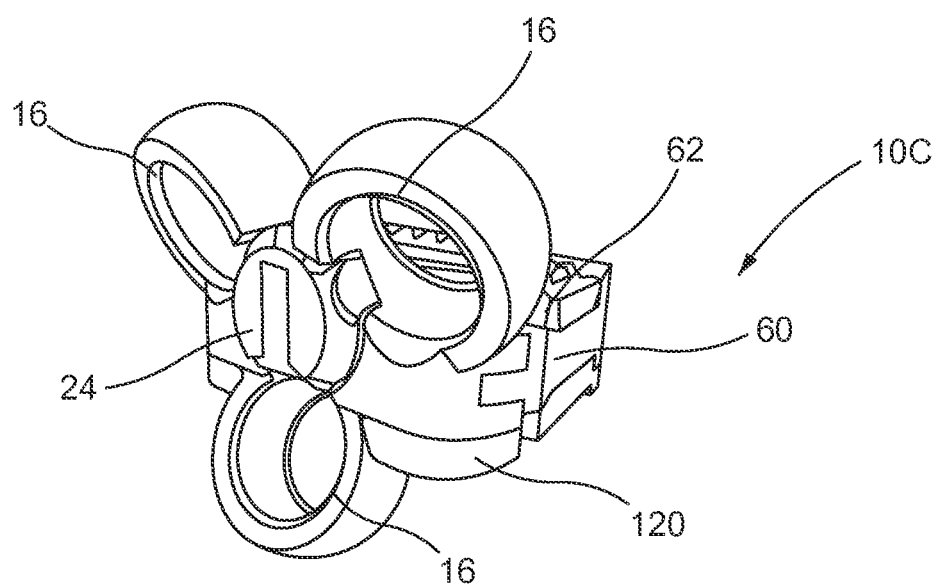

Additionally, as shown in FIG. 69C, a third interbody device 100 may be disposed between adjacent vertebra 4. A perspective view of third interbody device 100, without screws 12, is shown in FIG. 69D. As shown in FIG. 69A, third interbody device 100 may be configured to receive three screws 12. As such, third interbody device 100 may include a frame 60 including any of the screw blocking mechanisms discussed above. For example, frame 60 may include one or more apertures 16 and an offsetting element 24 therebetween. Offsetting element 24 may be similar in construction and manner of use as described above. Frame 60 may define one or more windows 62 along a coronal plane of third interbody device 100. Accordingly, in the coronal view of third interbody device 100 placed between two adjacent vertebrae 4 under X-ray vision, as shown in FIG. 69A, windows 62 remain radiolucent such that fusion within and/or through window 62 may be observed. Optionally, third interbody device 100 may include a graft containment sheath 120. Graft containment sheath 120 may be disposed along one or more portions of frame 60. For example, graft containment sheath 120 may be wrapped around frame 60 and may substantially fill or encompass windows 62 of frame 60. That is, graft containment sheath 120 may be configured so as to cooperate with frame 60 of third interbody device 100 such that bone graft material 70 may be retained within desired portions of third interbody device 100 so as to facilitate fusion.

As shown in FIG. 69A, a screw 12 extends through first interbody device 10A toward second interbody device 10B and into vertebra 4, and screws 12 extend through second interbody device 10B toward first interbody device 10A and into the same vertebra 4 may be spaced from one another. That is, screws 12 may be arranged and/or oriented so as not to interfere with one another as each passes through a respective interbody device 10 and into vertebra 4. Indeed, screw 12 extending through first interbody device 10 and into vertebra 4 may be received within vertebra 4 between screws 12 extending through second interbody device 10B and into vertebra 4. Likewise, screws 12 extending through second interbody device 10B toward third interbody device 100 and into vertebra 4, and screws 12 extending through third interbody device 100 toward second interbody device 10B and into the same vertebra 4 may be spaced from one another. Accordingly, first interbody device 10A, second interbody device 10B, and third interbody device 100 may be stacked along spinal column 2 without interfering with one another. In such a manner, multiple portions of spinal column 2 may be treated simultaneously. It is understood that first interbody device 10A, second interbody device 10B, and third interbody device 100 are merely representative and any arrangement of interbody devices 10 may be stacked along spinal column 2. Accordingly, any appropriate arrangement of any of the above disclosed interbody devices 10 may be arranged along spinal column 2 so as to produce any desired therapeutic effect.

As noted above in connection with FIG. 27, a standalone interbody device 10 may include a closed cage having an enlarged front side 50. Such an enlarged front side 50 may facilitate placement of screws 12 at varied heights along spinal column 2. Alternatively, as noted above in connection with FIG. 32, a composite interbody device 10 may include a closed cage coupled to a panel 54 enlarged relative to the cage. Such an enlarged panel 54 may also facilitate placement of screws 12 at varied heights along spinal column 2. Additionally, in some examples, panels 54 may be used alone without a cage coupled thereto. In any such arrangement, as shown in FIGS. 70-75, an enlarged front side 50 and/or panel 54 may include any appropriate shape. By way of example only, FIGS. 70-78E will be described in connection with a composite interbody device 10 including panel 54. It is understood, however, that the features described below may likewise be employed in a standalone interbody device 10.

Figure 1:
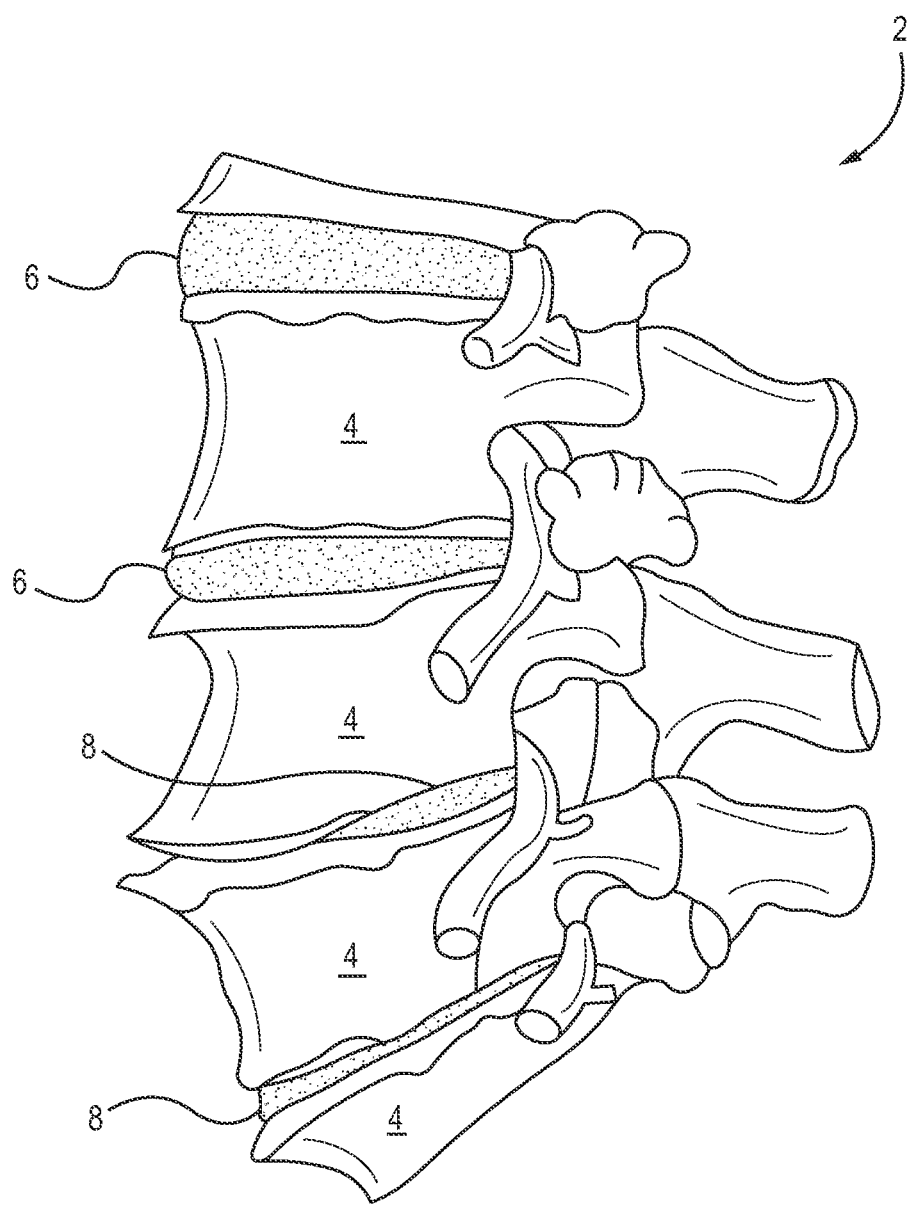
FIG. 1 illustrates a patient's spinal column.
Figure 2:
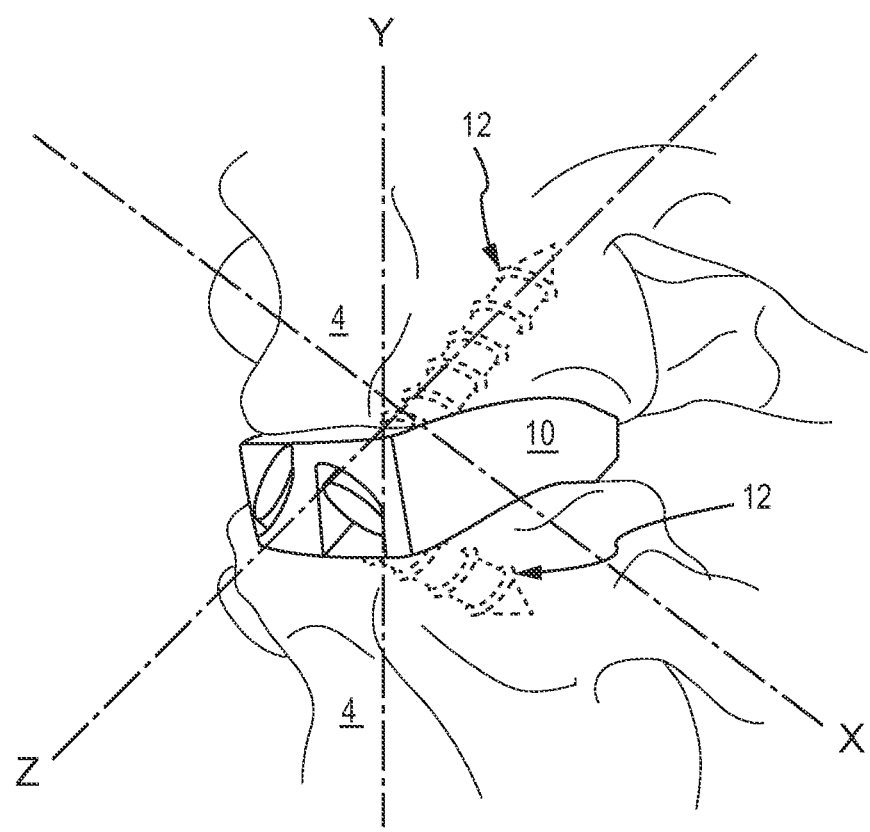
FIG. 2 illustrates an interbody device positioned within the patient's spinal column.
Figure 70:
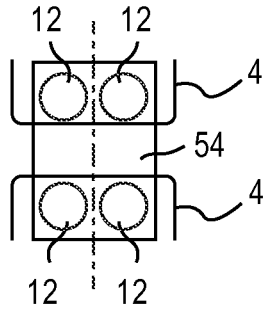
FIGS. 70-75 illustrate exemplary arrangements of a face of an interbody device.
Figure 71:
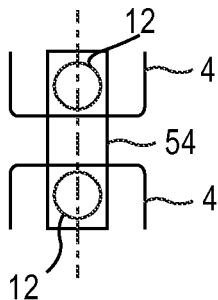
Figure 72:
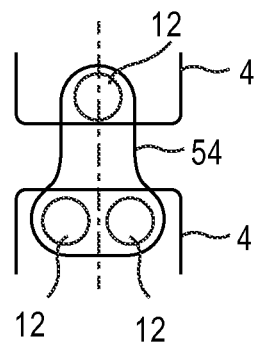
Figure 73:
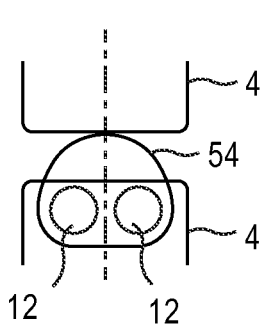
Figure 74:
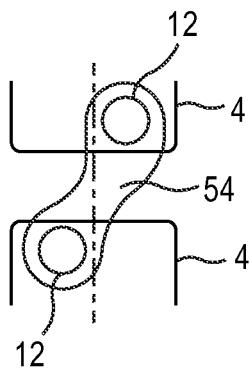
Figure 75:
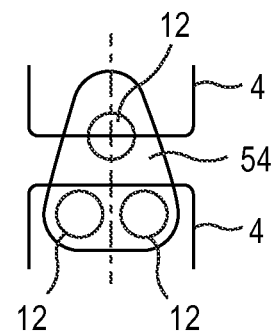
Figure 76:
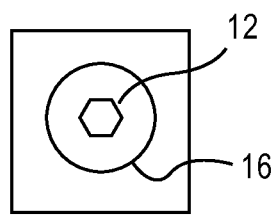
FIGS. 76 and 77 illustrate exemplary aperture arrangements of an interbody device.
Figure 77:
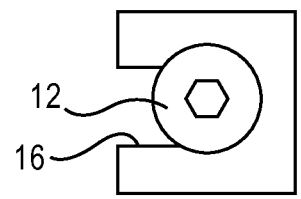
Figure 78:
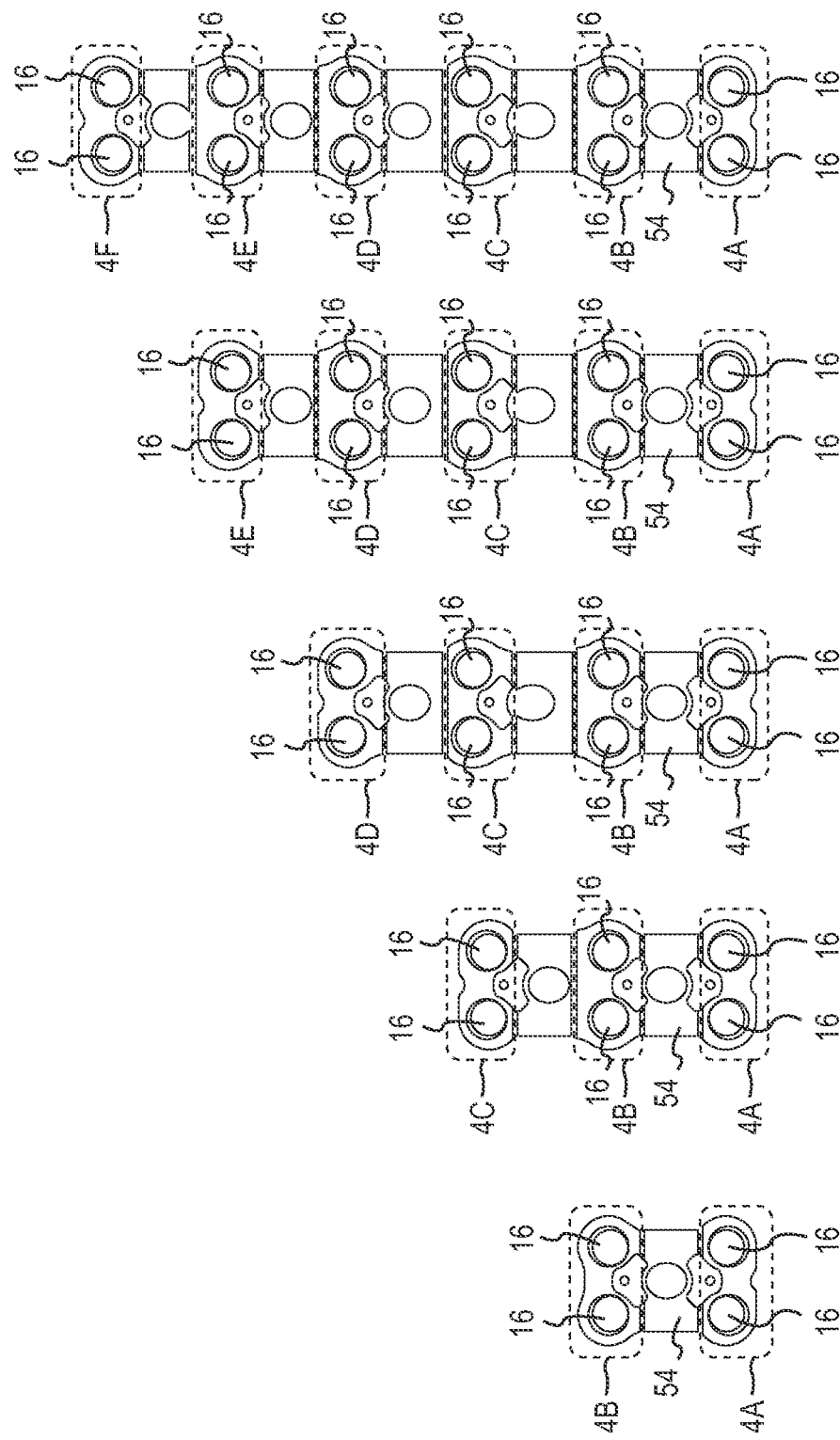
FIGS. 78A-78E illustrate exemplary multi-vertebrae devices.

For example, as shown in FIGS. 70 and 71, panel 54 may be generally symmetric about the X and Y planes of spinal column 2 (FIG. 2). That is, panel 54 may be generally rectangular or square. In some arrangements, as shown in FIG. 70, panel 54 may define one or more apertures 16, each configured to receive a screw 12 therethrough. Alternatively, as shown in FIG. 71, panel 54 may define one or more apertures 16 each configured to receive a screw 12 therethrough. In either arrangement, a first half of screws 12 may extend through panel 54 and into a first vertebra 4 while a second half of screws 12 may extend through panel 54 into a second, adjacent vertebra 4. Alternatively, as shown in FIGS. 72-75, panel 54 may be asymmetric about one or both of the X and Y planes of spinal column 2. For example, as shown in FIG. 72, panel 54 may be generally triangular with rounded corners or apices. Panel 54 may define one or more apertures 16 configured to receive three screws therethrough. Accordingly, a first screw 12 may extend through panel 54 and into a first vertebra 4 while second and third screws 12 may extend through panel 54 into a second vertebra 4. Alternatively, as shown in FIG. 73, panel 54 may define a general buttress shape. Accordingly, panel 54 may define one or more apertures 16 each configured to receive a screw 12 therethrough, each of which may extend through panel 54 into a common vertebra 4. In an additional embodiment, as shown in FIG. 74, panel 54 may be generally s-curved. Panel 54 may define one or more apertures 16 each configured to receive a screw 12 therethrough. Accordingly, a first screw 12 may extend through panel 54 and into a first vertebra 4 while a second screw 12 may extend through panel 54 into a second, adjacent vertebra 4. As shown in each of FIGS. 70-74, each screw 12 may be configured to extend directly through an anterior surface of vertebra 4. In other arrangements, as shown in FIG. 75, one or more screws 12 may be configured so as to extend through an edge of vertebra 4. That is, panel 54 may be shortened relative to panel 54 of FIGS. 70-74. Accordingly, one or more screws 12 extending though panel 54 may be arranged so as to enter vertebra 4 through an edge thereof. It is understood that such a shortened panel 54 may be used for any of the arrangements of FIGS. 70-74 without departing from the scope of this disclosure Accordingly, any one or more of screws 12, of any disclosed arrangement, may be configured so as to extend through an edge of vertebra 4. Additionally, it is understood that each aperture 16 may be encircled on all sides thereof by panel 54 thus forming a closed loop aperture 16, as shown in FIG. 76. Alternatively, however, one or more apertures 16 defined by panel 54 may be open loop apertures. That is, aperture 16 may extend to an edge of panel 54 such that one or more screws 12 may be received therethrough. Accordingly, panel 54 may not encircle aperture 16 on all sides thereof, as shown in FIG. 77.

Additionally, while FIGS. 70-75 illustrate arrangements in which panel 54 is coupled to two adjacent vertebrae 4, the disclosure is not so limited. Rather, panels 54 may be configured so as to be coupled to more than two vertebrae 4. That is, panels 54 may be multi-level panels 54 spanning a plurality of vertebrae 4. For example, FIGS. 78A-78E illustrate exemplary arrangements of panel 54 coupled to any of 2, 3, 4, 5, and/or 6 vertebra 4. Panels 54 may be similar to those described above, and may include any appropriate number of aperture 16 for receiving screws 12 therethrough. Additionally, any of panels 54 may include any of the screw blocking mechanisms or windows 62 noted above. Additionally, panels 54 may have one or more features configured to assist instruments to define trajectories of screws 12 through panel 54 into vertebrae 4 as will be described in further detail below. Such features may include, for example, female bores 122, male protrusions, or the like.

In a first exemplary arrangement, as shown in FIG. 78A, similar to the arrangements of FIGS. 70-75 above, panel 54 may define one or more apertures 16 for receiving screws 12 (not shown) therethrough. As shown, panel 54 may be configured to receive four screws 12 therethrough. Indeed, first and second screws 12 may be configured to extend through panel 54 into a first vertebra 4A, while third and fourth screws 12 may be configured to extend through plate 54 into a second vertebra 4B. In a further arrangement, as shown in FIG. 78B, panel 54 may define one or more apertures 16 configured to receive six screws 12 (not shown) therethrough. Indeed, first and second screws 12 may be configured to extend through panel 54 into a first vertebra 4A, third and fourth screws 12 may be configured to extend through plate 54 into a second vertebra 4B, and fifth and sixth screws 12 may be configured to extend through plate 54 into a third vertebra 4C. Still further, as shown in FIG. 78C, panel 54 may define one or more apertures 16 configured to receive eight screws 12 (not shown) therethrough. That is, first and second screws 12 may be configured to extend through panel 54 into a first vertebra 4A, third and fourth screws 12 may be configured to extend through plate 54 into a second vertebra 4B, fifth and sixth screws 12 may be configured to extend through plate 54 into a third vertebra 4C, and seventh and eighth screws 12 may be configured to extend through plate 54 into a fourth vertebra 4D. Alternatively, as shown in FIG. 78D, panel 54 may define one or more apertures 16 configured to receive ten screws 12 (not shown) therethrough. Indeed, first and second screws 12 may be configured to extend through panel 54 into a first vertebra 4A, third and fourth screws 12 may be configured to extend through plate 54 into a second vertebra 4B, fifth and sixth screws 12 may be configured to extend through plate 54 into a third vertebra 4C, seventh and eighth screws 12 may be configured to extend through plate 54 into a fourth vertebra 4D, and ninth and tenth screws 12 may be configured to extend through plate 54 into a fifth vertebra 4E. Still further, as shown in FIG. 78E, panel 54 may define one or more apertures 16 configured to receive twelve screws 12 (not shown) therethrough. That is, first and second screws 12 may be configured to extend through panel 54 into a first vertebra 4A, third and fourth screws 12 may be configured to extend through plate 54 into a second vertebra 4B, fifth and sixth screws 12 may be configured to extend through plate 54 into a third vertebra 4C, seventh and eighth screws 12 may be configured to extend through plate 54 into a fourth vertebra 4D, ninth and tenth screws 12 may be configured to extend through plate 54 into a fifth vertebra 4E, and eleventh and twelfth screws 12 may be configured to extend through plate 54 into a sixth vertebra 4F.

It is to be understood that any of the previously disclosed features of interbody device 10 may be used together or separately. For example, any of the disclosed screw blocking mechanisms noted above may be combined with any of the disclosed composite and/or standalone interbody devices 10. Moreover, any of the interbody devices 10 disclosed herein may include any one or more of coronal and/or sagittal plane windows 62. Additionally, any of the interbody devices 10 disclosed herein may include any of packed bone graft material 70, retention members 72, graft containment sheath 120, anti-migration and/or anchoring features, anti-rotation features 90, insertion tool features 110, reduced profile keel 94 features, and the like. Additionally, it is understood that any interbody device 10 disclosed herein may be appropriately sized depending on a desired therapeutic effect. For example, in some arrangements, interbody device 10 may have a width between about 10 mm and about 45 mm. For example, a width of an exemplary interbody device 10 may be between about 10 mm and about 25 mm; between about 25 mm and about 45 mm; or between about 15 mm and about 25 mm. Further, interbody device 10 may have a depth between about 10 mm and about 70 mm. For example, a depth of an exemplary interbody device 10 may be between about 10 mm and about 20 mm; between about 20 mm and about 35 mm; or between about 30 mm and about 70 mm. Moreover, a height of an exemplary interbody device 10 may be between about 5 mm and about 25 mm. Further, a sagittal angle of lordosis may be between about 0° and about 15°; or between about 0° and about 12°.

Distractor and/or Trial Structure and Features

Figure 79:
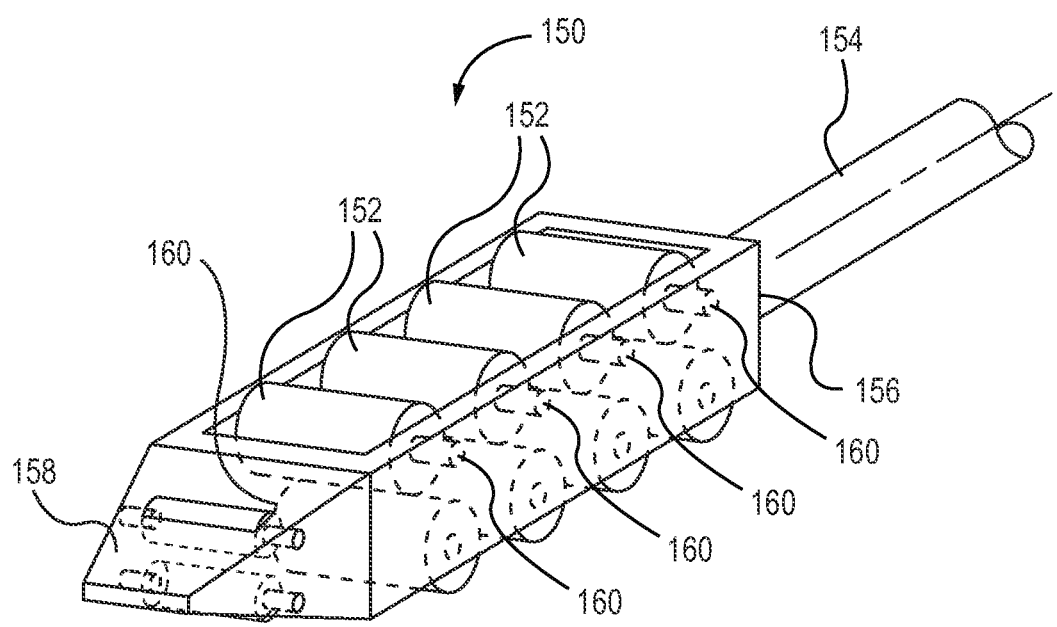
FIG. 79 illustrates an exemplary distractor and/or trial tool.

During a procedure for any of ACIF, ALIF, DLIF, PLIF, and/or TLIF, one or more distractors and/or trials of various sizes may be utilized. Each trial and/or distractor may be forcibly inserted between adjacent vertebrae 4 so as to determine an appropriate size and/or positioning of an interbody device 10 to be received within spinal column 2. To reduce the amount of insertion force required, an exemplary distractor and or trial tool 150 may include one or more friction reducing elements such as, for example, bearings, wheels, discs, rollers, and/or combinations thereof. Indeed, as shown in FIG. 79, rollers 152 may be generally cylindrical. Alternatively, rollers 152 may include any appropriate geometric shape. In some arrangements, one or more rollers 152 may be textured or otherwise include protrusions or tread (not shown). As such, rollers 152 may score vertebrae 4 during insertion to promote bleeding therefrom.

As shown in FIG. 79, an exemplary tool 150 may include a shaft 154 coupled to a body 156 for manipulation thereof. That is, shaft 154 may be any appropriate structure coupled to body 156 and having sufficient columnar strength to facilitate insertion and retraction of body 156 between two adjacent vertebrae 4. In some arrangements, shaft 154 may be removably coupled to body 156. As shown, body 156 may include a reduced profile leading edge portion. For example, body 156 may include a tapered nose 158. Nose 158 may assist a medical professional insert and retract body 156 between adjacent vertebrae 4. Body 156 and/or shaft 154 may include any one or more of metal, plastic, and elastomer. Additionally, in some arrangements, body 156 may be configured for selective expansion. For example, body 156 may include upper and lower body portions (not shown) coupled together via any appropriate mechanism (not shown). An expandable member, such as, for example, a selectively inflatable balloon (not shown) may be positioned between the upper and lower body portions such that, upon inflation, body 156 expands in height.

Body 156 may include one or more rollers 152. For example, body 156 may include ten rollers 152, four along a top portion of body 156 configured to reduce friction between body 156 and a first vertebra 4, and four along a bottom portion of body 156 configured to reduce friction between body 156 and a second vertebra 4. Additionally, one or more rollers 152 may be positioned along a top portion of nose 158 and a bottom portion of nose 158. Such an arrangement is merely exemplary. Rather, more or fewer rollers 152 may be positioned along body 156 and/or nose 158. Further, in some arrangements, a different number of rollers 152 may be positioned along the top portion of body 156 and/or top portion of nose 158 than the bottom portion of body 156 and/or the bottom portion of nose 158. Further, rollers 152 may be individually rotatable or pivotable about individual axes 160. Accordingly, each roller 152 may be rotated independently of remaining rollers 152. Alternatively, one or more rollers 152 may be coupled together for simultaneous rotation. For example, a belt or similar structure (not shown) may extend across one or more rollers 152 and/or axes 160 such that, rotation of one roller 152 may result in the simultaneous rotation of at least one other roller 152. For example, body 156 may include a continuous belt configured to rotate about two or more wheel (e.g., rollers 152).

Figure 80A:
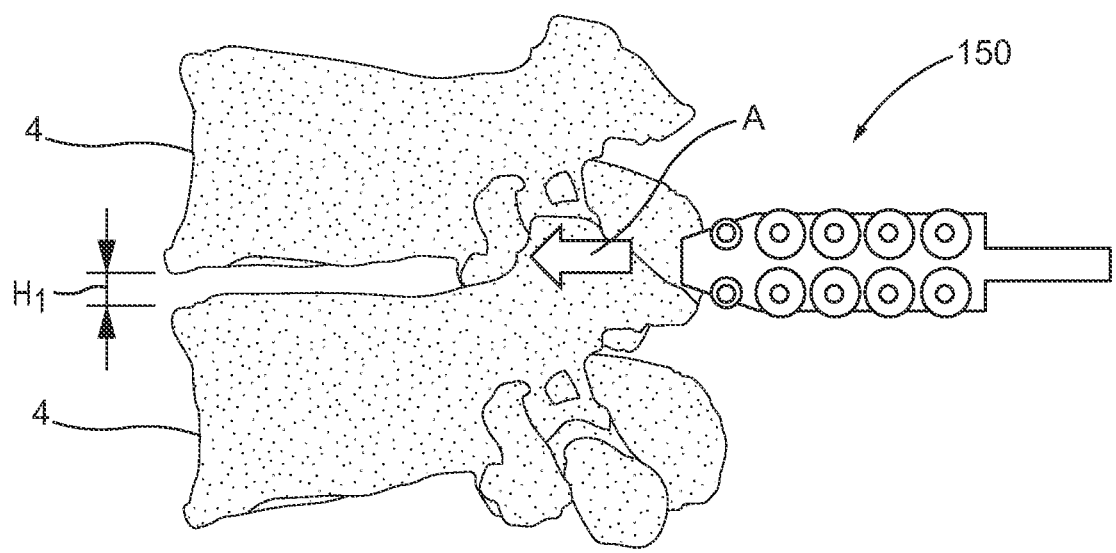
FIGS. 80A and 80B illustrate the exemplary tool of FIG. 79 in use.
Figure 80B:
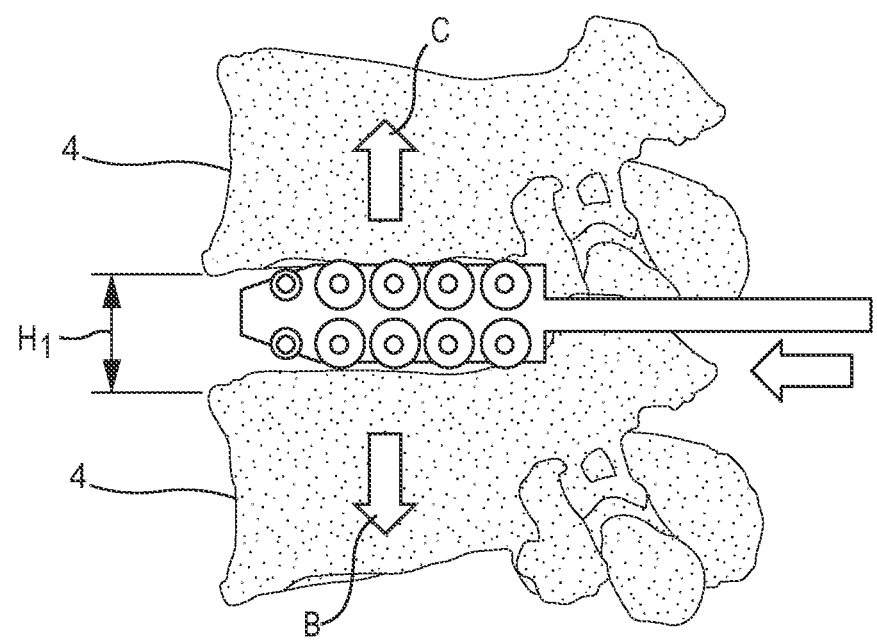

FIGS. 80A and 80B illustrate insertion of an exemplary tool 150. For example, as shown in FIG. 80A, prior to insertion of tool 150 therebetween, a pair of adjacent vertebrae 4 may be spaced from one another by a height $H_1$. That is, an end plate of a first vertebra 4 facing a second vertebra 4 may be positioned at a height of $H_1$ apart from a corresponding end plate of the second vertebra 4. In order to determine an appropriate size and/or positioning of an interbody device 10 to be received between adjacent vertebrae 4, tool 150 may be moved in the direction of arrow A. Upon insertion of tool 150 in the direction A, first and second vertebra 4 may be distracted (e.g., spread apart) from one another as shown in FIG. 80B. That is a first vertebra 4 may be urged away from the second vertebra 4 in the direction of arrow B, while a second vertebra 4 may be urged away from the first vertebra 4 in the direction of arrow C. Accordingly, after insertion of tool 150 between a pair of adjacent vertebra 4, the pair of adjacent vertebrae 4 may be spaced from one another by a height $H_2$. That is, an end plate a first vertebra 4 facing a second vertebra 4 may be positioned at a height of $H_2$ apart from an end plate of the second vertebra 4 facing the first vertebra 4. Further, upon insertion of tool 150, surrounding tension bands (e.g., ligaments and/or muscles) may be loosened. Accordingly, following removal of tool 150 from the adjacent vertebrae 4 may collapse towards one another, however, subsequent insertion of an interbody device 10 therebetween may require less force.

Further, as noted above, shaft 154 may be removably coupled to body 156. For example, shaft 154 may be threaded so as to cooperate with a threaded hole in body 156, or vice versa. In some arrangements, shaft 154 may form a portion of a kit including shaft 154 and a plurality of bodies 156. Each body 156 of the plurality of bodies 156 may have varied number and/or configuration of rollers 152, nose 158 angle, and/or varies dimensions (e.g., length, width, height, etc.). Accordingly, a medical professional may selectively choose one or more bodies 156 of the plurality of bodies 156 to couple to shaft 154. It is understood that any appropriate coupling structure other than threading is also contemplated. For example, any corresponding mating arrangement may be used to selectively couple and decouple shaft 154 from body 156.

Figure 81:
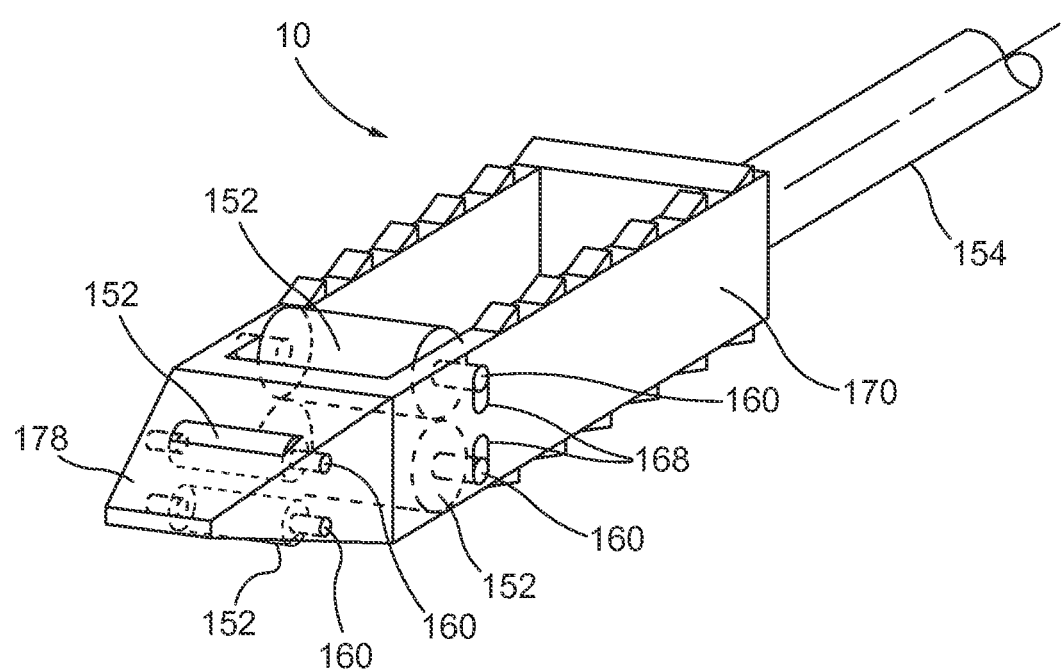
FIG. 81 illustrates an exemplary composite tool and cage of an interbody device.

In some arrangements, the above-noted features of body 156 may be incorporated into any of the above-noted interbody devices 10. For example, as discussed above, standalone and/or composite interbody devices 10 may include a cage. Indeed, such a cage may include any of the arrangements illustrated in FIGS. 23-32. As shown in FIG. 81, an interbody device 10 may include cage 170. Cage 170 may be similar to body 156 as described above in connection with FIGS. 79, 80A, and 80B. For example, cage 170 may include one or more friction reducing elements such as, for example, bearings, wheels, discs, rollers 152, and/or combinations thereof. Indeed, as shown in FIG. 81, rollers 152 may be generally cylindrical. Alternatively, rollers 152 may include any appropriate geometric shape. In some arrangements, one or more rollers 152 may be textured. As such, rollers 152 may score vertebra 4 to promote bleeding therefrom.

As shown in FIG. 81, cage 170 may include four rollers 152. For example, one roller 152 along a top portion of cage 170 configured to reduce friction between interbody device 10 and a first vertebra 4, and one roller 152 along a bottom portion of cage 170 configured to reduce friction between interbody device 10 and a second vertebra 4. Additionally, one or more rollers 152 may be positioned along a top portion of a nose 178 and a bottom portion of nose 178. Such an arrangement is merely exemplary. Rather, more or fewer rollers 152 may be positioned along cage 170. Further, in some arrangements, a different number of rollers 152 may be positioned along the top portion of cage 170 and/or top portion of nose 178 than the bottom portion of cage 170 and/or the bottom portion of nose 178. Rollers 152 of FIG. 81 may have similar features as those described above in connection with FIG. 79. As shown in FIG. 81 the rollers 152 may be disposed relatively closer to a distal end of cage 170. Additionally, one or more of rollers 152 may be vertically slidable (e.g., radially inwardly and outwardly) as well as rotatable. For example, cage 170 may include one or more slots 168. Slots 168 may be configured (e.g., sized and positioned) so as to receive axes 160 of rollers 152 therein. That is, a first side of each axis 160 may be received within a first slot 168 while a second side of each axis 160 may be received within a second, corresponding slot 168. In such a manner, each axis 160, and therefore, each roller 152, may be urged along slots 168 radially inwardly and outwardly relative to a central axis of cage 170. Further, each axis 160 of each roller 152 may be biased (e.g., spring biased) radially inwardly. Shaft 154 may be removably coupled to cage 170 so as to urge each roller 152 radially outwardly, as will be described in further detail below.

Figure 82A:
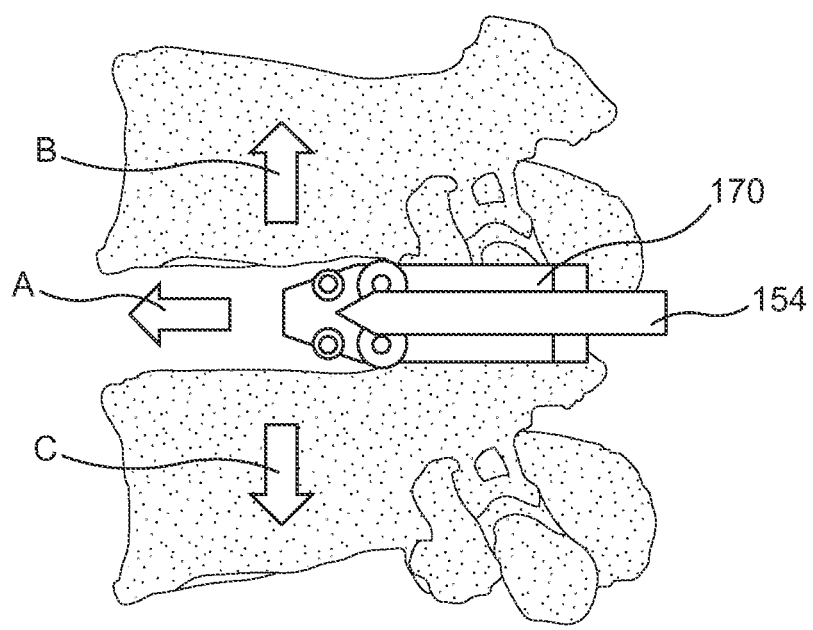
FIGS. 82A-82C illustrate the composite tool and cage of FIG. 81 in use.
Figure 82B:
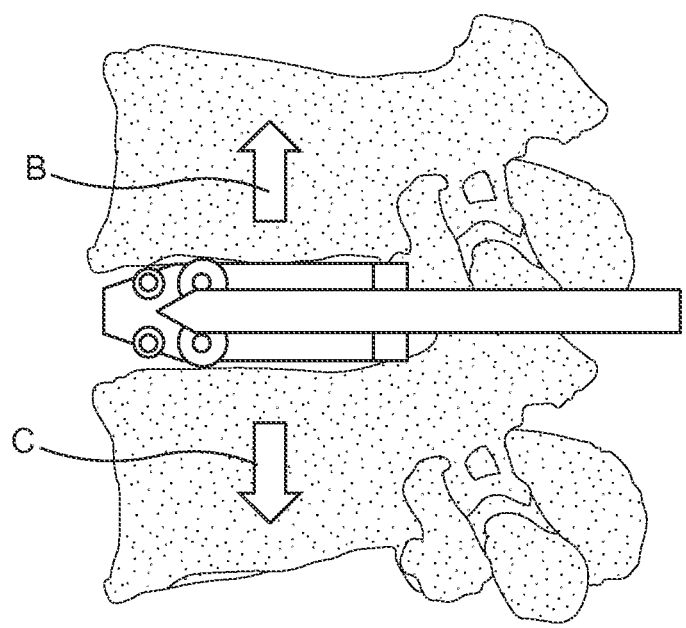
Figure 82C:
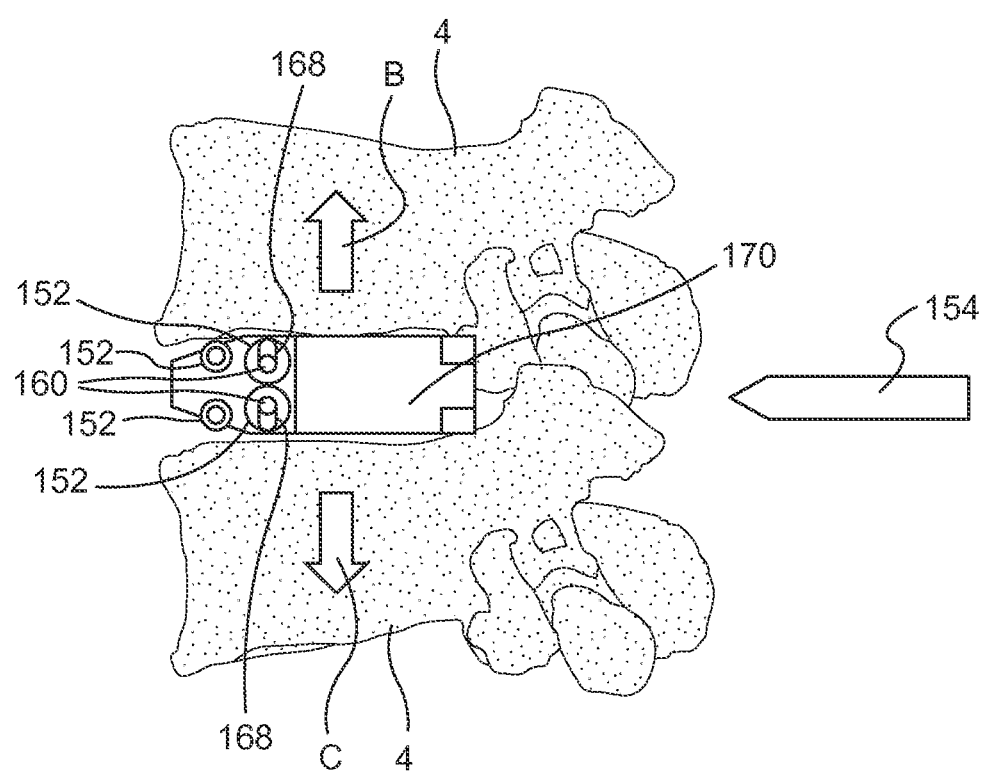

For example, FIGS. 82A-C illustrate insertion of an interbody device comprising a cage 170. Indeed, as shown in FIGS. 82A and 82B, shaft 154 may inserted into cage 170 thereby urging rollers 152 radially outward. As such, rollers 152 may reduce friction between cage 170 and adjacent vertebrae 4 as cage 170 is moved in the direction of arrow A. Upon insertion of cage 170 in the direction A, first and second vertebrae 4 may be spread apart from one another as shown. That is, a first vertebra 4 may be urged away from the second vertebra 4 in a direction of arrow B, while a second vertebra 4 may be urged away from the first vertebra 4 in a direction of arrow C. After insertion of cage 170 between a pair of adjacent vertebrae 4, shaft 154 may be removed, as shown in FIG. 82C. Accordingly, rollers 152 may no longer be urged radially outwardly. Further, due to the biasing of rollers 152, once shaft 154 is removed from cage 170, axes 160 of one or more rollers 152 may move along slots 168 such that rollers 152 may retract into an interior of cage 170. In some arrangements, shaft 154 may be hollow and include one or more holes, through passages, or channels (not shown). In such cases, bone graft or other suitable ingrowth promoting material may be injected through shaft 154 into cage 170. In other words, shaft 154 may be configured for the delivery of bone graft therethrough and into cage 170.

Figure 83:
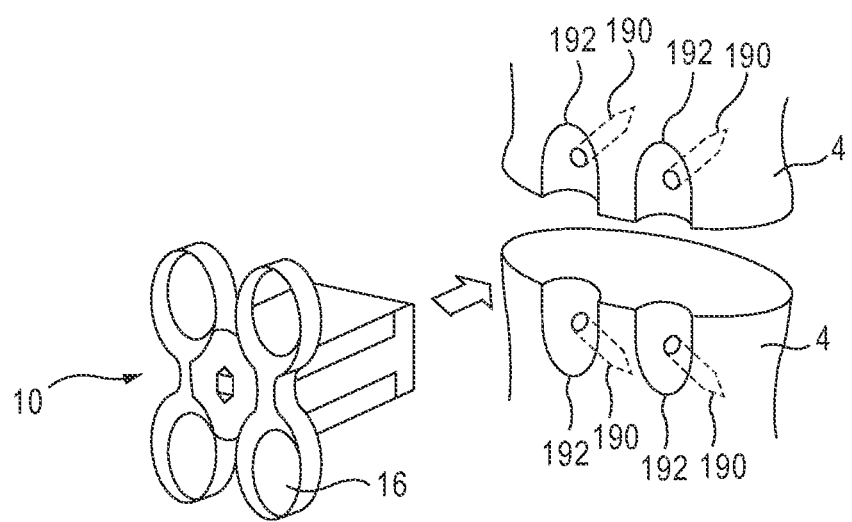
FIGS. 83-87 illustrate exemplary interbody devices positioned between adjacent vertebra.
Figure 84:
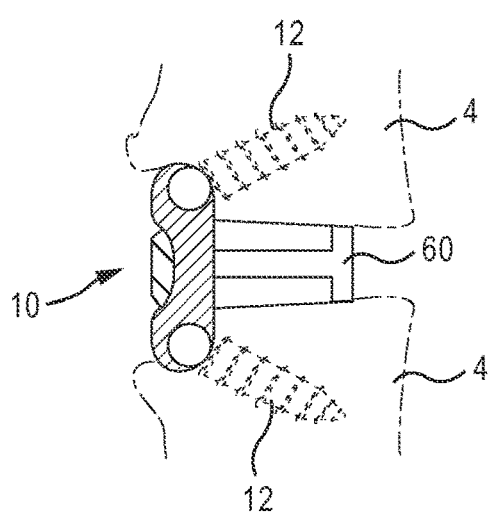
Figure 85:
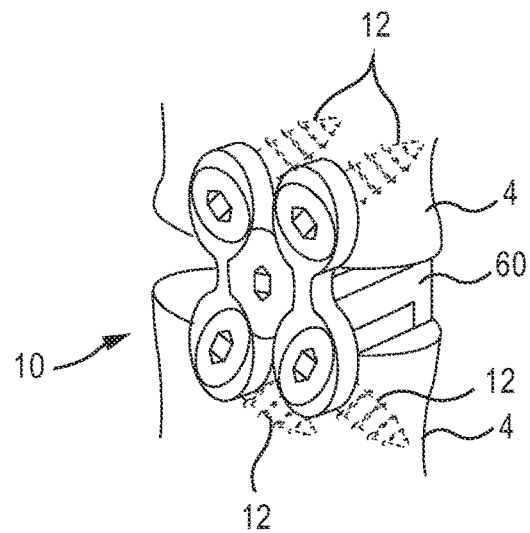
Figure 86:
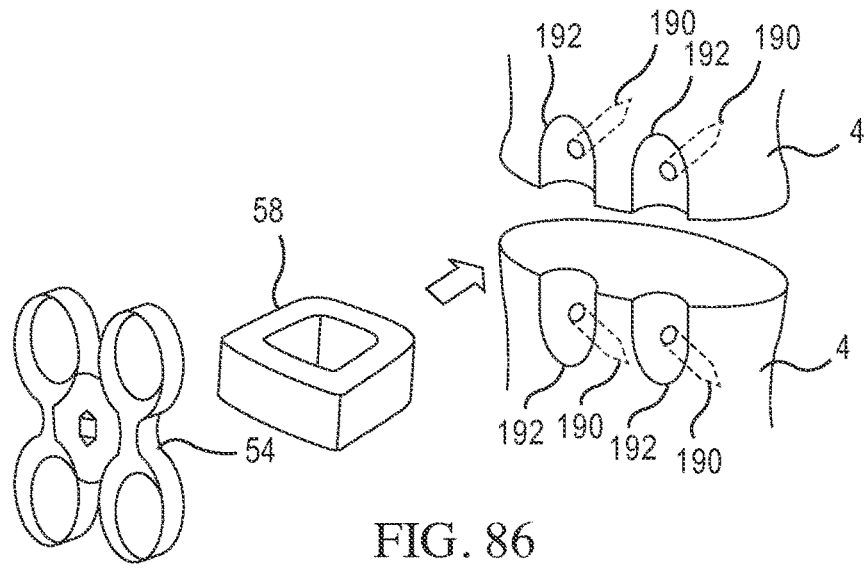
Figure 87:
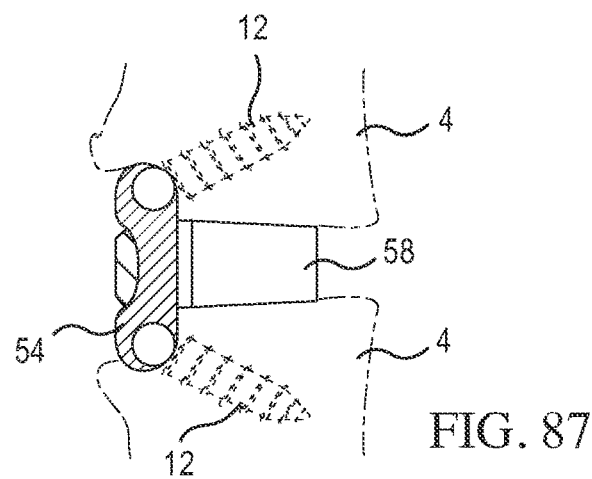

During insertion, one or more tools may be utilized to prepare vertebra(e) 4 for insertion of interbody device 10. For example, as shown in FIG. 83, any appropriate tool may utilized to form one or more holes or counter bores within vertebra 4 for receipt of suitable fasteners such as, for example, screws 12. Accordingly, as shown in FIGS. 83 and 86, following the removal of a tool(s), each vertebra 4 may include one or more pilot holes 190 formed by a pilot hole feature (not shown) of a tool, and one or more counter bores 192 formed by reamer (not shown) of a tool. As shown in FIGS. 83 and 86, for example, two pilot holes 190 and two counterbores 192 may be formed in each vertebra 4. Accordingly, the pair of adjacent vertebrae 4 may be prepared to receive interbody device 10 therebetween. For example, as shown in FIGS. 83 and 86, after formation of pilot holes 190 and/or counterbores 192, interbody device 10 may be inserted between adjacent vertebra 4. Interbody device 10 may include any of the previously described features, such as any of the above-noted screw blocking mechanisms. Further, as shown in FIGS. 83 and 84, interbody device 10 may comprise any of the above-noted standalone devices including a frame 60. Alternatively, as shown in FIGS. 86 and 87, interbody device 10 may comprise any of the above-noted composite devices including a panel 54 and cage portion 58. Following insertion between adjacent vertebrae 4, one or more screws 12 may be inserted through one or more apertures 16 into a counterbore 192 and pilot hole 190 so as to secure interbody device 10 in place as shown in FIG. 85. For example, a first screw 12 may be passed through a first aperture 16, into a first counter bores 192 and into a first pilot hole 190.

Figure 88:
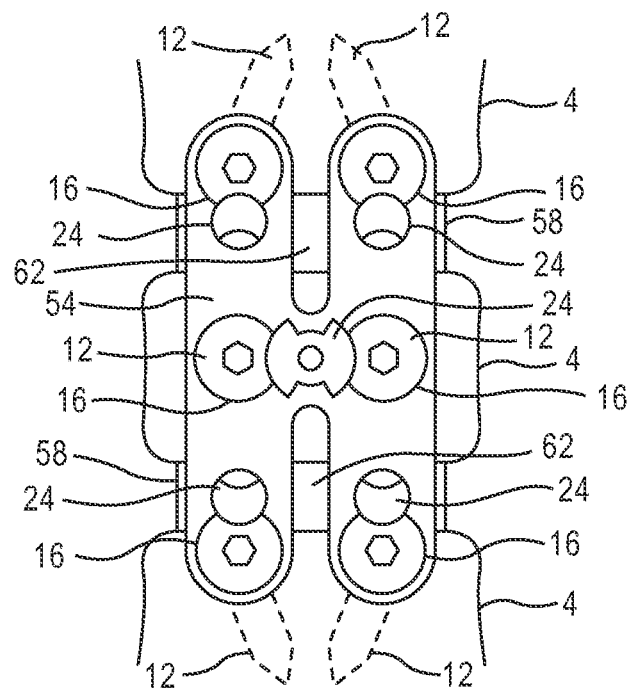
FIGS. 88-91 illustrate exemplary multi-vertebrae devices.
Figure 89:
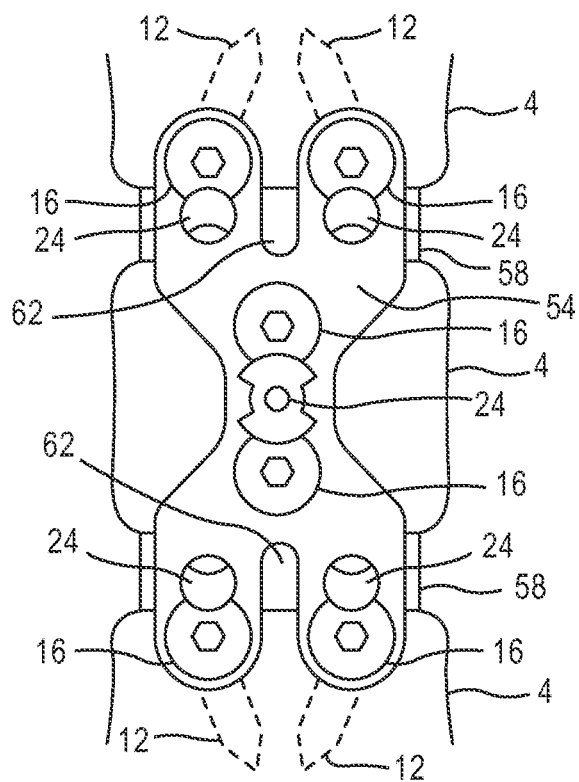
Figure 90:
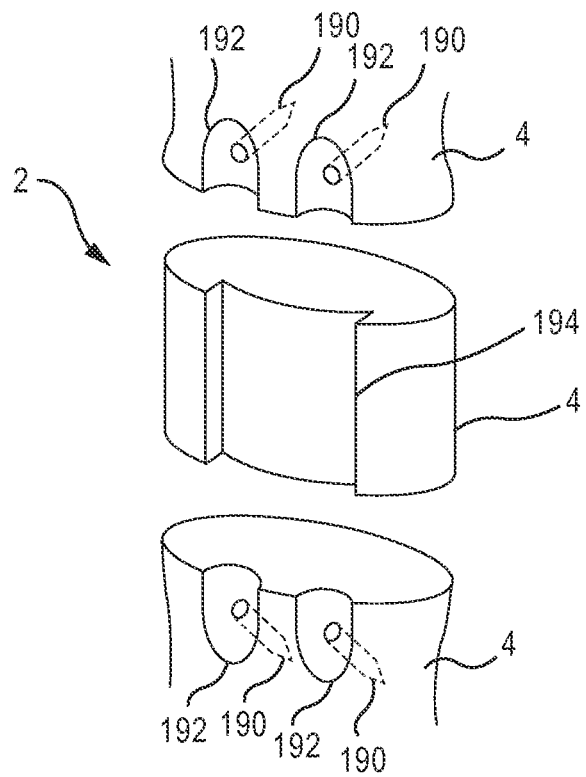
Figure 91:
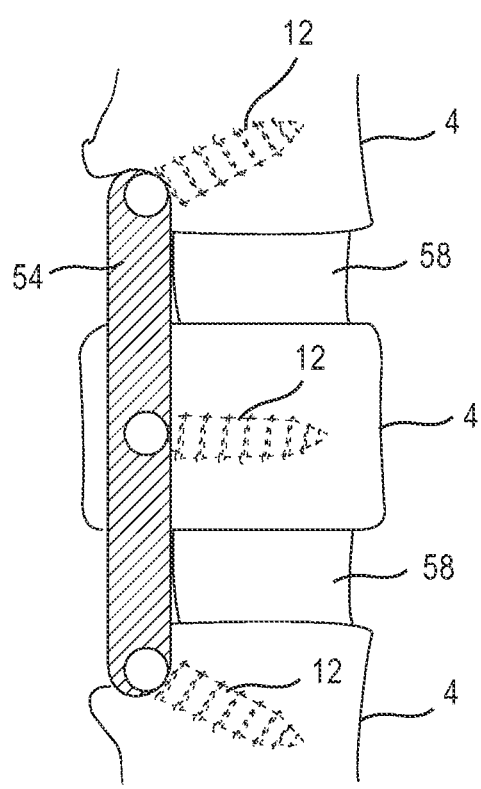

As noted above in connection with FIGS. 78A-78E, interbody devices 10 may span more than two adjacent vertebra 4. For example, as shown in FIGS. 88 and 89, an exemplary interbody device 10 may be configured to couple three or more vertebrae 4. For example, interbody device 10 may comprise a composite device, including a panel 54 and cage portion 58. Panels 54 may be similar to those described above, and may include any appropriate number of apertures 16 for receiving corresponding screws 12 therethrough. Additionally, any of panels 54 may include any of the screw blocking mechanisms or windows 62 noted above. For example, as shown in each of FIGS. 88 and 89, panel 54 may include six apertures 16, each configured to receive a screw therethrough and each associated with an exemplary offsetting element 24. Indeed, as shown in FIG. 88, panel 54 may have a general H-shape, defining six apertures 16 along two columns and three rows. Accordingly, panel 54 may define three apertures 16 on the left of a central longitudinal axis and three apertures 16 on the right of the central longitudinal axis. Additionally, panel 54 may be configured such that two apertures 16 are positioned along each vertebra 4. As shown in FIG. 89, however, panel 54 may have a general X-shape, defining six apertures 16. In such an arrangement, a central two apertures 16 may be aligned along a central longitudinal axis, while two apertures 16 are positioned to the left of the central longitudinal axis and two apertures are positioned to the right of the central longitudinal axis. Additionally, panel 54 may be configured such that two apertures 16 are positioned along each vertebra 4. As shown in FIG. 90, prior to placement of panel 54 and or cage portion 58 within spinal column, one or more counterbores 192 and pilot holes 190 may be formed. Additionally, one or more grooves, recesses and/or channels 194 may be formed along an anterior surface of vertebra 4. Channel 194 may be sized so as to receive at least a portion of frame 54 therein. Accordingly, as shown in FIG. 91, interbody device 10 may be received along spinal column 2.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. An intervertebral device, comprising:
    a body configured for insertion between adjacent vertebrae of a patient, the body including a wall having a first surface, a second surface, and a thickness extending between the first and second surfaces, wherein the wall includes a through aperture extending between a first opening on the first surface and a second opening on the second surface, the through aperture configured to receive a fastening element;
    a recess disposed in a side wall of the aperture, the recess including a pocket extending into the thickness of the body in a direction substantially transverse to an axis of the aperture, the pocket including a top overhanging surface portion proximate to the first surface and a bottom overhanging surface portion proximate to the second surface, the top and bottom overhanging surface portions extending inwardly towards the aperture; and
    at least one offsetting element positioned adjacent the through aperture, wherein the at least one offsetting element is configured to apply a force to the fastening element when the fastening element is seated within the aperture; wherein application of the force on the fastening element by the at least one offsetting element is configured to laterally urge the fastening element into the recess.

2. The device of claim 1, wherein, upon the application of a force on the fastening element by the at least one offsetting element, at least a portion of the fastening element is urged into direct contact with the top overhanging surface portion proximate to the first surface, wherein interference between the top overhanging surface portion and the portion of the fastening element urges the fastening element in a posterior direction relative to the first surface.

3. The device of claim 1, wherein the fastening element includes a rounded head, and the recess is configured to correspond in profile with at least a portion of the rounded head, the recess engaging a lateral portion of the rounded head of the fastening element to retain the fastening element within the through aperture.

4. The device of claim 1, wherein the recess is configured to receive an actuation portion of the fastening element.

5. The device of claim 1, wherein the fastening element is a screw, and the recess is configured to receive a head of the screw.

6. The device of claim 1, wherein actuating the at least one offsetting element causes the at least one offsetting element to engage a portion of the fastening element.

7. The device of claim 1, wherein the at least one offsetting element is eccentrically shaped.

8. The device of claim 1, wherein the at least one offsetting element includes at least one of a planar portion and a concave portion, and wherein the at least one offsetting element includes a convex portion.

9. The device of claim 1, wherein the at least one offsetting element is movable relative to the body.

10. The device of claim 1, wherein the fastening element is a first fastening element, the device further including:
a second fastening element, the through aperture being configured to receive each of the first fastening element and the second fastening element.

11. The device of claim 10, wherein application of a force on the second fastening element by the at least one offsetting element is configured to laterally urge the second fastening element relative to the recess.

12. The device of claim 11, wherein the at least one offsetting element is positioned between each of the first fastening element and the second fastening element, and wherein actuation of the at least one offsetting element is configured to laterally urge the first fastening element and the second fastening element relative to the recess, simultaneously.

13. The device of claim 11, wherein the at least one offsetting element is a first offsetting element, the device further comprising:
a second offsetting element positioned adjacent said through aperture, wherein application of a force on the second fastening element by the second offsetting element is configured to laterally urge the second fastening element relative to the recess independently of the first fastening element.

14. An intervertebral device, comprising:
a body configured for insertion between adjacent vertebrae of a patient, the body including a wall having a first surface, a second surface, and a thickness extending between the first and second surfaces, wherein the wall includes a through aperture extending between a first opening on the first surface and a second opening on the second surface, wherein the body includes at least one lateral support extending from the first wall;
a recess disposed in a side wall of the aperture, the recess including a pocket extending into the thickness of the body in a direction substantially transverse to an axis of the aperture, the pocket including a top overhanging surface portion proximate to the first surface and a bottom overhanging surface portion proximate to the second surface, the top and bottom overhanging surface portions extending inwardly towards the aperture;
a fastening element positioned within the through aperture; and
at least one offsetting element positioned adjacent said through aperture, wherein the at least one offsetting element is configured to apply a force to the fastening element when the fastening element is seated within the aperture; wherein application of the force on the fastening element by the at least one offsetting element is configured to laterally urge the fastening element into the recess.

15. The device of claim 14, wherein at least a portion of the body is radiopaque and each of the first and second windows is radiolucent.

16. The device of claim 15, further including:
a radiolucent graft containment sheath disposed about the body.

17. The device of claim 14, wherein the body includes a tapered keel.

* * * * *